US006582956B1

(12) United States Patent
Gelman et al.

(10) Patent No.: US 6,582,956 B1
(45) **Date of Patent: *Jun. 24, 2003**

(54) TUMOR SUPPRESSOR GENE

(75) Inventors: Irwin H. Gelman, New York, NY (US); Susan Jaken, Lake Placid, NY (US)

(73) Assignee: Mount Sinai School of Medicine, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/978,277

(22) Filed: Nov. 25, 1997

(Under 37 CFR 1.47)

Related U.S. Application Data

(63) Continuation of application No. 08/665,401, filed on Jun. 8, 1996, now abandoned, which is a continuation-in-part of application No. 08/635,121, filed on Apr. 19, 1996, now Pat. No. 5,910,442.

(51) Int. Cl.$^7$ .......................... C12N 15/12; C12N 15/85

(52) U.S. Cl. .................... 435/325; 435/320.1; 435/455; 536/23.1; 536/23.5

(58) Field of Search ............................. 435/320.1, 325, 435/172.3, 455; 514/44; 536/23.1, 23.5; 530/350

(56) References Cited

U.S. PATENT DOCUMENTS 5,741,890 A 4/1998 Scott et al. ................. 530/300
5,910,442 A * 6/1999 Gelman et al. ............. 435/325

OTHER PUBLICATIONS

Chapline et al. Identification of a Major Protein Kinase C–Binding Protein and Substrate in Rat Embryo Fibroblasts. Journal of Biological Chemistry, vol. 271, No. 11, pp. 6417–6422, Mar. 15, 1996.*

Lin et al. Isolation and Characterization of a Novel Mitogenic Regulatory Gene, 322, Which is Transcriptionally Suppressed in Cells Transformend by src and ras. Molecular and Cellular Biology, vol. 15, No. 5, pp. 2754–2762, May 1995.*

Gelman, I. H. Direct submission. GenBank Acc. No. U23146; US Natl. Library of Medicine, Bethesda, MD; accessed by PTO on Oct. 31, 1998, Mar. 21, 1995.*

Orkin et al. Report and recommendations of the panel to assess the NIH investment in research on gene therapy, Dec. 07, 1995, Mar. 21, 1995.*

Sager, 1989, Tumor Suppressor Genes: The Puzzle and the Promise, Science 246: 1406–1412.

Lee et al., 1991, Positive Selection of Candidate Tumor–Suppressor Genes by Subtractive Hybridization, Proc. Natl. Acad. Sci. USA 88:2825–2829.

Gordon et al., 1992, Molecular Cloning and Preliminary Characterization of a Novel Cytoplasmic Antigen Recognized by Myasthenia Gravis Sera, J. Clin. Invest. 90: 992–999.

Gluck, 1993, Suppression of Tumorigenicity in Simian Virus 40–Transformed 3T3 Cells Transfected with α–actinin cDNA, Proc. Natl. Acad. Sci. USA, 90:383–387.

Hirada et al., 1993, Anti–Oncogenic and Oncogenic Potentials of Interferon Regulatory Factors –1 and –2, Science, 259: 971–974.

Levine et al, 1993, The Tumor Suppressor Genes, Ann. Rev. Biochem. 62:623–651.

Prasad et al., 1993, Expression of Transduced Tropomyosin 1 cDNA Suppresses Neoplastic Growth of Cells Transformed by the ras Oncogene, Proc. Natl. Acad. Sci. USA 90:7039–7043.

Contente et al., 1993, Expression of Gene rrg Is Associated with Reversion of NIH 3T3 Transformed by LTR–c–H–ras, Science 249:796–798.

Houle et al., 1993, Tumor–Suppressive Effect of the Retinoic acid Receptor β in Human Epidermoid Lung Cancer Cells, Proc. Natl. Acad. Sci. USA 90:985–989.

Mishra et al., 1994, Regulation of the Suspected Tumor Suppressor Gene Product CLP in Human Breast Epithelial Cells, J. Cell. Biochem. 18 (Supp):171.

Ozaki et al., 1994, Tumor–Suppressive Activity of N03 Gene Product in v–src–transformed Rat 3Y1 Fibroblasts[1], Cancer Res. 54:646–648.

Zou et al., 1994, Maspin, A Serpin With Tumor–Suppressing Activity in Human Mammary Epithelial Cells, Science 263:526–529.

Gelman et al., 1995, Genebank Accession No. RNU23146.

Gelman et al., 1996, Genebank Accession No. A57376.

Lin et al., 1996, A Novel src– and ras–suppressed Protein Kinase C Substrate Associated with Cytoskeletal Architecture*, J. Biol. Chemistry 45:28430–28438.

* cited by examiner

*Primary Examiner*—Scott D. Priebe
(74) *Attorney, Agent, or Firm*—Baker Botts L.L.P.

(57) ABSTRACT

The present invention relates to a novel tumor suppressor gene, SSeCKS. The SSeCKS gene product is a substrate of protien kinase C and acts as a mitogenic regulator and as an inhibitor of the transformed phenotype. In various embodiments, the present invention relates to the SSeCKS gene and protein and in particular, to rat and human SSeCKS gene and protein. Furthermore, the present invention provides for the use of such genes and proteins in diagnostic and therapeutic methods.

9 Claims, 54 Drawing Sheets

Figure 1:
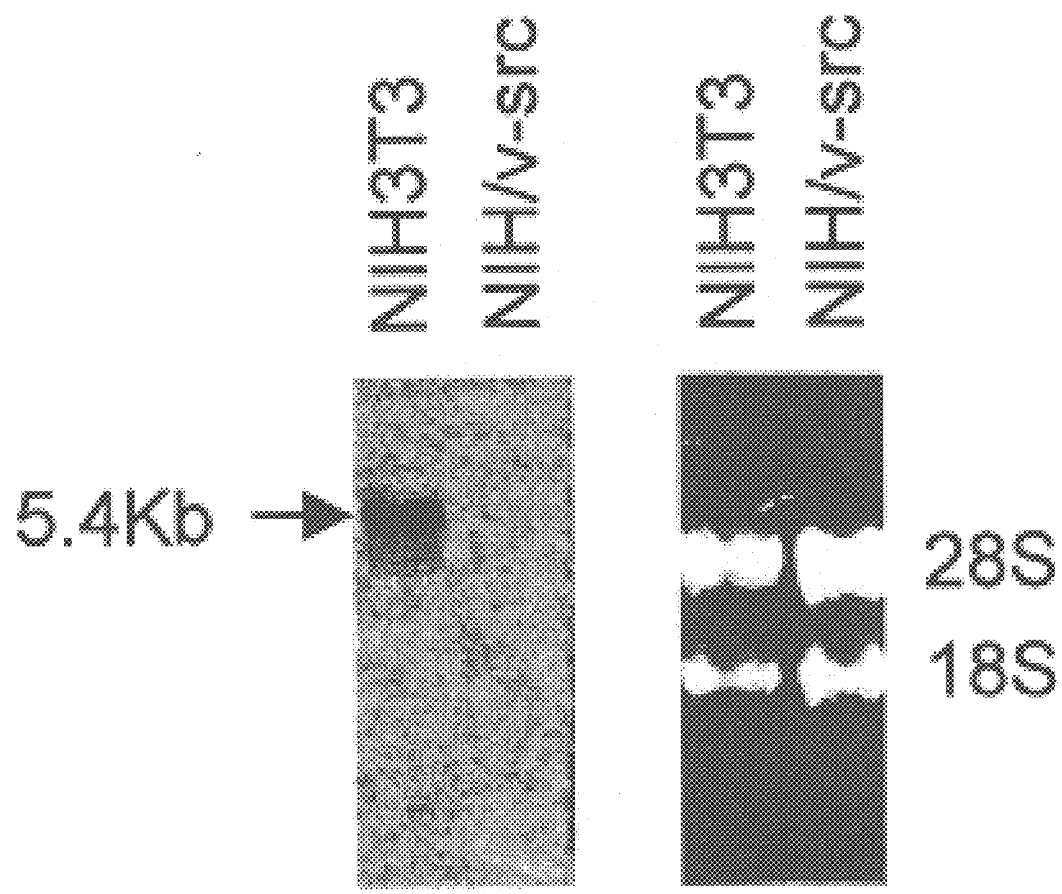

```
      ggaaaagacagagccagcctcggaggagcaggagccggcagaagacacagaccaggccag   60
      gttgtcagcagactacgagaaggtggagctgcctttggaagaccaggttggtgacctgga  120
      ggcatcgtcagaggagaagtgtgctcctttggcaacggaagtgtttgatgagaagatgga  180
                                                               M  E    2

181   agcccaccaagaagttgttgcagaggtccacgtgagcaccgtggagaagacagaggagga  240
3      A  H  Q  E  V  V  A  E  V  E  V  S  T  V  E  K  T  E  E  E   22

241   gcagggaggaggaggagaggctgaagggggcgtggtggtagaaggaacaggagaatcctt  300
23     Q  G  G  G  G  E  A  E  G  G  V  V  V  E  G  T  G  E  S  L   42
          -------------------------

301   gccccctgagaaactggctgagccccaggaggtcccccaggaagctgagcctgctgagga  360
43     P  P  E  K  L  A  E  P  Q  E  V  P  Q  E  A  E  P  A  E  E   62

361   gctgatgaagagcagagagatgtgtgtctctggaggagaccacactcaactgacagacct  420
63     L  M  K  S  R  E  M  C  V  E  G  G  D  H  T  Q  L  T  D  L   82

421   aagtcctgaagagaagacgctgcccaaacacccagaaggcattgtcagtgaggtggagat  480
83     S  P  E  E  K  T  L  P  K  H  P  E  G  I  V  S  E  V  E  M  102

481   gctgtcctctcaggaaagaatcaaggtacagggaagtcccttgaagaaactcttcagtag  540
103    L  S  S  Q  E  R  I  K  V  Q  G  S  P  L  K  K  L  F  S  S  122

541   ctcaggcttaaagaagctgtctgggaagaagcagaaggggaaacgaggaggtgggggaga  600
123    S  G  L  K  K  L  S  G  K  K  Q  K  G  K  R  G  G  G  G  D  142
                                                    ----------

601   cgaagagcctggagaataccaacacattcacaccgaatccccagagagtgctgatgagca  660
143    E  E  P  G  E  Y  Q  H  I  H  T  E  S  P  E  S  A  D  E  Q  162
```

FIG.3A

```
661   gaagggagagagctctgcgtcgtcccccgaggagcctgaggagaccacgtgtctggagaa   720
163    K  G  E  S  S  A  S  S  P  E  E  P  E  E  T  T  C  L  E  K    182

721   agggccgctggaagcacccaggatggggaagctgaggaaggaactacttcgtggagagaa   780
183    G  P  L  E  A  P  R  M  G  K  L  R  K  E  L  L  R  G  E  K    202

781   gaagaggaaggatcactccctgggcatccttcaaaaagatggtgacacccaagaaacggt   840
203    K  R  K  D  H  S  L  G  I  L  Q·K  D  G  D  T  Q  E  T  V    222

841   ccgaagaccttctgagagtgacaaggaggaagagctggagaaggtcaagagcgccacctt   900
223    R  R  P  S  E  S  D  K  E  E  E  L  E  K  V  K  S  A  T  L    242

901   gtcctccactgatagcacagtgtcagaaatgcaagatgaagtcaaaactgttggtgagga   960
243    S  S  T  D  S  T  V  S  E  M  Q  D  E  V  K  T  V  G  E  E    262

961   acaaaagccagaggaaccaaagcgtagggtggatacttcagtgtcttgggaagcactgat   1020
263    Q  K  P  E  E  P  K  R  R  V  D  T  S  V  S  W  E  A  L  I    282

1021  ttgtgtcggatcatccaagaagagagcaaggaaggcatcctcttcagatataagagggcc   1080
283    C  V  G  S  S  K  K  R  A  R  K  A  S  S  S  D  I  R  G  P    302

1081  aaggacactgggaggggggacagtcacagagcagaggaggccagcaaagacaaagaagccg   1140
303    R  T  L  G  G  G  Q  S  Q  S  R  G  G  Q  Q  R  Q  R  S  R    322
                  ______________________________

1141  aacagacgctgttcctgccagcacccaggagcaggaccaagcgcaaggaagttcctcacc   1200
323    T  D  A  V  P  A  S  T  Q  E  Q  D  Q  A  Q  G  S  S  S  P    342

1201  cgagccagcgggaagcccttccgaaggggaaggtgtctccacttgggagtcatttaaaag   1260
343    E  P  A  G  S  P  S  E  G  E  G  V  S  T  W  E  S  F  K  R    362
```

FIG.3B

```
1261  attagtcactccaagaaaaaaatccaagtcaaaactggaagagaaagaagccggaaggac  1320
 363   L  V  T  P  R  K  K  S  K  S  K  L  E  E  K  E  A  G  R  T    382

1321  tctagttgtaggagcaggttgtccactgagatcgaaccgtgtagagaagaatcttgggtt  1380
 383   L  V  V  G  A  G  C  P  L  R  S  N  R  V  E  K  N  L  G  F    402

1381  tccattaagaaattcatccccggacggcggaagaaaagggcagatgggaaggcaagaaca  1440
 403   P  L  R  N  S  S  P  D  G  G  R  K  G  Q  M  G  R  Q  E  Q    422

1441  agccactgtggaagactcagggccagtggagataaatgaggacgagcctgatgtcccagc  1500
 423   A  T  V  E  D  S  G  P  V  E  I  N  E  D  E  P  D  V  P  A    442

1501  agtcgtgcctctgtctgagtatgatgcagtggagagggagaagatggaagcccaggggaa  1560
 443   V  V  P  L  S  E  Y  D  A  V  E  R  E  K  M  E  A  Q  G  N    462

1561  tgcggagctgcccagctgctggggctgtgtagtgtccgaggagctcagtaagactctggt  1620
 463   A  E  L  P  S  C  W  G  C  V  V  S  E  E  L  S  K  T  L  V    482

1621  ccacactgtgagtgtcgcagtcattgatgggaccagggcagtcaccagtgtcgaagagcg  1680
 483   H  T  V  S  V  A  V  I  D  G  T  R  A  K  T  S  K  E  E  R    502

1681  gtctccttcgtggatatccgcttccgtaacagaacctcttgaacacacagcgggagaagc  1740
 503   S  P  S  W  I  S  A  S  V  T  E  P  L  E  H  T  A  G  E  A    522

1741  catgccacctgttgaagaggtcactgaaaaagacatcattgcagaagaaactcctgtgct  1800
 523   M  P  P  V  E  E  V  T  E  K  D  I  I  A  E  E  T  P  V  L    542

1801  cacccagacgttaccagagggtaaagatgcccatgacgacatggtcaccagtgaagtgga  1860
 543   T  Q  T  L  P  E  G  K  D  A  H  D  D  M  V  T  S  E  V  D    562
```

FIG.3C

```
1861  tttcacctcagaagctgtgacagccacagagacctcagaggctctccgtactgaagaagt  1920
563    F  T  S  E  A  V  T  A  T  E  T  S  E  A  L  R  T  E  E  V   582

1921  taccgaagcatcgggggccgaagagaccacagacatggtgtccgcagtttcccagctgac  1980
583    T  E  A  S  G  A  E  E  T  T  D  M  V  S  A  V  S  Q  L  T   602

1981  tgactccccagacaccacagaggaagccaccccagttcaggaggtagagggtggtgtgct  2040
603    D  S  P  D  T  T  E  E  A  T  P  V  Q  E  V  E  G  G  V  L   622

2041  agatacagaagaagaggagcgccagacgcaggccatcctccaagccgttgcagacaaggt  2100
623    D  T  E  E  E  E  R  Q  T  Q  A  I  L  Q  A  V  A  D  K  V   642

2101  gaaagaggagtcccaggtgcctgcaacccagactgtgcagagaacggggtcaaaagcact  2160
643    K  E  E  S  Q  V  P  A  T  Q  T  V  Q  R  T  G  S  K  A  L   662

2161  ggagaaggttgaggaggtagaggaggactccgaagtgctggcttcggagaaagagaagga  2220
663    E  K  V  E  E  V  E  E  D  S  E  V  L  A  S  E  K  E  K  D   682

2221  cgttatgccgaaaggacccgtgcaggaagctggagctgagcatcttgcacagggctctga  2280
683    V  M  P  K  G  P  V  Q  E  A  G  A  E  H  L  A  Q  G  S  E   702

2281  gactggacaggctactccagagagccttgaagttcctgaagtcacagcagatgtagacca  2340
703    T  G  Q  A  T  P  E  S  L  E  V  P  E  V  T  A  D  V  D  H   722

2341  tgtcgccacgtgccaggttatcaagctccagcagctgatggaacaggccgtggcccctga  2400
723    V  A  T  C  Q  V  I  K  L  Q  Q  L  M  E  Q  A  V  A  P  E   742

2401  gtcatccgaaaccttgacagacagtgagacaaatggaagcactcccttagcagattcaga  2460
743    S  S  E  T  L  T  D  S  E  T  N  G  S  T  R  L  A  D  S  D   762
```

FIG.3D

```
2461  cactgcagatgggacacagcaagatgaaaccattgacagccaggacagtaaagccactgc  2520
763    T  A  D  G  T  Q  Q  D  E  T  I  D  S  Q  D  S  K  A  T  A    782

2521  agctgtcaggcagtcacaggtcacagaagaagaggcggctactgctcagaaagaggagcc  2580
783    A  V  E  Q  S  Q  V  T  E  E  E  A  A  T  A  Q  K  E  E  P    802

2581  ttcgacactacctaataatgttccagcccaggaagaacatggggaagaaccaggaagaga  2640
803    S  T  L  P  N  N  V  P  A  Q  E  E  H  G  E  E  P  G  R  D    822

2641  tgttcttgaacctacacagcaagagcttgctgctgcagccgtgcccgtctggcaaaagac  2700
823    V  L  E  P  T  Q  Q  E  L  A  A  A  A  V  P  V  W  Q  K  T    842

2701  tgaggtgggtcaagagggtgaggttgactggttggatggagaaaaagtcaaagaagaaca  2760
843    E  V  G  Q  E  G  E  V  D  W  L  D  G  E  K  V  K  E  E  Q    862

2761  ggaggtgtttgtacactctggacccaacagtcaaaaggctgctgatgtgacatatgacag  2820
863    E  V  F  V  H  S  G  P  N  S  Q  K  A  A  D  V  T  Y  D  S    882

2821  tgaagtgatgggagtggccgggtgtcaggaaaaggagagtactgaagtgcagagtcttag  2880
883    E  V  M  G  V  A  G  C  Q  E  K  E  S  T  E  V  Q  S  L  S    902

2882  cctggaggagggagagatggaaactgacgttgaaaaggagaaaagggagacaaagccaga  2940
903    L  E  E  G  E  M  E  T  D  V  E  K  E  K  R  E  T  K  P  E    922

2941  gcaagtgagtgaagaaggtgagcaggaaacagccgctcctgagcatgaaaggaactacgg  3000
923    Q  V  S  E  E  G  E  Q  E  T  A  A  P  E  H  E  R  N  Y  G    942

3001  gaagccagtcctgacacttgacatgcccagctcagagaggggaaggcactgggaagcct  3060
943    K  P  V  L  T  L  D  M  P  S  S  E  R  G  K  A  L  G  S  L    962
```

FIG.3E

```
3061  tggaggaagcccttctctcccagaccaagacaaagcaggttgcatagaggttcaagttca  3120
963    G  G  S  P  S  L  P  D  Q  D  K  A  G  C  I  E  V  Q  V  Q   982

3121  aagcctggacacaacagtcactcaaacagcagaagctgtggaaaaggtcatagaaacggt  3180
983    S  L  D  T  T  V  T  Q  T  A  E  A  V  E  K  V  I  E  T  V   1002

3181  tgtgatttcagagacaggtgaaagtccagagtgtgtaggtgcacacttattaccagctga  3240
1003   V  I  S  E  T  G  E  S  P  E  C  V  G  A  H  L  L  P  A  E   1002
                                 Zn-finger
3241  gaagtcctctgcaacgggtggccactggactcttcagcatgcagaggacacggtacccct  3300
1023   K  S  S  A  T  G  G  H  W  T  L  Q  H  A  E  D  T  V  P  L   1042

3301  ggggcctgagtctcaggcagaatccatcccaatcatagtaactcctgctcctgaaagcac  3360
1043   G  P  E  S  Q  A  E  S  I  P  I  I  V  T  P  A  P  E  S  T   1062

3361  cctacatcctgacctacaaggagaaataagcgcatcccagagagagcgatcagaggaaga  3420
1063   L  H  P  D  L  Q  G  E  I  S  A  S  Q  R  E  R  S  E  E  E   1082

3421  ggacaagccagatgctggtcctgatgctgacggcaaggagagtacagcaatcgacaaagt  3480
1083   D  K  P  D  A  G  P  D  A  D  G  K  E  S  T  A  I  D  K  V   1102

3481  cctcaaggctgaacctgagatcctggaacttgagagtaagagcaacaagattgtgctgaa  3540
1103   L  K  A  E  P  E  I  L  E  L  E  S  K  S  N  K  I  V  L  N   1122

3541  cgtcattcagacagccgttgaccagttcgcacgtacagaaacagcccccgaaactcatgc  3600
1123   V  I  Q  T  A  V  D  Q  F  A  R  T  E  T  A  P  E  T  H  A   1142

3601  ttatgattcacagacccaggttcctgcaatgcgcttggacagcagggagcccaacagatg  3660
1143   Y  D  S  Q  T  Q  V  P  A  M  R  L  D  S  R  E  P  N  R  C   1162
```

FIG.3F

```
3661  ctggacaaaaatgaaagttgccaagatgaaacacccagtgccgcagcccagagaggactt  3720
1163   W  T  K  M  K  V  A  K  M  K  H  P  V  P  Q  P  R  E  D  L   1182

3721  gcaagtcctgaccgttctggaggcatggctcagctcggaaatgcttgccgcgcttgcagt  3780
1183   Q  V  L  T  V  L  E  A  W  L  S  S  E  M  L  A  A  L  A  V   1202

3781  tgaaagcgccggtgtcaaagtaagcattgagaagctgcctcctcaacccaaagatcaaaa  3840
1203   E  S  A  G  V  K  V  S  I  E  K  L  P  P  Q  P  K  D  Q  K   1222

3841  ggagcatgctgctgatggccctcagctccaaagcttagcccaggcagaggcagtgtctgg  3900
1223   E  H  A  A  D  G  P  Q  L  Q  S  L  A  Q  A  E  A  V  S  G   1242

3901  aaacctaaccaaagaatccccagacaccaacggaccaaagctaaccgaggagcgatgccc  3960
1243   N  L  T  K  E  S  P  D  T  N  G  P  K  L  T  E  E  R  C  P   1262

3961  ccaaaagttgaggtccaggaagaagaaatgtctaccaagtcagtcaaagagaacaaggcc  4020
1263   Q  K  L  R  S  R  K  K  K  C  L  P  S  Q  S  K  R  T  R  P   1282

4021  caggcagaagaggacctgcaggagccaaagggagacctggcagaatcctaagatgttagt  4080
1283   R  Q  K  R  T  C  R  S  Q  R  E  T  W  Q  N  P  K  M  L  V   1302

4081  tgctcattgtacatctgtaagaccagaatgtgaaaacaagtcacagaacaagatgctgct  4140
1303   A  H  C  T  S  V  R  P  E  C  E  N  K  S  Q  N  K  M  L  L   1322

4141  gttgggaccttggaccaagatttcagagcccatgagatccagagagcagggccgtccaat  4200
1323   L  G  P  W  T  K  I  S  E  P  M  R  S  R  E  Q  G  R  P  M   1342

4201  gatttccacccagtagagcaccccgacaattctgaggcttcatcgggagctagagccagc  4260
1343   I  S  T  Q  *                                                1346
```

FIG.3G

```
4261   taacatttcctcgtttcaagactgcctttgatttgccccttgatgccgtccgtgtatttc   4320
4321   ggatttaaggtcctgcgttctcaacctggaaccaattctgccatacctagttccacttct   4380
4381   caaactggagcatcctcctttatgtatttatatgtatgttttatgtagtcctcctcctgt   4440
4441   acctattgtatatttttttctaacgtttaagcacatgctttttgtattatgcaatatata   4500
4501   acgggtgtgcagccatagcgacgctttgaaaagctccaagcctcaactgtaacctgcagc   4560

4561   aaacagataacattcctggcaagaagagacaagtctttttaaagtttactgatgcttag   4620
4621   atctgtgggcttctagtcctctgaaagtggttgttttcctatgcacagcgagctcagaaa   4680
4681   taaaaaccccattttgaaacatccaggatgtcccaatattaccatgatttttttcccccct   4720
4721   ttttgctaatccagtccaggttggaaagaagtctcctctgtgtcagattaagccctgtct   4780
4781   cttaatgatatggacaaatgagtgtgcctaaggccatgagatgtttcctaatgcagaagg   4840
4741   aatctgttgtacgtttttttgattgtactcttctatgctggaccgaattcatatgcagat   4900
4901   cgaagtgagtcctgttctttacagatggtattttgatagatactggagtttgtctgtgtt   4960
4961   atatctgtgccccttctttaagaacaatgttgcattatgttcctttggataaattgtgat   5020
5021   ttgacaactgatttaaataaacatatttgactac(A).
```

FIG.3H

```
                9                18               27               36               45               54
5' ATG GGC GCA GGC AGT TCC ACC GAG CAG CGG AGC CCC GAG CAG CCG GCG GGG AGC
   --- --- --- --- --- --- --- --- --- --- --- --- --- --- --- --- --- ---
    M   G   A   G   S   S   T   E   Q   R   S   P   E   Q   P   A   G   S

               63               72               81               90               99              100
   GAC ACG CCG AGC GAG CTG GTG CTC AGT GGC CAT GGG CCC GCA GCT GAA GCC TCG
   --- --- --- --- --- --- --- --- --- --- --- --- --- --- --- --- --- ---
    D   T   P   S   E   L   V   L   S   G   H   G   P   A   A   E   A   S

              117              126              135              144              153              162
   GGA GCA GCT GGA GAC CCC GCC GAC GCG GAC CCC GCC ACC AAG CTC CCA CAG AAG
   --- --- --- --- --- --- --- --- --- --- --- --- --- --- --- --- --- ---
    G   A   A   G   D   P   A   D   A   D   P   A   T   K   L   P   Q   K

              171              180              189              198              207              216
   AAT GGC CAG CTG TCT TCT GTC AAC GGC GTA GCT GAA CAA GGA GAT GTC CAT GTC
   --- --- --- --- --- --- --- --- --- --- --- --- --- --- --- --- --- ---
    N   G   Q   L   S   S   V   N   G   V   A   E   Q   G   D   V   H   V

              225              234              243              252              261              270
   CAA GAG GAA AAC CAG GAG GGG CAG GAG GAA GAA GTC GTT GAT GAG GAT GTT GGA
   --- --- --- --- --- --- --- --- --- --- --- --- --- --- --- --- --- ---
    Q   E   E   N   Q   E   G   Q   E   E   E   V   V   D   E   D   V   G

              279              288              297              306              315              324
   CAG CGA GAG TCA GAA GAT GTG AGA GAA AAA GAC CGA GTT GAA GAA ATG GCG GCC
   --- --- --- --- --- --- --- --- --- --- --- --- --- --- --- --- --- ---
    Q   R   E   S   E   D   V   R   E   L   D   R   V   E   E   M   A   A

              333              342              351              360              369              378
   AAC TCC ACA GCT GTT GAA GAT ATC ACA AAG GAT GGG CAG GAG GAG ACA TCA GAA
   --- --- --- --- --- --- --- --- --- --- --- --- --- --- --- --- --- ---
    N   S   T   A   V   E   D   I   T   K   D   G   Q   E   E   T   S   E

              387              396              405              414              423              432
   ATA ATT GAA CAG ATC CCT GCT TCA GAA AAC AAT GTG GAA GAA ATG GTA CAG CCT
   --- --- --- --- --- --- --- --- --- --- --- --- --- --- --- --- --- ---
    I   I   E   Q   I   P   A   S   E   N   N   V   E   E   M   V   Q   P

              441              450              459              468              477              486
   GCT GAG TCC CAG GCT AAT GAT GTT GGC TTC AAG AAA GTA TTT AAA TTT GTT GGT
   --- --- --- --- --- --- --- --- --- --- --- --- --- --- --- --- --- ---
    A   E   S   Q   A   N   D   V   G   F   K   K   V   F   K   F   V   G

              495              504              513              522              531              540
   TTT AAA TTC ACG GTG AAG AAG GAT AAA AAT GAA AAG TCA GAT ACT GTC CAA CTA
   --- --- --- --- --- --- --- --- --- --- --- --- --- --- --- --- --- ---
    F   K   F   T   V   K   K   D   K   N   E   K   S   D   T   V   Q   L

              549              558              567              576              585              594
   CTC ACT GTC AAG AAG GAT GAA GGC GAA GGG GCA GAA GCC TCT GTC GGA GCT GGA
   --- --- --- --- --- --- --- --- --- --- --- --- --- --- --- --- --- ---
    L   T   V   K   K   D   E   G   E   G   A   E   A   S   V   G   A   G
```

FIG. 11A

```
        603         612         621         630         639         648
GAC CAC CAG GAG CCC AGT GTG GAG ACT GCC GTC GGA GAG TCA GCA TCC AAA GAA
--- --- --- --- --- --- --- --- --- --- --- --- --- --- --- --- --- ---
 D   H   Q   E   P   S   V   E   T   A   V   G   E   S   A   S   K   E

        657         666         675         684         693         702
AGT GAG CTG AAG CAA TCC ACA GAG AAG CAA GAA GGC ACC CTG AAG CAA GAA CAG
--- --- --- --- --- --- --- --- --- --- --- --- --- --- --- --- --- ---
 S   E   L   K   Q   S   T   E   K   Q   E   G   T   L   K   Q   E   Q

        711         720         729         738         747         756
AGC AGC ACA GAA ATC CCC CTT CAA GCC GAA TCT GAT CAA GCG GCT GAG GAA GAA
--- --- --- --- --- --- --- --- --- --- --- --- --- --- --- --- --- ---
 S   S   T   E   I   P   L   Q   A   E   S   D   Q   A   A   E   E   E

        765         774         783         792         801         810
GCC AAA GAT GAA GGA GAA GAA AAA CAA GAG AAA GAG CCC ACC AAG TCC CCA GAA
--- --- --- --- --- --- --- --- --- --- --- --- --- --- --- --- --- ---
 A   K   D   E   G   E   E   K   Q   E   K   E   P   T   K   S   P   E

        819         828         837         846         855         864
TCC CCG AGC AGC CCA GTC AAC AGT GAG ACA ACA TCT TCC TTC AAG AAG TTC TTC
--- --- --- --- --- --- --- --- --- --- --- --- --- --- --- --- --- ---
 S   P   S   S   P   V   N   S   E   T   T   S   S   F   K   K   F   F

        873         882         891         900         909         918
ACT CAC GGT TGG GCC GGC TGG CGC AAG AAG ACC AGC TTC AAG AAA TCA AAA GAG
--- --- --- --- --- --- --- --- --- --- --- --- --- --- --- --- --- ---
 T   H   G   W   A   G   W   R   K   K   T   S   F   K   K   S   K   E

        927         936         945         954         963         972
GAT GAT CTG GAA ACT GCC GAG AAG AGA AAG GAG CAA GAG GCA GAA AAA GTA GAC
--- --- --- --- --- --- --- --- --- --- --- --- --- --- --- --- --- ---
 D   D   L   E   T   A   E   K   R   K   E   Q   E   A   E   K   V   D

        981         990         999        1008        1017        1026
GAG GAA GAA AAG GAA AAG ACA GAG CCA GCC TCG GAG GAG CAG GAG CCG GCA GAA
--- --- --- --- --- --- --- --- --- --- --- --- --- --- --- --- --- ---
 E   E   E   K   E   K   T   E   P   A   S   E   E   Q   E   P   A   E

       1035        1044        1053        1062        1071        1080
GAC ACA GAC CAG GCC AGG TTG TCA GCA GAC TAC GAG AAG GTG GAG CTG CCT TTG
--- --- --- --- --- --- --- --- --- --- --- --- --- --- --- --- --- ---
 D   T   D   Q   A   R   L   S   A   D   Y   E   K   V   E   L   P   L

       1089        1098        1107        1116        1125        1134
GAA GAC CAG GTT GGT GAC CTG GAG GCA TCG TCA GAG GAG AAG TGT GCT CCT TTG
--- --- --- --- --- --- --- --- --- --- --- --- --- --- --- --- --- ---
 E   D   Q   V   G   D   L   E   A   S   S   E   E   K   C   A   P   L

       1143        1152        1161        1170        1179        1188
GCA ACG GAA GTG TTT GAT GAG AAG ATG GAA GCC CAC CAA GAA GTT GTT GCA GAG
--- --- --- --- --- --- --- --- --- --- --- --- --- --- --- --- --- ---
 A   T   E   V   F   D   E   K   M   E   A   H   Q   E   V   V   A   E
```

FIG.11B

```
        1197        1206        1215        1224        1233        1242
GTC CAC GTG AGC ACC GTG GAG AAG ACA GAG GAG GAG CAG GGA GGA GGA GGA GAG
--- --- --- --- --- --- --- --- --- --- --- --- --- --- --- --- --- ---
 V   H   V   S   T   V   E   K   T   E   E   E   Q   G   G   G   G   E

        1251        1260        1269        1278        1287        1296
GCT GAA GGG GGC GTG GTG GTA GAA GGA ACA GGA GAA TCC TTG CCC CCT GAG AAA
--- --- --- --- --- --- --- --- --- --- --- --- --- --- --- --- --- ---
 A   E   G   G   V   V   V   E   G   T   G   E   S   L   P   P   E   K

        1305        1314        1323        1332        1341        1350
CTG GCT GAG CCC CAG GAG GTC CCC CAG GAA GCT GAG CCT GCT GAG GAG CTG ATG
--- --- --- --- --- --- --- --- --- --- --- --- --- --- --- --- --- ---
 L   A   E   P   Q   E   V   P   Q   E   A   E   P   A   E   E   L   M

        1359        1368        1377        1386        1395        1404
AAG AGC AGA GAG ATG TGT GTC TCT GGA GGA GAC CAC ACT CAA CTG ACA GAC CTA
--- --- --- --- --- --- --- --- --- --- --- --- --- --- --- --- --- ---
 K   S   R   E   M   C   V   S   G   G   D   H   T   Q   L   T   D   L

        1413        1422        1431        1440        1449        1458
AGT CCT GAA GAG AAG ACG CTG CCC AAA CAC CCA GAA GGC ATT GTC AGT GAG GTG
--- --- --- --- --- --- --- --- --- --- --- --- --- --- --- --- --- ---
 S   P   E   E   K   T   L   P   K   H   P   E   G   I   V   S   E   V

        1467        1476        1485        1494        1503        1512
GAG ATG CTG TCC TCT CAG GAA AGA ATC AAG GTA CAG GGA AGT CCC TTG AAG AAA
--- --- --- --- --- --- --- --- --- --- --- --- --- --- --- --- --- ---
 E   M   L   S   S   Q   E   R   I   K   V   Q   G   S   P   L   K   K

        1521        1530        1539        1548        1557        1566
CTC TTC AGT AGC TCA GGC TTA AAG AAG CTG TCT GGG AAG AAG CAG AAG GGG AAA
--- --- --- --- --- --- --- --- --- --- --- --- --- --- --- --- --- ---
 L   F   S   S   S   G   L   K   K   L   S   G   K   K   Q   K   G   K

        1575        1584        1593        1602        1611        1620
CGA GGA GGT GGG GGA GAC GAA GAG CCT GGA GAA TAC CAA CAC ATT CAC ACC GAA
--- --- --- --- --- --- --- --- --- --- --- --- --- --- --- --- --- ---
 R   G   G   G   G   D   E   E   P   G   E   Y   Q   H   I   H   T   E

        1629        1638        1647        1656        1665        1674
TCC CCA GAG AGT GCT GAT GAG CAG AAG GGA GAG AGC TCT GCG TCG TCC CCC GAG
--- --- --- --- --- --- --- --- --- --- --- --- --- --- --- --- --- ---
 S   P   E   S   A   D   E   Q   K   G   E   S   S   A   S   S   P   E

        1683        1692        1701        1710        1719        1728
GAG CCT GAG GAG ACC ACG TGT CTG GAG AAA GGG CCG CTG GAA GCA CCC CAG GAT
--- --- --- --- --- --- --- --- --- --- --- --- --- --- --- --- --- ---
 E   P   E   E   T   T   C   L   E   K   G   P   L   E   A   P   Q   D

        1737        1746        1755        1764        1773        1782
GGG GAA GCT GAG GAA GGA ACT ACT TCC GAT GGA GAG AAG AAG AGA GAA GGG ATC
--- --- --- --- --- --- --- --- --- --- --- --- --- --- --- --- --- ---
 G   E   A   E   E   G   T   T   S   D   G   E   K   K   R   E   G   I
```

FIG. 11C

```
     1791      1800      1809      1818      1827      1836
ACT CCC TGG GCA TCC TTC AAA AAG ATG GTG ACA CCC AAG AAA CGG GTC CGA AGA
--- --- --- --- --- --- --- --- --- --- --- --- --- --- --- --- --- ---
 T   P   W   A   S   F   K   K   M   V   T   P   K   K   R   V   R   R

     1845      1854      1863      1872      1881      1890
CCT TCT GAG AGT GAC AAG GAG GAA GAG CTG GAG AAG GTC AAG AGC GCC ACC TTG
--- --- --- --- --- --- --- --- --- --- --- --- --- --- --- --- --- ---
 P   S   F   S   D   K   E   E   E   L   E   K   V   K   S   A   T   L

     1899      1908      1917      1926      1935      1944
TCC TCC ACT GAT AGC ACA GTG TCA GAA ATG CAA GAT GAA GTC AAA ACT GTT GGT
--- --- --- --- --- --- --- --- --- --- --- --- --- --- --- --- --- ---
 S   S   T   D   S   T   V   S   E   M   Q   D   E   V   K   T   V   G

     1953      1962      1971      1980      1589      1998
GAG GAA CAA AAG CCA GAG GAA CCA AAG CGT AGG GTG GAT ACT TCA GTG TCT TGG
--- --- --- --- --- --- --- --- --- --- --- --- --- --- --- --- --- ---
 E   E   Q   K   P   E   E   P   K   R   R   V   D   T   S   V   S   W

     2007      2016      2025      2034      2043      2052
GAA GCA CTG ATT TGT GTC GGA TCA TCC AAG AAG AGA GCA AGG AAG GCA TCC TCT
--- --- --- --- --- --- --- --- --- --- --- --- --- --- --- --- --- ---
 E   A   L   I   C   V   G   S   S   K   K   R   A   R   K   A   S   S

     2061      2070      2079      2088      2097      2106
TCA GAT GAT GAA GGA GGG CCA AGG ACA CTG GGA GGG GAC AGT CAC AGA GCA GAG
--- --- --- --- --- --- --- --- --- --- --- --- --- --- --- --- --- ---
 S   D   D   E   G   G   P   R   T   L   G   G   D   S   H   R   A   E

     2115      2124      2133      2142      2151      2160
GAG GCC AGC AAA GAC AAA GAA GCC GGA ACA GAC GCT GTT CCT GCC AGC ACC CAG
--- --- --- --- --- --- --- --- --- --- --- --- --- --- --- --- --- ---
 E   A   S   K   D   K   E   A   G   T   D   A   V   P   A   S   T   Q

  2169      2178      2187      2196      2205      2114
GAG CAG GAC CAA GCG CAA GGA AGT TCC TCA CCC GAG CCA GCG GGA AGC CTT TCC
--- --- --- --- --- --- --- --- --- --- --- --- --- --- --- --- --- ---
 E   Q   D   Q   A   Q   G   S   S   S   P   E   P   A   G   S   P   S

     2223      2232      2241      2250      2259      2268
GAA GGG GAA GGT GTC TCC ACT TGG GAG TCA TTT AAA AGA TTA GTC ACT CCA AGA
--- --- --- --- --- --- --- --- --- --- --- --- --- --- --- --- --- ---
 E   G   E   G   V   S   T   W   E   S   F   K   R   L   V   T   P   R

     2277      2286      2295      2304      2313      2322
AAA AAA TCC AAG TCA AAA CTG GAA GAG AAA GCC GAA GAC TCT AGT GTA GAG CAG
--- --- --- --- --- --- --- --- --- --- --- --- --- --- --- --- --- ---
 K   K   S   K   S   K   L   E   E   K   A   E   D   S   S   V   E   Q

     2331      2340      2349      2358      2367      2376
TTG TCC ACT GAG ATC GAA CCG AGT AGA GAA GAA TCT TGG GTT TCC ATT AAG AAA
--- --- --- --- --- --- --- --- --- --- --- --- --- --- --- --- --- ---
 L   S   T   E   I   E   P   S   R   E   E   S   W   V   S   I   K   K
```

FIG.11D

```
     2385        2394        2403        2412        2421        2430
TTC ATC CCC GGA CGG CGG AAG AAA AGG GCA GAC GGG AAG CAA GAA CAA GCC ACT
--- --- --- --- --- --- --- --- --- --- --- --- --- --- --- --- --- ---
 F   I   P   G   R   R   K   K   R   A   D   G   K   Q   E   Q   A   T

     2439        2448        2457        2466        2475        2484
GTG GAA GAC TCA GGG CCA GTG GAG ATA AAT GAG GAC GAC CCT AAT GTC CCA GCC
--- --- --- --- --- --- --- --- --- --- --- --- --- --- --- --- --- ---
 V   E   D   S   G   P   V   E   I   N   E   D   D   P   N   V   P   A

     2493        2502        2511        2520        2529        2538
GTC GTG CCT CTG TCT GAG TAT AAT GCA GTG GAG AGG GAG AAG ATG GAA GCC CAG
--- --- --- --- --- --- --- --- --- --- --- --- --- --- --- --- --- ---
 V   V   P   L   S   E   Y   N   A   V   E   R   E   K   M   E   A   Q

     2547        2556        2565        2574        2583        2592
GGG AAT ACG GAG CTG CCC CAG CTG CTG GGG GCT GTG TAC GTG TCC GAG GAG CTC
--- --- --- --- --- --- --- --- --- --- --- --- --- --- --- --- --- ---
 G   N   T   E   L   P   Q   L   L   G   A   V   Y   V   S   E   E   L

     2601        2610        2619        2628        2637        2646
AGT AAG ACT CTG GTC CAC ACT GTG AGT GTC GCA GTC ATT GAT GGG ACC AGG GCA
--- --- --- --- --- --- --- --- --- --- --- --- --- --- --- --- --- ---
 S   K   T   L   V   H   T   V   S   V   A   V   I   D   G   T   R   A

     2655        2664        2673        2682        2691        2700
GTC ACC AGT GTC GAA GAG CGG TCT CCT TCG TGG ATA TCC GCT TCC GTA ACA GAA
--- --- --- --- --- --- --- --- --- --- --- --- --- --- --- --- --- ---
 V   T   S   V   E   E   R   S   P   S   W   I   S   A   S   V   T   E

     2790        2718        2727        2736        2745        2754
CCT CTT GAA CAC ACA GCG GGA GAA GCC ATG CCA CCT GTT GAA GAG GTC ACT GAA
--- --- --- --- --- --- --- --- --- --- --- --- --- --- --- --- --- ---
 P   L   R   H   T   A   G   E   A   M   P   P   V   E   E   V   T   E

     2763        2772        2781        2790        2799        2808
AAA GAC ATC ATT GCA GAA GAA ACT CCT GTG CTC ACC CAG ACG TTA CCA GAG GGT
--- --- --- --- --- --- --- --- --- --- --- --- --- --- --- --- --- ---
 K   D   I   I   A   E   E   T   P   V   L   T   Q   T   L   P   E   G

     2817        2826        2835        2844        2853        2862
AAA GAT GCC CAT GAC GAC ATG GTC ACC AGT GAA GTG GAT TTC ACC TCA GAA GCT
--- --- --- --- --- --- --- --- --- --- --- --- --- --- --- --- --- ---
 K   D   A   H   D   D   M   V   T   S   E   V   D   F   T   S   E   A

     2871        2880        2889        2898        2907        2916
GTG ACA GCC ACA GAG ACC TCA GAG GCT CTC CGT ACT GAA GAA GTT ACC GAA GCA
--- --- --- --- --- --- --- --- --- --- --- --- --- --- --- --- --- ---
 V   T   A   T   E   T   S   E   A   L   R   T   E   E   V   T   E   A

     2925        2934        2943        2952        2961        2970
TCG GGG GCC GAA GAG ACC ACA GAC ATG GTG TCC GCA GTT TCC CAG CTG ACT GAC
--- --- --- --- --- --- --- --- --- --- --- --- --- --- --- --- --- ---
 S   G   A   E   E   T   T   D   M   V   S   A   V   S   Q   L   T   D
```

FIG.11E

```
        2979             2988             2997             3006             3015             3024
TCC CCA GAC ACC ACA GAG GAA GCC ACC CCA GTT CAG GAG GTA GAG AGT GGT GTG
--- --- --- --- --- --- --- --- --- --- --- --- --- --- --- --- --- ---
 S   P   D   T   T   E   E   A   T   P   V   Q   E   V   E   S   G   V

        3033             3042             3051             3060             3069             3078
CTA GAT ACA GAA GAA GAG GAG CGC CAG ACG CAG GCC ATC CTC CAA GCC GTT GCA
--- --- --- --- --- --- --- --- --- --- --- --- --- --- --- --- --- ---
 L   D   T   E   E   E   E   R   Q   T   Q   A   I   L   Q   A   V   A

        3087             3096             3105             3114             3123             3132
GAC AAG GTG AAA GAG GAG TCC CAG GTG CCT GCA ACC CAG ACT GTG CAG AGA ACG
--- --- --- --- --- --- --- --- --- --- --- --- --- --- --- --- --- ---
 D   K   V   K   E   E   S   Q   V   P   A   T   Q   T   V   Q   R   T

        3141             3150             3159             3168             3177             3186
GGG TCA AAA GCA CTG GAG AAG GTT GAG GAG GTA GAG GAG GAC TCC GAA GTG CTG
--- --- --- --- --- --- --- --- --- --- --- --- --- --- --- --- --- ---
 G   S   K   A   L   E   K   V   E   E   V   E   E   D   S   E   V   L

        3195             3204             3213             3222             3231             3240
GCT TCG GAG AAA GAG AAG GAC GTT ATG CCG AAA GGA CCC GTG CAG GAA GCT GGA
--- --- --- --- --- --- --- --- --- --- --- --- --- --- --- --- --- ---
 A   S   E   K   E   K   D   V   M   P   K   G   P   V   Q   E   A   G

        3195             3258             3267             3276             3285             3294
GCT GAG CAT CTT GCA CAG GGC TCT GAG ACT GGA CAG GCT ACT CCA GAG AGC CTT
--- --- --- --- --- --- --- --- --- --- --- --- --- --- --- --- --- ---
 A   E   H   L   A   Q   G   S   E   T   G   Q   A   T   P   E   S   L

        3303             3312             3321             3330             3339             3348
GAA GTT CCT GAA GTC ACG GCA GAT GTA GAC CAT GTC GCC ACG TGC CAG GTT ATC
--- --- --- --- --- --- --- --- --- --- --- --- --- --- --- --- --- ---
 E   V   P   E   V   T   A   D   V   D   H   V   A   T   C   Q   V   I

        3357             3366             3375             3384             3393             3402
AAG CTC CAG CAG CTG ATG GAA CAG GCC GTG GCC CCT GAG TCA TCC GAA ACC TTG
--- --- --- --- --- --- --- --- --- --- --- --- --- --- --- --- --- ---
 K   L   Q   Q   L   M   E   Q   A   V   A   P   E   S   S   E   T   L

        3411             3420             3429             3438             3447             3456
ACA GAC AGT GAG ACA AAT GGA AGC ACT CCC TTA GCA GAT TCA GAC ACT GCA GAT
--- --- --- --- --- --- --- --- --- --- --- --- --- --- --- --- --- ---
 T   D   S   E   T   N   G   S   T   P   L   A   D   S   D   T   A   D

        3465             3474             3483             3492             3501             3510
GGG ACA CAG CAA GAT GAA ACC ATT GAC AGC CAG GAC AGT AAA GCC ACT GCA GCT
--- --- --- --- --- --- --- --- --- --- --- --- --- --- --- --- --- ---
 G   T   Q   Q   D   E   T   I   D   S   Q   D   S   K   A   T   A   A

        3519             3528             3537             3546             3555             3564
GTC AGG CAG TCA CAG GTC ACA GAA GAA GAG GCG GCT ACT GCT CAG AAA GAG GAG
--- --- --- --- --- --- --- --- --- --- --- --- --- --- --- --- --- ---
 V   R   Q   S   Q   V   T   E   E   E   A   A   T   A   Q   K   E   E
```

FIG.11F

```
        3573        3582        3591        3600        3609        3618
CCT TCG ACA CTA CCT AAT AAT GTT CCA GCC CAG GAA GAA CAT GGG GAA GAA CCA
--- --- --- --- --- --- --- --- --- --- --- --- --- --- --- --- --- ---
 P   S   T   L   P   N   N   V   P   A   Q   E   E   H   G   E   E   P

        3627        3636        3645        3654        3663        3672
GGA AGA GAT GTT CTT GAA CCT ACA CAG CAA GAG CTT ACT GCT GCA GCC GTG CCC
--- --- --- --- --- --- --- --- --- --- --- --- --- --- --- --- --- ---
 G   R   D   V   L   E   P   T   Q   Q   E   L   T   A   A   A   V   P

        3681        3690        3699        3708        3717        3726
GTT CTG GCA AAG ACT GAG GTG GGT CAA GAG GGT GAG GTT GAC TGG TTG GAT GGA
--- --- --- --- --- --- --- --- --- --- --- --- --- --- --- --- --- ---
 V   L   A   K   T   E   V   G   Q   E   G   E   V   D   W   L   D   G

        3735        3744        3753        3762        3771        3780
GAA AAA GTC AAA GAA GAA CAG GAG GTG TTT GTA CAC TCT GGA CCC AAC AGT CAA
--- --- --- --- --- --- --- --- --- --- --- --- --- --- --- --- --- ---
 E   K   V   K   E   E   Q   E   V   F   V   H   S   G   P   N   S   Q

        3789        3798        3807        3816        3825        3834
AAG GCT GCT GAT GTG ACA TAT GAC AGT GAA GTG ATG GGA GTG GCC GGG TGT CAG
--- --- --- --- --- --- --- --- --- --- --- --- --- --- --- --- --- ---
 K   A   A   D   V   T   Y   D   S   E   V   M   G   V   A   G   C   Q

        3843        3852        3861        3870        3879        3888
GAA AAG GAG AGT ACT GAA GTG CAG AGT CTT AGC CTG GAG GAG GGA GAG ATG GAA
--- --- --- --- --- --- --- --- --- --- --- --- --- --- --- --- --- ---
 E   K   E   S   T   E   V   Q   S   L   S   L   E   E   G   E   M   E

        3897        3906        3915        3924        3933        3942
ACT GAC GTT GAA AAG GAG AAA AGG GAG ACA AAG CCA GAG CAA GTG AGT GAA GAA
--- --- --- --- --- --- --- --- --- --- --- --- --- --- --- --- --- ---
 T   D   V   E   K   E   K   R   E   T   K   P   E   Q   V   S   E   E

        3951        3960        3969        3978        3987        3996
GGT GAG CAG GAA ACA GCC GCT CCT GAG CAT GAA GGA ACC TAC GGG AAG CCA GTC
--- --- --- --- --- --- --- --- --- --- --- --- --- --- --- --- --- ---
 G   E   Q   E   T   A   A   P   E   H   E   G   T   Y   G   K   P   V

        4005        4014        4023        4032        4041        4050
CTG ACA CTT GAC ATG CCC AGC TCA GAG AGG GGG AAG GCA CTG GGA AGC CTT GGA
--- --- --- --- --- --- --- --- --- --- --- --- --- --- --- --- --- ---
 L   T   L   D   M   P   S   S   E   R   G   K   A   L   G   S   L   G

        4059        4068        4077        4086        4095        4104
GGA AGC CCT TCT CTC CCA GAC CAA GAC AAA GCA GGT TGC ATA GAG GTT CAA GTT
--- --- --- --- --- --- --- --- --- --- --- --- --- --- --- --- --- ---
 G   S   P   S   L   P   D   Q   D   K   A   G   C   I   E   V   Q   V

        4113        4122        4131        4140        4149        4158
CAA AGC CTG GAC ACA ACA GTC ACT CAA ACA GCA GAA GCT GTG GAA AAG GTC ATA
--- --- --- --- --- --- --- --- --- --- --- --- --- --- --- --- --- ---
 Q   S   L   D   T   T   V   T   Q   T   A   E   A   V   E   K   V   I
```

FIG.11G

```
      4167        4176        4185        4194        4203        4212
GAA ACG GTT GTG ATT TCA GAG ACA GGT GAA AGT CCA GAG TGT GTA GGT GAC CAC
--- --- --- --- --- --- --- --- --- --- --- --- --- --- --- --- --- ---
 E   T   V   V   I   S   E   T   G   E   S   P   E   C   V   G   A   H

      4221        4230        4239        4248        4257        4266
TTA TTA CCA GCT GAG AAG TCC TCT GCA ACG GGT GGC CAC TGG ACT CTT CAG CAT
--- --- --- --- --- --- --- --- --- --- --- --- --- --- --- --- --- ---
 L   L   P   A   E   K   S   S   A   T   G   G   H   W   T   L   Q   H

      4275        4284        4293        4902        4311        4320
GCA GAG GAC ACG GTA CCC CTG GGG CCT GAG TCT CAG GCA GAA TCC ATC CCA ATC
--- --- --- --- --- --- --- --- --- --- --- --- --- --- --- --- --- ---
 A   E   D   T   V   P   L   G   P   E   S   Q   A   E   S   I   P   I

      4437        4446        4455        4464        4473        4482
GAT GCT GAC GGC AAG GAG AGT ACA GCA ATC GAA AAA GTC CTC AAG GCT GAA CCT
--- --- --- --- --- --- --- --- --- --- --- --- --- --- --- --- --- ---
 D   A   D   G   K   E   S   T   A   I   E   K   V   L   K   A   E   P

      4491        4500        4509        4518        4527        4536
GAG ATC CTG GAA CTT GAG AGT AAG AGC AAC AAG ATT GTG CTG AAC GTC ATT CAG
--- --- --- --- --- --- --- --- --- --- --- --- --- --- --- --- --- ---
 E   I   L   E   L   E   S   K   S   N   K   I   V   L   N   V   I   Q

      4545        4554        4563        4572        4581        4590
ACA GCC GTT GAC CAG TTC GCA CGT ACA GAA ACA GCC CCC GAA ACT CAT GCT TAT
--- --- --- --- --- --- --- --- --- --- --- --- --- --- --- --- --- ---
 T   A   V   D   Q   F   A   R   T   E   T   A   P   E   T   H   A   Y

      4599        4608        4617        4626        4635        4644
GAT TCA CAG ACC CAG GTT CCT GCA TGC AGG CTT GAC AGC AGG GAG CCC AAC AGA
--- --- --- --- --- --- --- --- --- --- --- --- --- --- --- --- --- ---
 D   S   Q   T   Q   V   P   A   C   R   L   D   S   R   E   P   N   R

      4653        4662        4671        4680        4689        4698
TGC TGG ACA AAA ATG AAA GAT GCC AAG ATG AAA CAC CCA GTG CCG CAG CCC AGA
--- --- --- --- --- --- --- --- --- --- --- --- --- --- --- --- --- ---
 C   W   T   K   M   K   D   A   K   M   K   H   P   V   P   Q   P   R

      4707        4716        4725        4734        4743        4752
GAG GAC TTG CAA GTC CTG ACC GTT CTG GAG GCA TGG GCT CAG CCT CGG AAA TGC
--- --- --- --- --- --- --- --- --- --- --- --- --- --- --- --- --- ---
 E   D   L   Q   V   L   T   V   L   E   A   W   A   Q   P   R   K   C

      4761        4770        4779        4788        4797        4806
TGG CCG CGC TTG CAG TTG AAA GCG CCG GTG TCA AAG TAA GCA TTG AGA ACC TGC
--- --- --- --- --- --- --- --- --- --- --- --- --- --- --- --- --- ---
 L   P   R   L   Q   L   K   A   P   V   S   K   *

      4815        4824        4833        4842        4851        4860
CTC CTC AAC CCA AAG ATC CAA AAG GAG CAT GCT GCT GAT GGC CCT CAG CTC CAA
--- --- --- --- --- --- --- --- --- --- --- --- --- --- --- --- --- ---
```

FIG.11H

```
       4869      4878      4887      4896      4905      4914
AGC TTA GCC CAG GCA GAG GCC AGT GCC TCT GGA AAC CTA ACC AAA GAA TCC CCA
--- --- --- --- --- --- --- --- --- --- --- --- --- --- --- --- --- ---

       4923      4932      4941      4950      4959      4968
GAC ACC AAC GGA CCA AAG ATC ACC GAG GAG GGC GAT CCC CCA AAA GTT GAG GTC
--- --- --- --- --- --- --- --- --- --- --- --- --- --- --- --- --- ---

       4977      4986      4995      5004      5013      5022
CAG GAA GAA GAA ATG TCT ACC AAG TCA GTC AAA GAG AAC AAG GCC CAG GCA GAA
--- --- --- --- --- --- --- --- --- --- --- --- --- --- --- --- --- ---

       5031      5040      5049      5058      5067      5076
GAG GAC CTG CAG GAG CCA AAG GGA GAC CTG GCA GAA TCC TAA GAT GTT AGT TGC
--- --- --- --- --- --- --- --- --- --- --- --- --- --- --- --- --- ---

       5085      5094      5103      5112      5121      5130
TCA TTG TAC ATC TGT AAG ACC AGA ATG TGA AAA CAA GTC ACA GAA CAA GAT GCT
--- --- --- --- --- --- --- --- --- --- --- --- --- --- --- --- --- ---

       5139      5148      5157      5166      5175      5184
GCT GTT GGG ACC TTG AGA CCA AGA TTT CAG AGC CCA TGA GAT CCA GAG AGC AGG
--- --- --- --- --- --- --- --- --- --- --- --- --- --- --- --- --- ---

       5193
GCC GTC CAA TGA TTT C 3'
--- --- --- --- --- ---
```

FIG.11I

SSeCKS
13.2.2

220 KD —
116 —
97.4 —

FIG. 12

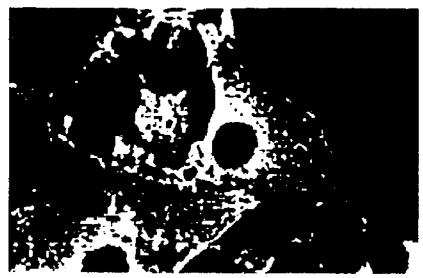
FIG.21A
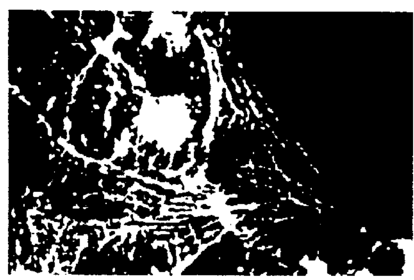
FIG.21B
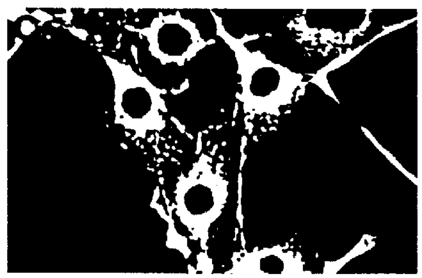
FIG.21C
FIG.21D
FIG.21E
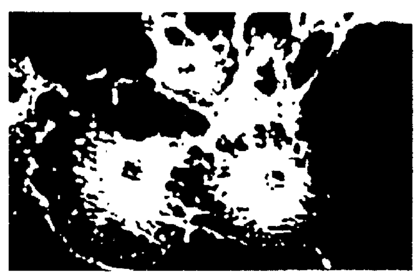
FIG.21F FIG.21G
FIG.21H
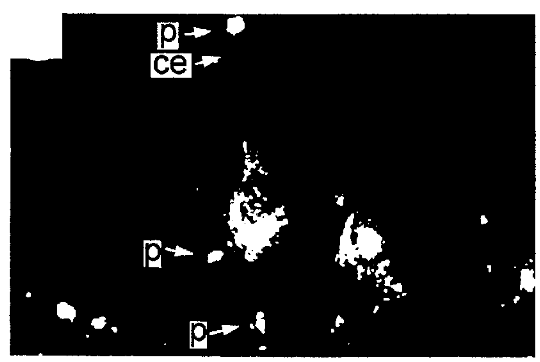
FIG.21I
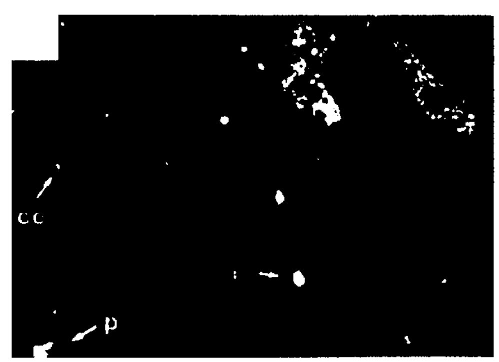
FIG.21J

| | | Myr. | Pal. |
|---|---|---|---|
| *src* | MGSSKSKPKD | + | - |
| yes | MGCIKSKEDK | + | + |
| SSeCKS | MGAGSSTEQR | + | ? |
| $G_{\alpha t}$ 1 | MGAGASAEEK | + | - |
| $G_{\alpha i}$ 1 | MGCTLSAEDK | + | + |
| GAP-43 | MLCCMRRTKQ | - | + |

Myrist. Consensus:
MGXXX $^{S}/_{T}$

FIG.26

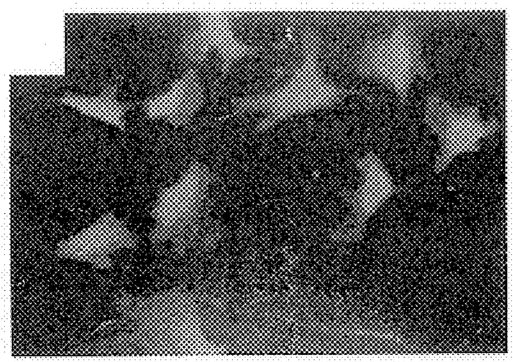
FIG.30A
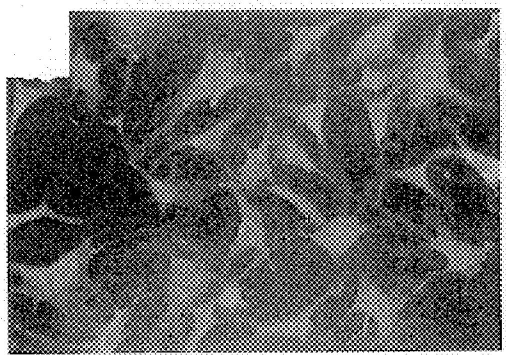
FIG.30B
FIG.30C
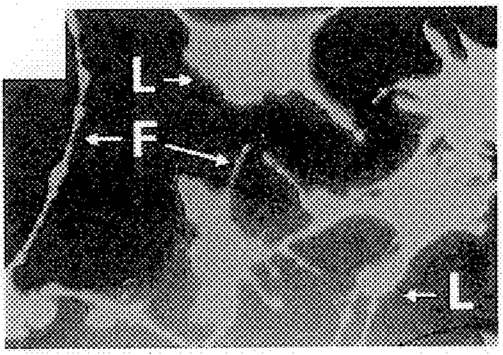
FIG.30D

FIG.31A
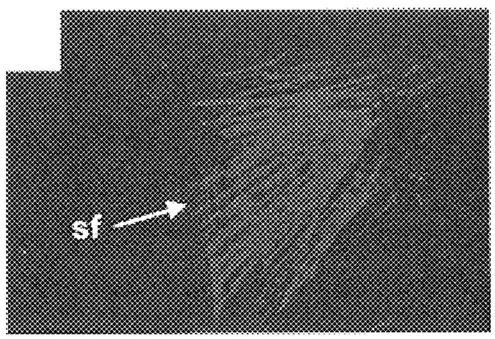
FIG.31B
FIG.31C
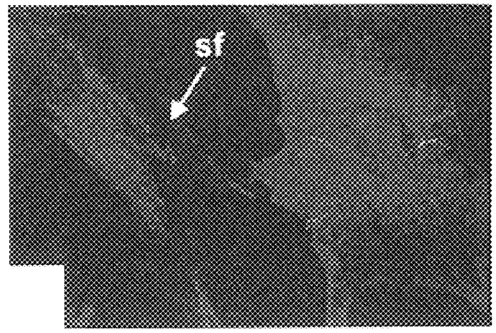
FIG.31D

Figure 32E:
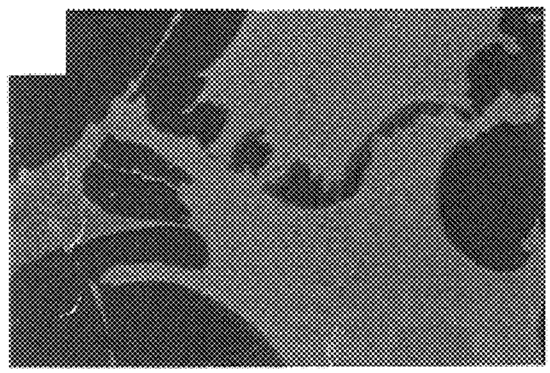
Figure 32F:
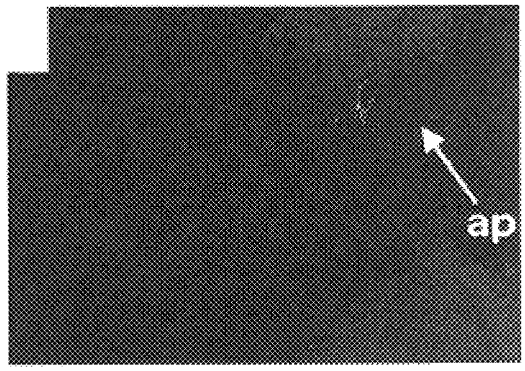
Figure 32G:
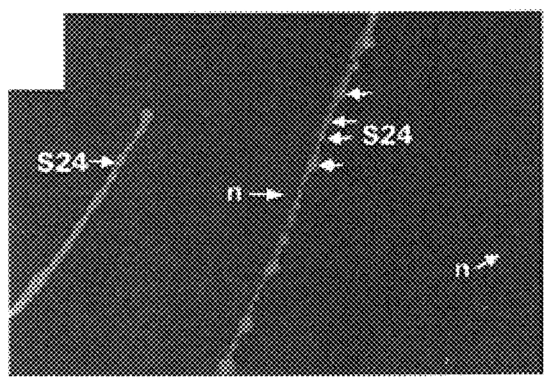
Figure 32H:
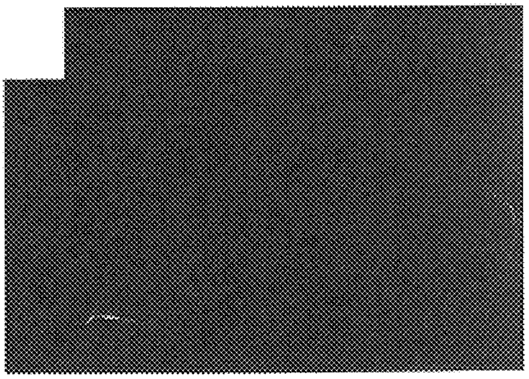

FIG.32A
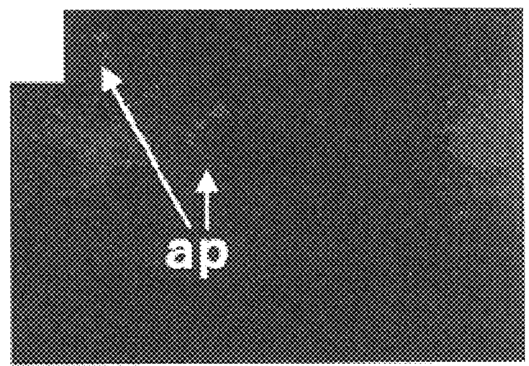
FIG.32B
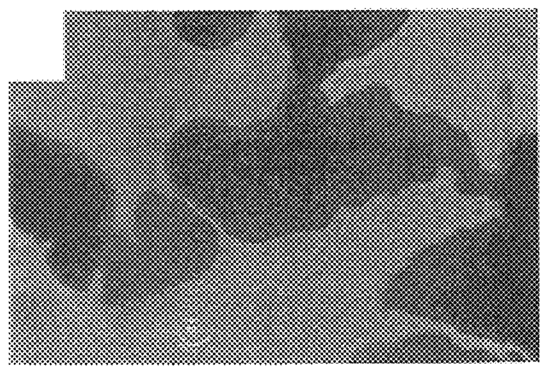
FIG.32C
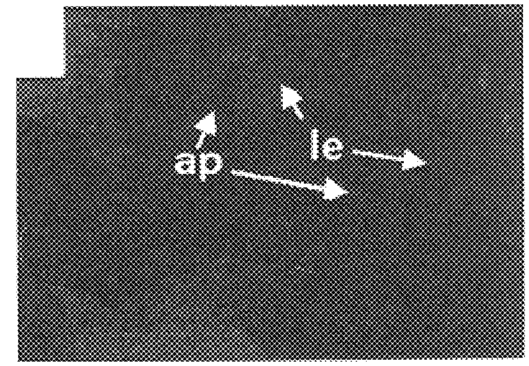
FIG.32D

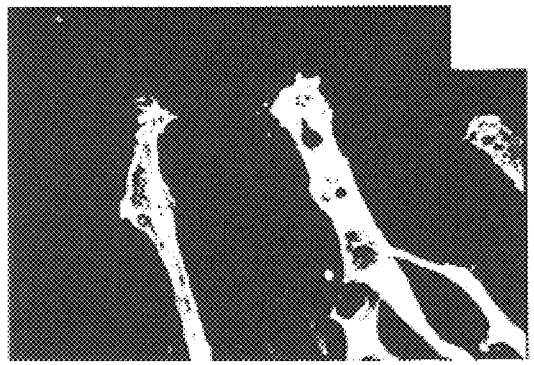
FIG.33E
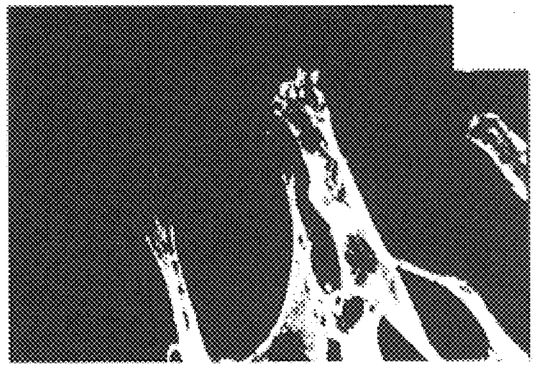
FIG.33F
FIG.33G
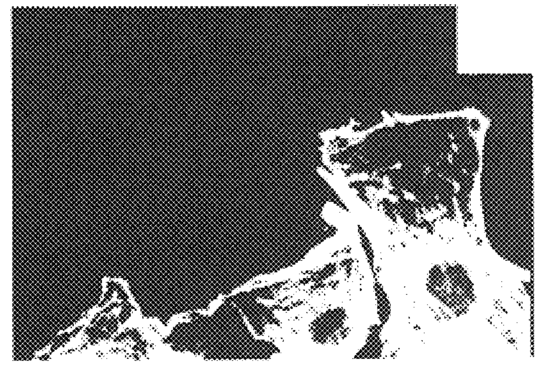
FIG.33H

SEQUENCE LISTING

```
(1) GENERAL INFORMATION:

   (iii) NUMBER OF SEQUENCES: 20


(2) INFORMATION FOR SEQ ID NO:1:

     (i) SEQUENCE CHARACTERISTICS:
          (A) LENGTH: 5074 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (iv) ANTI-SENSE: NO

     (v) FRAGMENT TYPE:

    (vi) ORIGINAL SOURCE:

    (xi) SEQUENCE DESCRIPTION: SEQ ID NO:1:

GGAAAAGACA GAGCCAGCCT CGGAGGAGCA GGAGCCGGCA GAAGACACAG ACCAGGCCAG     60

GTTGTCAGCA GACTACGAGA AGGTGGAGCT GCCTTTGGAA GACCAGGTTG GTGACCTGGA    120

GGCATCGTCA GAGGAGAAGT GTGCTCCTTT GGCAACGGAA GTGTTTGATG AGAAGATGGA    180

AGCCCACCAA GAAGTTGTTG CAGAGGTCCA CGTGAGCACC GTGGAGAAGA CAGAGGAGGA    240
```

-continued

```
GCAGGGAGGA GGAGGAGAGG CTGAAGGGGG CGTGGTGGTA GAAGGAACAG GAGAATCCTT    300
GCCCCCTGAG AAACTGGCTG AGCCCCAGGA GGTCCCCCAG GAAGCTGAGC CTGCTGAGGA    360
GCTGATGAAG AGCAGAGAGA TGTGTGTCTC TGGAGGAGAC CACACTCAAC TGACAGACCT    420
AAGTCCTGAA GAGAAGACGC TGCCCAAACA CCCAGAAGGC ATTGTCAGTG AGGTGGAGAT    480
GCTGTCCTCT CAGGAAAGAA TCAAGGTACA GGGAAGTCCC TTGAAGAAAC TCTTCAGTAG    540
CTCAGGCTTA AAGAAGCTGT CTGGGAAGAA GCAGAAGGGG AAACGAGGAG GTGGGGGAGA    600
CGAAGAGCCT GGAGAATACC AACACATTCA CACCGAATCC CCAGAGAGTG CTGATGAGCA    660
GAAGGGAGAG AGCTCTGCGT CGTCCCCCGA GGAGCCTGAG GAGACCACGT GTCTGGAGAA    720
AGGGCCGCTG GAAGCACCCA GGATGGGGAA GCTGAGGAAG GAACTACTTC GTGGAGAGAA    780
GAAGAGGAAG GATCACTCCC TGGGCATCCT TCAAAAAGAT GGTGACACCC AAGAAACGGT    840
CCGAAGACCT TCTGAGAGTG ACAAGGAGGA AGAGCTGGAG AAGGTCAAGA GCGCCACCTT    900
GTCCTCCACT GATAGCACAG TGTCAGAAAT GCAAGATGAA GTCAAAACTG TTGGTGAGGA    960
ACAAAAGCCA GAGGAACCAA AGCGTAGGGT GGATACTTCA GTGTCTTGGG AAGCACTGAT   1020
TTGTGTCGGA TCATCCAAGA AGAGAGCAAG GAAGGCATCC TCTTCAGATA TAAGAGGGCC   1080
AAGGACACTG GGAGGGGGAC AGTCACAGAG CAGAGGAGGC CAGCAAAGAC AAAGAAGCCG   1140
AACAGACGCT GTTCCTGCCA GCACCCAGGA GCAGGACCAA GCGCAAGGAA GTTCCTCACC   1200
CGAGCCAGCG GGAAGCCCTT CCGAAGGGGA AGGTGTCTCC ACTTGGGAGT CATTTAAAAG   1260
ATTAGTCACT CCAAGAAAAA AATCCAAGTC AAAACTGGAA GAGAAAGAAG CCGGAAGGAC   1320
TCTAGTTGTA GGAGCAGGTT GTCCACTGAG ATCGAACCGT GTAGAGAAGA ATCTTGGGTT   1380
TCCATTAAGA AATTCATCCC CGGACGGCGG AAGAAAAGGG CAGATGGGAA GGCAAGAACA   1440
AGCCACTGTG GAAGACTCAG GGCCAGTGGA GATAAATGAG GACGAGCCTG ATGTCCCAGC   1500
CGTCGTGCCT CTGTCTGAGT ATGATGCAGT GGAGAGGGAG AAGATGGAAG CCCAGGGGAA   1560
TGCGGAGCTG CCCAGCTGCT GGGGCTGTGT AGTGTCCGAG GAGCTCAGTA AGACTCTGGT   1620
CCACACTGTG AGTGTCGCAG TCATTGATGG GACCAGGGCA GTCACCAGTG TCGAAGAGCG   1680
GTCTCCTTCG TGGATATCCG CTTCCGTAAC AGAACCTCTT GAACACACAG CGGGAGAAGC   1740
CATGCCACCT GTTGAAGAGG TCACTGAAAA AGACATCATT GCAGAAGAAA CTCCTGTGCT   1800
CACCCAGACG TTACCAGAGG GTAAAGATGC CCATGACGAC ATGGTCACCA GTGAAGTGGA   1860
TTTCACCTCA GAAGCTGTGA CAGCCACAGA GACCTCAGAG GCTCTCCGTA CTGAAGAAGT   1920
TACCGAAGCA TCGGGGGCCG AAGAGACCAC AGACATGGTG TCCGCAGTTT CCCAGCTGAC   1980
TGACTCCCCA GACACCACAG AGGAAGCCAC CCCAGTTCAG GAGGTAGAGG GTGGTGTGCT   2040
AGATACAGAA GAAGAGGAGC GCCAGACGCA GGCCATCCTC CAAGCCGTTG CAGACAAGGT   2100
GAAAGAGGAG TCCCAGGTGC CTGCAACCCA GACTGTGCAG AGAACGGGGT CAAAAGCACT   2160
GGAGAAGGTT GAGGAGGTAG AGGAGGACTC CGAAGTGCTG GCTTCGGAGA AAGAGAAGGA   2220
CGTTATGCCG AAAGGACCCG TGCAGGAAGC TGGAGCTGAG CATCTTGCAC AGGGCTCTGA   2280
GACTGGACAG GCTACTCCAG AGAGCCTTGA AGTTCCTGAA GTCACAGCAG ATGTAGACCA   2340
TGTCGCCACG TGCCAGGTTA TCAAGCTCCA GCAGCTGATG GAACAGGCCG TGGCCCCTGA   2400
GTCATCCGAA ACCTTGACAG ACAGTGAGAC AAATGGAAGC ACTCCCTTAG CAGATTCAGA   2460
CACTGCAGAT GGGACACAGC AAGATGAAAC CATTGACAGC CAGGACAGTA AAGCCACTGC   2520
AGCTGTCAGG CAGTCACAGG TCACAGAAGA AGAGGCGGCT ACTGCTCAGA AAGAGGAGCC   2580
TTCGACACTA CCTAATAATG TTCCAGCCCA GGAAGAACAT GGGGAAGAAC CAGGAAGAGA   2640
```

-continued

```
TGTTCTTGAA CCTACACAGC AAGAGCTTGC TGCTGCAGCC GTGCCCGTCT GGCAAAAGAC   2700
TGAGGTGGGT CAAGAGGGTG AGGTTGACTG GTTGGATGGA GAAAAAGTCA AAGAAGAACA   2760
GGAGGTGTTT GTACACTCTG GACCCAACAG TCAAAAGGCT GCTGATGTGA CATATGACAG   2820
TGAAGTGATG GGAGTGGCCG GGTGTCAGGA AAAGGAGAGT ACTGAAGTGC AGAGTCTTAG   2880
CCTGGAGGAG GGAGAGATGG AAACTGACGT TGAAAAGGAG AAAAGGGAGA CAAAGCCAGA   2940
GCAAGTGAGT GAAGAAGGTG AGCAGGAAAC AGCCGCTCCT GAGCATGAAA GGAACTACGG   3000
GAAGCCAGTC CTGACACTTG ACATGCCCAG CTCAGAGAGG GGGAAGGCAC TGGGAAGCCT   3060
TGGAGGAAGC CCTTCTCTCC CAGACCAAGA CAAAGCAGGT TGCATAGAGG TTCAAGTTCA   3120
AAGCCTGGAC ACAACAGTCA CTCAAACAGC AGAAGCTGTG GAAAAGGTCA TAGAAACGGT   3180
TGTGATTTCA GAGACAGGTG AAAGTCCAGA GTGTGTAGGT GCACACTTAT TACCAGCTGA   3240
GAAGTCCTCT GCAACGGGTG GCCACTGGAC TCTTCAGCAT GCAGAGGACA CGGTACCCCT   3300
GGGGCCTGAG TCTCAGGCAG AATCCATCCC AATCATAGTA ACTCCTGCTC CTGAAAGCAC   3360
CCTACATCCT GACCTACAAG GAGAAATAAG CGCATCCCAG AGAGAGCGAT CAGAGGAAGA   3420
GGACAAGCCA GATGCTGGTC CTGATGCTGA CGGCAAGGAG AGTACAGCAA TCGACAAAGT   3480
CCTCAAGGCT GAACCTGAGA TCCTGGAACT TGAGAGTAAG AGCAACAAGA TTGTGCTGAA   3540
CGTCATTCAG ACAGCCGTTG ACCAGTTCGC ACGTACAGAA ACAGCCCCCG AAACTCATGC   3600
TTATGATTCA CAGACCCAGG TTCCTGCAAT GCGCTTGGAC AGCAGGGAGC CCAACAGATG   3660
CTGGACAAAA ATGAAAGTTG CCAAGATGAA ACACCCAGTG CCGCAGCCCA GAGAGGACTT   3720
GCAAGTCCTG ACCGTTCTGG AGGCATGGCT CAGCTCGGAA ATGCTTGCCG CGCTTGCAGT   3780
TGAAAGCGCC GGTGTCAAAG TAAGCATTGA GAAGCTGCCT CCTCAACCCA AAGATCAAAA   3840
GGAGCATGCT GCTGATGGCC CTCAGCTCCA AAGCTTAGCC CAGGCAGAGG CAGTGTCTGG   3900
AAACCTAACC AAAGAATCCC CAGACACCAA CGGACCAAAG CTAACCGAGG AGCGATGCCC   3960
CCAAAAGTTG AGGTCCAGGA AGAAGAAATG TCTACCAAGT CAGTCAAAGA GAACAAGGCC   4020
CAGGCAGAAG AGGACCTGCA GGAGCCAAAG GGAGACCTGG CAGAATCCTA AGATGTTAGT   4080
TGCTCATTGT ACATCTGTAA GACCAGAATG TGAAAACAAG TCACAGAACA AGATGCTGCT   4140
GTTGGGACCT TGGACCAAGA TTTCAGAGCC CATGAGATCC AGAGAGCAGG GCCGTCCAAT   4200
GATTTCCACC CAGTAGAGCA CCCCGACAAT TCTGAGGCTT CATCGGGAGC TAGAGCCAGC   4260
TAACATTTCC TCGTTTCAAG ACTGCCTTTG ATTTGCCCCT TGATGCCGTC CGTGTATTTC   4320
GGATTTAAGG TCCTGCGTTC TCAACCTGGA ACCAATTCTG CCATACCTAG TTCCACTTCT   4380
CAAACTGGAG CATCCTCCTT TATGTATTTA TATGTATGTT TTATGTAGTC CTCCTCCTGT   4440
ACCTATTGTA TATTTTTTTC TAACGTTTAA GCACATGCTT TTTGTATTAT GCAATATATA   4500
ACGGGTGTGC AGCCATAGCG ACGCTTTGAA AAGCTCCAAG CCTCAACTGT AACCTGCAGC   4560
AAACAGATAA CATTCCTGGC AAGAAGAGAC AAGTCTTTTT TAAAGTTTAC TGATGCTTAG   4620
ATCTGTGGGC TTCTAGTCCT CTGAAAGTGG TTGTTTTCCT ATGCACAGCG AGCTCAGAAA   4680
TAAAAACCCC ATTTTGAAAC ATCCAGGATG TCCCAATATT ACCATGATTT TTTCCCCCCT   4740
TTTTGCTAAT CCAGTCCAGG TTGGAAAGAA GTCTCCTCTG TGTCAGATTA AGCCCTGTCT   4800
CTTAATGATA TGGACAAATG AGTGTGCCTA AGGCCATGAG ATGTTTCCTA ATGCAGAAGG   4860
AATCTGTTGT ACGTTTTTTT GATTGTACTC TTCTATGCTG GACCGAATTC ATATGCAGAT   4920
CGAAGTGAGT CCTGTTCTTT ACAGATGGTA TTTTGATAGA TACTGGAGTT TGTCTGTGTT   4980
```

-continued

```
ATATCTGTGC CCCTTCTTTA AGAACAATGT TGCATTATGT TCCTTTGGAT AAATTGTGAT   5040

TTGACAACTG ATTTAAATAA ACATATTTGA CTAC                               5074


(2) INFORMATION FOR SEQ ID NO:2:

     (i) SEQUENCE CHARACTERISTICS:
          (A) LENGTH: 1346 amino acids
          (B) TYPE: amino acid
          (C) STRANDEDNESS: single
          (D) TOPOLOGY: linear

    (ii) MOLECULE TYPE: peptide

   (iii) HYPOTHETICAL: NO

    (iv) ANTI-SENSE: NO

     (v) FRAGMENT TYPE: internal

    (vi) ORIGINAL SOURCE:

    (xi) SEQUENCE DESCRIPTION: SEQ ID NO:2:

Met Glu Ala His Gln Glu Val Val Ala Glu Val His Val Ser Thr Val
 1               5                  10                  15

Glu Lys Thr Glu Glu Glu Gln Gly Gly Gly Gly Glu Ala Glu Gly Gly
            20                  25                  30

Val Val Val Glu Gly Thr Gly Glu Ser Leu Pro Pro Glu Lys Leu Ala
        35                  40                  45

Glu Pro Gln Glu Val Pro Gln Glu Ala Glu Pro Ala Glu Glu Leu Met
    50                  55                  60

Lys Ser Arg Glu Met Cys Val Ser Gly Gly Asp His Thr Gln Leu Thr
65                  70                  75                  80

Asp Leu Ser Pro Glu Glu Lys Thr Leu Pro Lys His Pro Glu Gly Ile
                85                  90                  95

Val Ser Glu Val Glu Met Leu Ser Ser Gln Glu Arg Ile Lys Val Gln
            100                 105                 110

Gly Ser Pro Leu Lys Lys Leu Phe Ser Ser Ser Gly Leu Lys Lys Leu
        115                 120                 125

Ser Gly Lys Lys Gln Lys Gly Lys Arg Gly Gly Gly Gly Asp Glu Glu
    130                 135                 140

Pro Gly Glu Tyr Gln His Ile His Thr Glu Ser Pro Glu Ser Ala Asp
145                 150                 155                 160

Glu Gln Lys Gly Glu Ser Ser Ala Ser Ser Pro Glu Glu Pro Glu Glu
                165                 170                 175

Thr Thr Cys Leu Glu Lys Gly Pro Leu Glu Ala Pro Arg Met Gly Lys
            180                 185                 190

Leu Arg Lys Glu Leu Leu Arg Gly Glu Lys Lys Arg Lys Asp His Ser
        195                 200                 205

Leu Gly Ile Leu Gln Lys Asp Gly Asp Thr Gln Glu Thr Val Arg Arg
    210                 215                 220

Pro Ser Glu Ser Asp Lys Glu Glu Glu Leu Glu Lys Val Lys Ser Ala
225                 230                 235                 240

Thr Leu Ser Ser Thr Asp Ser Thr Val Ser Glu Met Gln Asp Glu Val
                245                 250                 255

Lys Thr Val Gly Glu Glu Gln Lys Pro Glu Glu Pro Lys Arg Arg Val
            260                 265                 270

Asp Thr Ser Val Ser Trp Glu Ala Leu Ile Cys Val Gly Ser Ser Lys
        275                 280                 285
```

-continued

```
Lys Arg Ala Arg Lys Ala Ser Ser Ser Asp Ile Arg Gly Pro Arg Thr
    290                 295                 300

Leu Gly Gly Gly Gln Ser Gln Ser Arg Gly Gly Gln Gln Arg Gln Arg
305                 310                 315                 320

Ser Arg Thr Asp Ala Val Pro Ala Ser Thr Gln Glu Gln Asp Gln Ala
                325                 330                 335

Gln Gly Ser Ser Ser Pro Glu Pro Ala Gly Ser Pro Ser Glu Gly Glu
            340                 345                 350

Gly Val Ser Thr Trp Glu Ser Phe Lys Arg Leu Val Thr Pro Arg Lys
        355                 360                 365

Lys Ser Lys Ser Lys Leu Glu Glu Lys Glu Ala Gly Arg Thr Leu Val
    370                 375                 380

Val Gly Ala Gly Cys Pro Leu Arg Ser Asn Arg Val Glu Lys Asn Leu
385                 390                 395                 400

Gly Phe Pro Leu Arg Asn Ser Ser Pro Asp Gly Gly Arg Lys Gly Gln
                405                 410                 415

Met Gly Arg Gln Glu Gln Ala Thr Val Glu Asp Ser Gly Pro Val Glu
            420                 425                 430

Ile Asn Glu Asp Glu Pro Asp Val Pro Ala Val Val Pro Leu Ser Glu
        435                 440                 445

Tyr Asp Ala Val Glu Arg Glu Lys Met Glu Ala Gln Gly Asn Ala Glu
    450                 455                 460

Leu Pro Ser Cys Trp Gly Cys Val Val Ser Glu Glu Leu Ser Lys Thr
465                 470                 475                 480

Leu Val His Thr Val Ser Val Ala Val Ile Asp Gly Thr Arg Ala Val
                485                 490                 495

Thr Ser Val Glu Glu Arg Ser Pro Ser Trp Ile Ser Ala Ser Val Thr
            500                 505                 510

Glu Pro Leu Glu His Thr Ala Gly Glu Ala Met Pro Pro Val Glu Glu
        515                 520                 525

Val Thr Glu Lys Asp Ile Ile Ala Glu Glu Thr Pro Val Leu Thr Gln
    530                 535                 540

Thr Leu Pro Glu Gly Lys Asp Ala His Asp Asp Met Val Thr Ser Glu
545                 550                 555                 560

Val Asp Phe Thr Ser Glu Ala Val Thr Ala Thr Glu Thr Ser Glu Ala
                565                 570                 575

Leu Arg Thr Glu Glu Val Thr Glu Ala Ser Gly Ala Glu Glu Thr Thr
            580                 585                 590

Asp Met Val Ser Ala Val Ser Gln Leu Thr Asp Ser Pro Asp Thr Thr
        595                 600                 605

Glu Glu Ala Thr Pro Val Gln Glu Val Glu Gly Gly Val Leu Asp Thr
    610                 615                 620

Glu Glu Glu Glu Arg Gln Thr Gln Ala Ile Leu Gln Ala Val Ala Asp
625                 630                 635                 640

Lys Val Lys Glu Glu Ser Gln Val Pro Ala Thr Gln Thr Val Gln Arg
                645                 650                 655

Thr Gly Ser Lys Ala Leu Glu Lys Val Glu Glu Val Glu Glu Asp Ser
            660                 665                 670

Glu Val Leu Ala Ser Glu Lys Glu Lys Asp Val Met Pro Lys Gly Pro
        675                 680                 685

Val Gln Glu Ala Gly Ala Glu His Leu Ala Gln Gly Ser Glu Thr Gly
    690                 695                 700

Gln Ala Thr Pro Glu Ser Leu Glu Val Pro Glu Val Thr Ala Asp Val
```

-continued

```
705                 710                 715                 720

Asp His Val Ala Thr Cys Gln Val Ile Lys Leu Gln Gln Leu Met Glu
                725                 730                 735

Gln Ala Val Ala Pro Glu Ser Ser Glu Thr Leu Thr Asp Ser Glu Thr
            740                 745                 750

Asn Gly Ser Thr Pro Leu Ala Asp Ser Asp Thr Ala Asp Gly Thr Gln
        755                 760                 765

Gln Asp Glu Thr Ile Asp Ser Gln Asp Ser Lys Ala Thr Ala Ala Val
    770                 775                 780

Arg Gln Ser Gln Val Thr Glu Glu Glu Ala Ala Thr Ala Gln Lys Glu
785                 790                 795                 800

Glu Pro Ser Thr Leu Pro Asn Asn Val Pro Ala Gln Glu Glu His Gly
                805                 810                 815

Glu Glu Pro Gly Arg Asp Val Leu Glu Pro Thr Gln Gln Glu Leu Ala
            820                 825                 830

Ala Ala Ala Val Pro Val Trp Gln Lys Thr Glu Val Gly Gln Glu Gly
        835                 840                 845

Glu Val Asp Trp Leu Asp Gly Glu Lys Val Lys Glu Glu Gln Glu Val
              850                 855                 860

Phe Val His Ser Gly Pro Asn Ser Gln Lys Ala Ala Asp Val Thr Tyr
865                 870                 875                 880

Asp Ser Glu Val Met Gly Val Ala Gly Cys Gln Glu Lys Glu Ser Thr
                885                 890                 895

Glu Val Gln Ser Leu Ser Leu Glu Glu Gly Glu Met Glu Thr Asp Val
            900                 905                 910

Glu Lys Glu Lys Arg Glu Thr Lys Pro Glu Gln Val Ser Glu Glu Gly
        915                 920                 925

Glu Gln Glu Thr Ala Ala Pro Glu His Glu Arg Asn Tyr Gly Lys Pro
    930                 935                 940

Val Leu Thr Leu Asp Met Pro Ser Ser Glu Arg Gly Lys Ala Leu Gly
945                 950                 955                 960

Ser Leu Gly Gly Ser Pro Ser Leu Pro Asp Gln Asp Lys Ala Gly Cys
                965                 970                 975

Ile Glu Val Gln Val Gln Ser Leu Asp Thr Thr Val Thr Gln Thr Ala
            980                 985                 990

Glu Ala Val Glu Lys Val Ile Glu Thr Val Val Ile Ser Glu Thr Gly
        995                 1000                1005

Glu Ser Pro Glu Cys Val Gly Ala His Leu Leu Pro Ala Glu Lys Ser
   1010                1015                1020

Ser Ala Thr Gly Gly His Trp Thr Leu Gln His Ala Glu Asp Thr Val
1025               1030                1035                1040

Pro Leu Gly Pro Glu Ser Gln Ala Glu Ser Ile Pro Ile Ile Val Thr
              1045                1050                1055

Pro Ala Pro Glu Ser Thr Leu His Pro Asp Leu Gln Gly Glu Ile Ser
          1060                1065                1070

Ala Ser Gln Arg Glu Arg Ser Glu Glu Glu Asp Lys Pro Asp Ala Gly
      1075                1080                1085

Pro Asp Ala Asp Gly Lys Glu Ser Thr Ala Ile Asp Lys Val Leu Lys
   1090                1095                1100

Ala Glu Pro Glu Ile Leu Glu Leu Glu Ser Lys Ser Asn Lys Ile Val
1105               1110                1115                1120

Leu Asn Val Ile Gln Thr Ala Val Asp Gln Phe Ala Arg Thr Glu Thr
                1125                1130                1135
```

-continued

```
 Ala Pro Glu Thr His Ala Tyr Asp Ser Gln Thr Gln Val Pro Ala Met
            1140                1145                1150

 Arg Leu Asp Ser Arg Glu Pro Asn Arg Cys Trp Thr Lys Met Lys Val
        1155                1160                1165

 Ala Lys Met Lys His Pro Val Pro Gln Pro Arg Glu Asp Leu Gln Val
    1170                1175                1180

 Leu Thr Val Leu Glu Ala Trp Leu Ser Ser Glu Met Leu Ala Ala Leu
1185                1190                1195                1200

 Ala Val Glu Ser Ala Gly Val Lys Val Ser Ile Glu Lys Leu Pro Pro
                1205                1210                1215

 Gln Pro Lys Asp Gln Lys Glu His Ala Ala Asp Gly Pro Gln Leu Gln
            1220                1225                1230

 Ser Leu Ala Gln Ala Glu Ala Val Ser Gly Asn Leu Thr Lys Glu Ser
        1235                1240                1245

 Pro Asp Thr Asn Gly Pro Lys Leu Thr Glu Glu Arg Cys Pro Gln Lys
    1250                1255                1260

 Leu Arg Ser Arg Lys Lys Lys Cys Leu Pro Ser Gln Ser Lys Arg Thr
1265                1270                1275                1280

 Arg Pro Arg Gln Lys Arg Thr Cys Arg Ser Gln Arg Glu Thr Trp Gln
                1285                1290                1295

 Asn Pro Lys Met Leu Val Ala His Cys Thr Ser Val Arg Pro Glu Cys
            1300                1305                1310

 Glu Asn Lys Ser Gln Asn Lys Met Leu Leu Leu Gly Pro Trp Thr Lys
        1315                1320                1325

 Ile Ser Glu Pro Met Arg Ser Arg Glu Gln Gly Arg Pro Met Ile Ser
    1330                1335                1340

 Thr Gln
1345
```

(2) INFORMATION FOR SEQ ID NO:3:

(i) SEQUENCE CHARACTERISTICS:
(A) LENGTH: 5200 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

```
ATGGGCGCAG GCAGTTCCAC CGAGCAGCGG AGCCCCGAGC AGCCGGCGGG GAGCGACACG     60

CCGAGCGAGC TGGTGCTCAG TGGCCATGGG CCCGCAGCTG AAGCCTCGGG AGCAGCTGGA    120

GACCCCGCCG ACGCGGACCC CGCCACCAAG CTCCCACAGA AGAATGGCCA GCTGTCTTCT    180

GTCAACGGCG TAGCTGAACA AGGAGATGTC CATGTCCAAG AGGAAAACCA GGAGGGGCAG    240

GAGGAAGAAG TCGTTGATGA GGATGTTGGA CAGCGAGAGT CAGAAGATGT GAGAGAAAAA    300

GACCGAGTTG AAGAAATGGC GGCCAACTCC ACAGCTGTTG AAGATATCAC AAAGGATGGG    360

CAGGAGGAGA CATCAGAAAT AATTGAACAG ATCCCTGCTT CAGAAAACAA TGTGGAAGAA    420

ATGGTACAGC CTGCTGAGTC CCAGGCTAAT GATGTTGGCT TCAAGAAAGT ATTTAAATTT    480
```

-continued

```
GTTGGTTTTA AATTCACGGT GAAGAAGGAT AAAAATGAAA AGTCAGATAC TGTCCAACTA    540
CTCACTGTCA AGAAGGATGA AGGCGAAGGG GCAGAAGCCT CTGTCGGAGC TGGAGACCAC    600
CAGGAGCCCA GTGTGGAGAC TGCCGTCGGA GAGTCAGCAT CCAAAGAAAG TGAGCTGAAG    660
CAATCCACAG AGAAGCAAGA AGGCACCCTG AAGCAAGAAC AGAGCAGCAC AGAAATCCCC    720
CTTCAAGCCG AATCTGATCA AGCGGCTGAG GAAGAAGCCA AAGATGAAGG AGAAGAAAAA    780
CAAGAGAAAG AGCCCACCAA GTCCCCAGAA TCCCCGAGCA GCCCAGTCAA CAGTGAGACA    840
ACATCTTCCT TCAAGAAGTT CTTCACTCAC GGTTGGGCCG GCTGGCGCAA GAAGACCAGC    900
TTCAAGAAAT CAAAAGAGGA TGATCTGGAA ACTGCCGAGA AGAGAAAGGA GCAAGAGGCA    960
GAAAAAGTAG ACGAGGAAGA AAAGGAAAAG ACAGAGCCAG CCTCGGAGGA GCAGGAGCCG   1020
GCAGAAGACA CAGACCAGGC CAGGTTGTCA GCAGACTACG AGAAGGTGGA GCTGCCTTTG   1080
GAAGACCAGG TTGGTGACCT GGAGGCATCG TCAGAGGAGA AGTGTGCTCC TTTGGCAACG   1140
GAAGTGTTTG ATGAGAAGAT GGAAGCCCAC CAAGAAGTTG TTGCAGAGGT CCACGTGAGC   1200
ACCGTGGAGA AGACAGAGGA GGAGCAGGGA GGAGGAGGAG AGGCTGAAGG GGGCGTGGTG   1260
GTAGAAGGAA CAGGAGAATC CTTGCCCCCT GAGAAACTGG CTGAGCCCCA GGAGGTCCCC   1320
CAGGAAGCTG AGCCTGCTGA GGAGCTGATG AAGAGCAGAG AGATGTGTGT CTCTGGAGGA   1380
GACCACACTC AACTGACAGA CCTAAGTCCT GAAGAGAAGA CGCTGCCCAA ACACCCAGAA   1440
GGCATTGTCA GTGAGGTGGA GATGCTGTCC TCTCAGGAAA GAATCAAGGT ACAGGGAAGT   1500
CCCTTGAAGA AACTCTTCAG TAGCTCAGGC TTAAAGAAGC TGTCTGGGAA GAAGCAGAAG   1560
GGGAAACGAG GAGGTGGGGG AGACGAAGAG CCTGGAGAAT ACCAACACAT TCACACCGAA   1620
TCCCCAGAGA GTGCTGATGA GCAGAAGGGA GAGAGCTCTG CGTCGTCCCC CGAGGAGCCT   1680
GAGGAGACCA CGTGTCTGGA GAAAGGGCCG CTGGAAGCAC CCCAGGATGG GGAAGCTGAG   1740
GAAGGAACTA CTTCCGATGG AGAGAAGAAG AGAGAAGGGA TCACTCCCTG GGCATCCTTC   1800
AAAAAGATGG TGACACCCAA GAAACGGGTC CGAAGACCTT CTGAGAGTGA CAAGGAGGAA   1860
GAGCTGGAGA AGGTCAAGAG CGCCACCTTG TCCTCCACTG ATAGCACAGT GTCAGAAATG   1920
CAAGATGAAG TCAAAACTGT TGGTGAGGAA CAAAAGCCAG AGGAACCAAA GCGTAGGGTG   1980
GATACTTCAG TGTCTTGGGA AGCACTGATT TGTGTCGGAT CATCCAAGAA GAGAGCAAGG   2040
AAGGCATCCT CTTCAGATGA TGAAGGAGGG CCAAGGACAC TGGGAGGGGA CAGTCACAGA   2100
GCAGAGGAGG CCAGCAAAGA CAAAGAAGCC GGAACAGACG CTGTTCCTGC CAGCACCCAG   2160
GAGCAGGACC AAGCGCAAGG AAGTTCCTCA CCCGAGCCAG CGGGAAGCCC TTCCGAAGGG   2220
GAAGGTGTCT CCACTTGGGA GTCATTTAAA AGATTAGTCA CTCCAAGAAA AAAATCCAAG   2280
TCAAAACTGG AAGAGAAAGC CGAAGACTCT AGTGTAGAGC AGTTGTCCAC TGAGATCGAA   2340
CCGAGTAGAG AAGAATCTTG GGTTTCCATT AAGAAATTCA TCCCCGGACG GCGGAAGAAA   2400
AGGGCAGACG GGAAGCAAGA ACAAGCCACT GTGGAAGACT CAGGGCCAGT GGAGATAAAT   2460
GAGGACGACC CTAATGTCCC AGCCGTCGTG CCTCTGTCTG AGTATAATGC AGTGGAGAGG   2520
GAGAAGATGG AAGCCCAGGG GAATACGGAG CTGCCCCAGC TGCTGGGGGC TGTGTACGTG   2580
TCCGAGGAGC TCAGTAAGAC TCTGGTCCAC ACTGTGAGTG TCGCAGTCAT TGATGGGACC   2640
AGGGCAGTCA CCAGTGTCGA AGAGCGGTCT CCTTCGTGGA TATCCGCTTC CGTAACAGAA   2700
CCTCTTGAAC ACACAGCGGG AGAAGCCATG CCACCTGTTG AAGAGGTCAC TGAAAAAGAC   2760
ATCATTGCAG AAGAAACTCC TGTGCTCACC CAGACGTTAC CAGAGGGTAA AGATGCCCAT   2820
```

-continued

```
GACGACATGG TCACCAGTGA AGTGGATTTC ACCTCAGAAG CTGTGACAGC CACAGAGACC   2880
TCAGAGGCTC TCCGTACTGA AGAAGTTACC GAAGCATCGG GGGCCGAAGA GACCACAGAC   2940
ATGGTGTCCG CAGTTTCCCA GCTGACTGAC TCCCCAGACA CCACAGAGGA AGCCACCCCA   3000
GTTCAGGAGG TAGAGAGTGG TGTGCTAGAT ACAGAAGAAG AGGAGCGCCA GACGCAGGCC   3060
ATCCTCCAAG CCGTTGCAGA CAAGGTGAAA GAGGAGTCCC AGGTGCCTGC AACCCAGACT   3120
GTGCAGAGAA CGGGGTCAAA AGCACTGGAG AAGGTTGAGG AGGTAGAGGA GGACTCCGAA   3180
GTGCTGGCTT CGGAGAAAGA GAAGGACGTT ATGCCGAAAG GACCCGTGCA GGAAGCTGGA   3240
GCTGAGCATC TTGCACAGGG CTCTGAGACT GGACAGGCTA CTCCAGAGAG CCTTGAAGTT   3300
CCTGAAGTCA CGGCAGATGT AGACCATGTC GCCACGTGCC AGGTTATCAA GCTCCAGCAG   3360
CTGATGGAAC AGGCCGTGGC CCCTGAGTCA TCCGAAACCT TGACAGACAG TGAGACAAAT   3420
GGAAGCACTC CCTTAGCAGA TTCAGACACT GCAGATGGGA CACAGCAAGA TGAAACCATT   3480
GACAGCCAGG ACAGTAAAGC CACTGCAGCT GTCAGGCAGT CACAGGTCAC AGAAGAAGAG   3540
GCGGCTACTG CTCAGAAAGA GGAGCCTTCG ACACTACCTA ATAATGTTCC AGCCCAGGAA   3600
GAACATGGGG AAGAACCAGG AAGAGATGTT CTTGAACCTA CACAGCAAGA GCTTACTGCT   3660
GCAGCCGTGC CCGTTCTGGC AAAGACTGAG GTGGGTCAAG AGGGTGAGGT TGACTGGTTG   3720
GATGGAGAAA AAGTCAAAGA AGAACAGGAG GTGTTTGTAC ACTCTGGACC CAACAGTCAA   3780
AAGGCTGCTG ATGTGACATA TGACAGTGAA GTGATGGGAG TGGCCGGGTG TCAGGAAAAG   3840
GAGAGTACTG AAGTGCAGAG TCTTAGCCTG GAGGAGGGAG AGATGGAAAC TGACGTTGAA   3900
AAGGAGAAAA GGGAGACAAA GCCAGAGCAA GTGAGTGAAG AAGGTGAGCA GGAAACAGCC   3960
GCTCCTGAGC ATGAAGGAAC CTACGGGAAG CCAGTCCTGA CACTTGACAT GCCCAGCTCA   4020
GAGAGGGGGA AGGCACTGGG AAGCCTTGGA GGAAGCCCTT CTCTCCCAGA CCAAGACAAA   4080
GCAGGTTGCA TAGAGGTTCA AGTTCAAAGC CTGGACACAA CAGTCACTCA AACAGCAGAA   4140
GCTGTGGAAA AGGTCATAGA AACGGTTGTG ATTTCAGAGA CAGGTGAAAG TCCAGAGTGT   4200
GTAGGTGCAC ACTTATTACC AGCTGAGAAG TCCTCTGCAA CGGGTGGCCA CTGGACTCTT   4260
CAGCATGCAG AGGACACGGT ACCCCTGGGG CCTGAGTCTC AGGCAGAATC CATCCCAATC   4320
ATAGTAACTC CTGCTCCTGA AAGCACCCTA CATCCTGACC TACAAGGAGA AATAAGCGCA   4380
TCCCAGAGAG AGCGATCAGA GGAAGAGGAC AAGCCAGATG CTGGTCCTGA TGCTGACGGC   4440
AAGGAGAGTA CAGCAATCGA AAAAGTCCTC AAGGCTGAAC CTGAGATCCT GGAACTTGAG   4500
AGTAAGAGCA ACAAGATTGT GCTGAACGTC ATTCAGACAG CCGTTGACCA GTTCGCACGT   4560
ACAGAAACAG CCCCCGAAAC TCATGCTTAT GATTCACAGA CCCAGGTTCC TGCATGCAGG   4620
CTTGACAGCA GGGAGCCCAA CAGATGCTGG ACAAAAATGA AAGATGCCAA GATGAAACAC   4680
CCAGTGCCGC AGCCCAGAGA GGACTTGCAA GTCCTGACCG TTCTGGAGGC ATGGGCTCAG   4740
CCTCGGAAAT GCTTGCCGCG CTTGCAGTTG AAAGCGCCGG TGTCAAAGTA AGCATTGAGA   4800
AGCTGCCTCC TCAACCCAAA GATCCAAAAG GAGCATGCTG CTGATGGCCC TCAGCTCCAA   4860
AGCTTAGCCC AGGCAGAGGC CAGTGCCTCT GGAAACCTAA CCAAAGAATC CCCAGACACC   4920
AACGGACCAA AGCTAACCGA GGAGGGCGAT CCCCCAAAAG TTGAGGTCCA GGAAGAAGAA   4980
ATGTCTACCA AGTCAGTCAA AGAGAACAAG GCCCAGGCAG AAGAGGACCT GCAGGAGCCA   5040
AAGGGAGACC TGGCAGAATC CTAAGATGTT AGTTGCTCAT TGTACATCTG TAAGACCAGA   5100
ATGTGAAAAC AAGTCACAGA ACAAGATGCT GCTGTTGGGA CCTTGAGACC AAGATTTCAG   5160
AGCCCATGAG ATCCAGAGAG CAGGGCCGTC CAATGATTTC                         5200
```

(2) INFORMATION FOR SEQ ID NO:4:

(i) SEQUENCE CHARACTERISTICS:
(A) LENGTH: 1596 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:4:

```
Met Gly Ala Gly Ser Ser Thr Glu Gln Arg Ser Pro Glu Gln Pro Ala
 1               5                  10                  15

Gly Ser Asp Thr Pro Ser Glu Leu Val Leu Ser Gly His Gly Pro Ala
            20                  25                  30

Ala Glu Ala Ser Gly Ala Ala Gly Asp Pro Ala Asp Ala Asp Pro Ala
        35                  40                  45

Thr Lys Leu Pro Gln Lys Asn Gly Gln Leu Ser Ser Val Asn Gly Val
    50                  55                  60

Ala Glu Gln Gly Asp Val His Val Gln Glu Glu Asn Gln Glu Gly Gln
65                  70                  75                  80

Glu Glu Glu Val Val Asp Glu Asp Val Gly Gln Arg Glu Ser Glu Asp
                85                  90                  95

Val Arg Glu Lys Asp Arg Val Glu Glu Met Ala Ala Asn Ser Thr Ala
            100                 105                 110

Val Glu Asp Ile Thr Lys Asp Gly Gln Glu Glu Thr Ser Glu Ile Ile
        115                 120                 125

Glu Gln Ile Pro Ala Ser Glu Asn Asn Val Glu Glu Met Val Gln Pro
    130                 135                 140

Ala Glu Ser Gln Ala Asn Asp Val Gly Phe Lys Lys Val Phe Lys Phe
145                 150                 155                 160

Val Gly Phe Lys Phe Thr Val Lys Lys Asp Lys Asn Glu Lys Ser Asp
                165                 170                 175

Thr Val Gln Leu Leu Thr Val Lys Lys Asp Glu Gly Glu Gly Ala Glu
            180                 185                 190

Ala Ser Val Gly Ala Gly Asp His Gln Glu Pro Ser Val Glu Thr Ala
        195                 200                 205

Val Gly Glu Ser Ala Ser Lys Glu Ser Glu Leu Lys Gln Ser Thr Glu
    210                 215                 220

Lys Gln Glu Gly Thr Leu Lys Gln Glu Gln Ser Ser Thr Glu Ile Pro
225                 230                 235                 240

Leu Gln Ala Glu Ser Asp Gln Ala Ala Glu Glu Glu Ala Lys Asp Glu
                245                 250                 255

Gly Glu Glu Lys Gln Glu Lys Glu Pro Thr Lys Ser Pro Glu Ser Pro
            260                 265                 270

Ser Ser Pro Val Asn Ser Glu Thr Thr Ser Ser Phe Lys Lys Phe Phe
        275                 280                 285

Thr His Gly Trp Ala Gly Trp Arg Lys Lys Thr Ser Phe Lys Lys Ser
    290                 295                 300
```

-continued

```
Lys Glu Asp Asp Leu Glu Thr Ala Glu Lys Arg Lys Glu Gln Glu Ala
305                 310                 315                 320

Glu Lys Val Asp Glu Glu Glu Lys Glu Lys Thr Glu Pro Ala Ser Glu
                325                 330                 335

Glu Gln Glu Pro Ala Glu Asp Thr Asp Gln Ala Arg Leu Ser Ala Asp
            340                 345                 350

Tyr Glu Lys Val Glu Leu Pro Leu Glu Asp Gln Val Gly Asp Leu Glu
        355                 360                 365

Ala Ser Ser Glu Glu Lys Cys Ala Pro Leu Ala Thr Glu Val Phe Asp
    370                 375                 380

Glu Lys Met Glu Ala His Gln Glu Val Val Ala Glu Val His Val Ser
385                 390                 395                 400

Thr Val Glu Lys Thr Glu Glu Glu Gln Gly Gly Gly Gly Glu Ala Glu
                405                 410                 415

Gly Gly Val Val Val Glu Gly Thr Gly Glu Ser Leu Pro Pro Glu Lys
            420                 425                 430

Leu Ala Glu Pro Gln Glu Val Pro Gln Glu Ala Glu Pro Ala Glu Glu
        435                 440                 445

Leu Met Lys Ser Arg Glu Met Cys Val Ser Gly Gly Asp His Thr Gln
    450                 455                 460

Leu Thr Asp Leu Ser Pro Glu Glu Lys Thr Leu Pro Lys His Pro Glu
465                 470                 475                 480

Gly Ile Val Ser Glu Val Glu Met Leu Ser Ser Gln Glu Arg Ile Lys
                485                 490                 495

Val Gln Gly Ser Pro Leu Lys Lys Leu Phe Ser Ser Ser Gly Leu Lys
            500                 505                 510

Lys Leu Ser Gly Lys Lys Gln Lys Gly Lys Arg Gly Gly Gly Gly Asp
        515                 520                 525

Glu Glu Pro Gly Glu Tyr Gln His Ile His Thr Glu Ser Pro Glu Ser
    530                 535                 540

Ala Asp Glu Gln Lys Gly Glu Ser Ser Ala Ser Ser Pro Glu Glu Pro
545                 550                 555                 560

Glu Glu Thr Thr Cys Leu Glu Lys Gly Pro Leu Glu Ala Pro Gln Asp
                565                 570                 575

Gly Glu Ala Glu Glu Gly Thr Thr Ser Asp Gly Glu Lys Lys Arg Glu
            580                 585                 590

Gly Ile Thr Pro Trp Ala Ser Phe Lys Lys Met Val Thr Pro Lys Lys
        595                 600                 605

Arg Val Arg Arg Pro Ser Glu Ser Asp Lys Glu Glu Glu Leu Glu Lys
    610                 615                 620

Val Lys Ser Ala Thr Leu Ser Ser Thr Asp Ser Thr Val Ser Glu Met
625                 630                 635                 640

Gln Asp Glu Val Lys Thr Val Gly Glu Glu Gln Lys Pro Glu Glu Pro
                645                 650                 655

Lys Arg Arg Val Asp Thr Ser Val Ser Trp Glu Ala Leu Ile Cys Val
            660                 665                 670

Gly Ser Ser Lys Lys Arg Ala Arg Lys Ala Ser Ser Ser Asp Asp Glu
        675                 680                 685

Gly Gly Pro Arg Thr Leu Gly Gly Asp Ser His Arg Ala Glu Glu Ala
    690                 695                 700

Ser Lys Asp Lys Glu Ala Gly Thr Asp Ala Val Pro Ala Ser Thr Gln
705                 710                 715                 720

Glu Gln Asp Gln Ala Gln Gly Ser Ser Ser Pro Glu Pro Ala Gly Ser
```

-continued

```
                725                 730                 735

Pro Ser Glu Gly Glu Gly Val Ser Thr Trp Glu Ser Phe Lys Arg Leu
            740                 745                 750

Val Thr Pro Arg Lys Lys Ser Lys Ser Lys Leu Glu Glu Lys Ala Glu
        755                 760                 765

Asp Ser Ser Val Glu Gln Leu Ser Thr Glu Ile Glu Pro Ser Arg Glu
    770                 775                 780

Glu Ser Trp Val Ser Ile Lys Lys Phe Ile Pro Gly Arg Arg Lys Lys
785                 790                 795                 800

Arg Ala Asp Gly Lys Gln Glu Gln Ala Thr Val Glu Asp Ser Gly Pro
                805                 810                 815

Val Glu Ile Asn Glu Asp Asp Pro Asn Val Pro Ala Val Val Pro Leu
            820                 825                 830

Ser Glu Tyr Asn Ala Val Glu Arg Glu Lys Met Glu Ala Gln Gly Asn
        835                 840                 845

Thr Glu Leu Pro Gln Leu Leu Gly Ala Val Tyr Val Ser Glu Glu Leu
    850                 855                 860

Ser Lys Thr Leu Val His Thr Val Ser Val Ala Val Ile Asp Gly Thr
865                 870                 875                 880

Arg Ala Val Thr Ser Val Glu Glu Arg Ser Pro Ser Trp Ile Ser Ala
                885                 890                 895

Ser Val Thr Glu Pro Leu Glu His Thr Ala Gly Glu Ala Met Pro Pro
            900                 905                 910

Val Glu Glu Val Thr Glu Lys Asp Ile Ile Ala Glu Glu Thr Pro Val
        915                 920                 925

Leu Thr Gln Thr Leu Pro Glu Gly Lys Asp Ala His Asp Asp Met Val
    930                 935                 940

Thr Ser Glu Val Asp Phe Thr Ser Glu Ala Val Thr Ala Thr Glu Thr
945                 950                 955                 960

Ser Glu Ala Leu Arg Thr Glu Glu Val Thr Glu Ala Ser Gly Ala Glu
                965                 970                 975

Glu Thr Thr Asp Met Val Ser Ala Val Ser Gln Leu Thr Asp Ser Pro
            980                 985                 990

Asp Thr Thr Glu Glu Ala Thr Pro Val Gln Glu Val Glu Ser Gly Val
        995                 1000                1005

Leu Asp Thr Glu Glu Glu Glu Arg Gln Thr Gln Ala Ile Leu Gln Ala
   1010                1015                1020

Val Ala Asp Lys Val Lys Glu Glu Ser Gln Val Pro Ala Thr Gln Thr
1025               1030                1035                1040

Val Gln Arg Thr Gly Ser Lys Ala Leu Glu Lys Val Glu Glu Val Glu
               1045                1050                1055

Glu Asp Ser Glu Val Leu Ala Ser Glu Lys Glu Lys Asp Val Met Pro
           1060                1065                1070

Lys Gly Pro Val Gln Glu Ala Gly Ala Glu His Leu Ala Gln Gly Ser
       1075                1080                1085

Glu Thr Gly Gln Ala Thr Pro Glu Ser Leu Glu Val Pro Glu Val Thr
   1090                1095                1100

Ala Asp Val Asp His Val Ala Thr Cys Gln Val Ile Lys Leu Gln Gln
1105               1110                1115                1120

Leu Met Glu Gln Ala Val Ala Pro Glu Ser Ser Glu Thr Leu Thr Asp
               1125                1130                1135

Ser Glu Thr Asn Gly Ser Thr Pro Leu Ala Asp Ser Asp Thr Ala Asp
           1140                1145                1150
```

-continued

```
Gly Thr Gln Gln Asp Glu Thr Ile Asp Ser Gln Asp Ser Lys Ala Thr
       1155                1160                1165

Ala Ala Val Arg Gln Ser Gln Val Thr Glu Glu Glu Ala Ala Thr Ala
   1170                1175                1180

Gln Lys Glu Glu Pro Ser Thr Leu Pro Asn Asn Val Pro Ala Gln Glu
1185               1190                1195                1200

Glu His Gly Glu Glu Pro Gly Arg Asp Val Leu Glu Pro Thr Gln Gln
               1205                1210                1215

Glu Leu Thr Ala Ala Ala Val Pro Val Leu Ala Lys Thr Glu Val Gly
           1220                1225                1230

Gln Glu Gly Glu Val Asp Trp Leu Asp Gly Glu Lys Val Lys Glu Glu
       1235                1240                1245

Gln Glu Val Phe Val His Ser Gly Pro Asn Ser Gln Lys Ala Ala Asp
   1250                1255                1260

Val Thr Tyr Asp Ser Glu Val Met Gly Val Ala Gly Cys Gln Glu Lys
1265               1270                1275                1280

Glu Ser Thr Glu Val Gln Ser Leu Ser Leu Glu Glu Gly Glu Met Glu
               1285                1290                1295

Thr Asp Val Glu Lys Glu Lys Arg Glu Thr Lys Pro Glu Gln Val Ser
           1300                1305                1310

Glu Glu Gly Glu Gln Glu Thr Ala Ala Pro Glu His Glu Gly Thr Tyr
       1315                1320                1325

Gly Lys Pro Val Leu Thr Leu Asp Met Pro Ser Ser Glu Arg Gly Lys
   1330                1335                1340

Ala Leu Gly Ser Leu Gly Gly Ser Pro Ser Leu Pro Asp Gln Asp Lys
1345               1350                1355                1360

Ala Gly Cys Ile Glu Val Gln Val Gln Ser Leu Asp Thr Thr Val Thr
               1365                1370                1375

Gln Thr Ala Glu Ala Val Glu Lys Val Ile Glu Thr Val Val Ile Ser
           1380                1385                1390

Glu Thr Gly Glu Ser Pro Glu Cys Val Gly Ala His Leu Leu Pro Ala
       1395                1400                1405

Glu Lys Ser Ser Ala Thr Gly Gly His Trp Thr Leu Gln His Ala Glu
   1410                1415                1420

Asp Thr Val Pro Leu Gly Pro Glu Ser Gln Ala Glu Ser Ile Pro Ile
1425               1430                1435                1440

Ile Val Thr Pro Ala Pro Glu Ser Thr Leu His Pro Asp Leu Gln Gly
               1445                1450                1455

Glu Ile Ser Ala Ser Gln Arg Glu Arg Ser Glu Glu Glu Asp Lys Pro
           1460                1465                1470

Asp Ala Gly Pro Asp Ala Asp Gly Lys Glu Ser Thr Ala Ile Glu Lys
       1475                1480                1485

Val Leu Lys Ala Glu Pro Glu Ile Leu Glu Leu Glu Ser Lys Ser Asn
   1490                1495                1500

Lys Ile Val Leu Asn Val Ile Gln Thr Ala Val Asp Gln Phe Ala Arg
1505               1510                1515                1520

Thr Glu Thr Ala Pro Glu Thr His Ala Tyr Asp Ser Gln Thr Gln Val
               1525                1530                1535

Pro Ala Cys Arg Leu Asp Ser Arg Glu Pro Asn Arg Cys Trp Thr Lys
           1540                1545                1550

Met Lys Asp Ala Lys Met Lys His Pro Val Pro Gln Pro Arg Glu Asp
       1555                1560                1565
```

```
 Leu Gln Val Leu Thr Val Leu Glu Ala Trp Ala Gln Pro Arg Lys Cys
    1570                1575                1580

 Leu Pro Arg Leu Gln Leu Lys Ala Pro Val Ser Lys
1585                1590                1595
```

(2) INFORMATION FOR SEQ ID NO:5:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:5:

```
Met Gly Ser Ser Lys Ser Lys Pro Lys Asp
 1               5                  10
```

(2) INFORMATION FOR SEQ ID NO:6:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

```
Met Gly Cys Ile Lys Ser Lys Glu Asp Lys
 1               5                  10
```

(2) INFORMATION FOR SEQ ID NO:7:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:7:

```
Met Gly Ala Gly Ser Ser Thr Glu Gln Arg
 1               5                  10
```

(2) INFORMATION FOR SEQ ID NO:8:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:8:

```
Met Gly Ala Gly Ala Ser Ala Glu Glu Lys
 1               5                  10
```

(2) INFORMATION FOR SEQ ID NO:9:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:9:

```
Met Gly Cys Thr Leu Ser Ala Glu Asp Lys
 1               5                  10
```

(2) INFORMATION FOR SEQ ID NO:10:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:10:

```
Met Leu Cys Cys Met Arg Arg Thr Lys Gln
 1               5                  10
```

(2) INFORMATION FOR SEQ ID NO:11:

(i) SEQUENCE CHARACTERISTICS:
(A) LENGTH: 23 amino acids
(B) TYPE: amino acid
(C) STRANDEDNESS: single
(D) TOPOLOGY: linear

```
    (ii) MOLECULE TYPE: peptide

   (iii) HYPOTHETICAL: NO

    (iv) ANTI-SENSE: NO

     (v) FRAGMENT TYPE: internal

    (vi) ORIGINAL SOURCE:

    (xi) SEQUENCE DESCRIPTION: SEQ ID NO:11:

Lys Arg Phe Ser Ser Lys Lys Ser Phe Lys Leu Ser Gly Phe Ser Phe
 1               5                  10                  15

Lys Lys Asn Lys Lys Glu Ala
            20


(2) INFORMATION FOR SEQ ID NO:12:

     (i) SEQUENCE CHARACTERISTICS:
          (A) LENGTH: 23 amino acids
          (B) TYPE: amino acid
          (C) STRANDEDNESS: single
          (D) TOPOLOGY: linear

    (ii) MOLECULE TYPE: peptide

   (iii) HYPOTHETICAL: NO

    (iv) ANTI-SENSE: NO

     (v) FRAGMENT TYPE: internal

    (vi) ORIGINAL SOURCE:

    (xi) SEQUENCE DESCRIPTION: SEQ ID NO:12:

Lys Arg Phe Ser Ser Lys Lys Ser Phe Lys Leu Ser Gly Phe Ser Phe
 1               5                  10                  15

Lys Lys Ser Lys Lys Glu Ala
            20


(2) INFORMATION FOR SEQ ID NO:13:

     (i) SEQUENCE CHARACTERISTICS:
          (A) LENGTH: 17 amino acids
          (B) TYPE: amino acid
          (C) STRANDEDNESS: single
          (D) TOPOLOGY: linear

    (ii) MOLECULE TYPE: peptide

   (iii) HYPOTHETICAL: NO

    (iv) ANTI-SENSE: NO

     (v) FRAGMENT TYPE: internal

    (vi) ORIGINAL SOURCE:

    (xi) SEQUENCE DESCRIPTION: SEQ ID NO:13:

Lys Lys Phe Ser Ser Lys Lys Pro Phe Lys Leu Ser Gly Phe Ser Phe
 1               5                  10                  15

Arg


(2) INFORMATION FOR SEQ ID NO:14:

     (i) SEQUENCE CHARACTERISTICS:
          (A) LENGTH: 20 amino acids
          (B) TYPE: amino acid
          (C) STRANDEDNESS: single
```

(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:14:

```
Lys Arg Arg Trp Lys Lys Ala Phe Ile Ala Val Ser Ala Ala Ala Arg
 1               5                  10                  15

Phe Lys Lys Cys
            20
```

(2) INFORMATION FOR SEQ ID NO:15:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:15:

```
Glu Thr Thr Ser Ser Phe Lys Lys Phe Phe Thr His Gly Thr Ser Phe
 1               5                  10                  15

Lys Lys Ser Lys Glu Asp Asp
            20
```

(2) INFORMATION FOR SEQ ID NO:16:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:16:

```
Lys Leu Phe Ser Ser Ser Gly Leu Lys Lys Leu Ser Gly Lys Lys Gln
 1               5                  10                  15

Lys Gly Lys Arg Gly Gly Gly
            20
```

(2) INFORMATION FOR SEQ ID NO:17:

(i) SEQUENCE CHARACTERISTICS:
(A) LENGTH: 23 amino acids (B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:17:

```
Glu Gly Ile Thr Pro Trp Ala Ser Phe Lys Lys Met Val Thr Pro Lys
 1               5                  10                  15

Lys Arg Val Arg Arg Pro Ser
            20
```

(2) INFORMATION FOR SEQ ID NO:18:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:18:

```
Glu Gly Val Ser Thr Trp Glu Ser Phe Lys Arg Leu Val Thr Pro Arg
 1               5                  10                  15

Lys Lys Ser Lys Ser Lys Leu
            20
```

(2) INFORMATION FOR SEQ ID NO:19:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:19:

```
Trp Ala Gly Trp Arg Lys Lys
 1               5
```

(2) INFORMATION FOR SEQ ID NO:20:

(i) SEQUENCE CHARACTERISTICS:
(A) LENGTH: 19 amino acids
(B) TYPE: amino acid

-continued

```
        (C) STRANDEDNESS: single
        (D) TOPOLOGY: linear

   (ii) MOLECULE TYPE: peptide

  (iii) HYPOTHETICAL: NO

   (iv) ANTI-SENSE: NO

    (v) FRAGMENT TYPE: internal

   (vi) ORIGINAL SOURCE:

   (xi) SEQUENCE DESCRIPTION: SEQ ID NO:20:

Glu Gly Xaa Xaa Trp Xaa Ser Phe Lys Lys Xaa Val Thr Pro Lys Lys
 1               5                  10                  15

Lys Xaa Lys
```

TUMOR SUPPRESSOR GENE

This application is a continuation application of Ser. No. 08/665,401 filed Jun. 8, 1996 now abandoned which is a continuation in part of Ser. No. 08/635,121 filed Apr. 19, 1996 which issued on Jun. 8, 1999 as U.S. Pat. No. 5,910, 442.

1. INTRODUCTION

The present invention relates to a novel tumor suppressor gene, referred to herein as SSeCKS, its encoded protein, and methods of use thereof. It is based, at least in part, on the discovery of a SSeCKS gene which encodes a substrate of protein kinase C that functions as both a mitogenic regulator as well as a tumor suppressor.

2. BACKGROUND OF THE INVENTION

The inactivation of several tumor suppressor gene families (for example, those encoding p53, Rb, and APC) as a result of mutation is acknowledged to contribute to oncogenicity of several types of human cancers (Levine, 1993, Ann. Rev. Biochem. 62:623–651). Many of these so-called class I tumor suppressor genes (Lee et al., 1991, Proc. Natl. Acad. Sci. U.S.A. 88:2825–2829) were identified and isolated following cumbersome pedigree and cytogenetic analyses (Sager, 1989, Science 246:1406–1412). Recently, another class of genes (class II) whose expression is known to be down-regulated in tumor cells has been shown by gene transfer techniques to encode potential tumor suppressors. These include nonmuscle α-actinin, tropomyosin I, CLP, retinoic acid receptor $\beta_1$, and interferon regulatory factor (Gluck et al., 1993, Proc. Natl. Acad Sci. U.S.A. 90:383–387; Hirada et al., 1993, Science 259:971–974; Hogel et al., 1993, Proc. Natl. Acad. Sci. U.S.A. 90:985–989; Mishra et al., 1994, J. Cell. Biochem. 18(Supp. C):171; Plasad et al., 1993, Proc. Natl. Acad. Sci. U.S.A. 90:7039–7043). Additional tumor suppressor gene families such as the maspin gene, rrg, and NO3 (Contente et al., 1993, Science 249:796–798; Ozaki et al., 1994, Cancer Res. 54:646–648; Zou et al., 1994, Science 263:526–529) were isolated by subtractive hybridization techniques designed to identify down-regulated genes. The ability of these genes to reverse an array of oncogenic phenotypes following gene transfer and over-expression supports the possibility for novel therapeutic modalities for cancer.

3. SUMMARY OF THE INVENTION

The present invention relates to a novel tumor suppressor gene, SSeCKS. It is based, at least in part, on the discovery of a gene, hitherto referred to as "322" (Lin et al., 1995, Mol. Cell. Biol. 15:2754–2762) but now referred to as SSeCKS, which was found to be down-regulated in certain transformed cells. Further, the SSeCKS gene product has been found to be a substrate of protein kinase C, and has been shown to act as a mitogenic regulator and as an inhibitor of the transformed phenotype.

In various embodiments, the present invention relates to the SSeCKS gene and protein, and in particular, to rat and human SSeCKS gene and protein. Furthermore, the present invention provides for the use of such genes and proteins in diagnostic and therapeutic methods.

4. BRIEF DESCRIPTION OF THE DRAWINGS

FIG. 1. Northern blot analysis of SSeCKS RNA levels in NIH 3T3 cells versus NIH/v-src transformed cells.

Figure 2A:
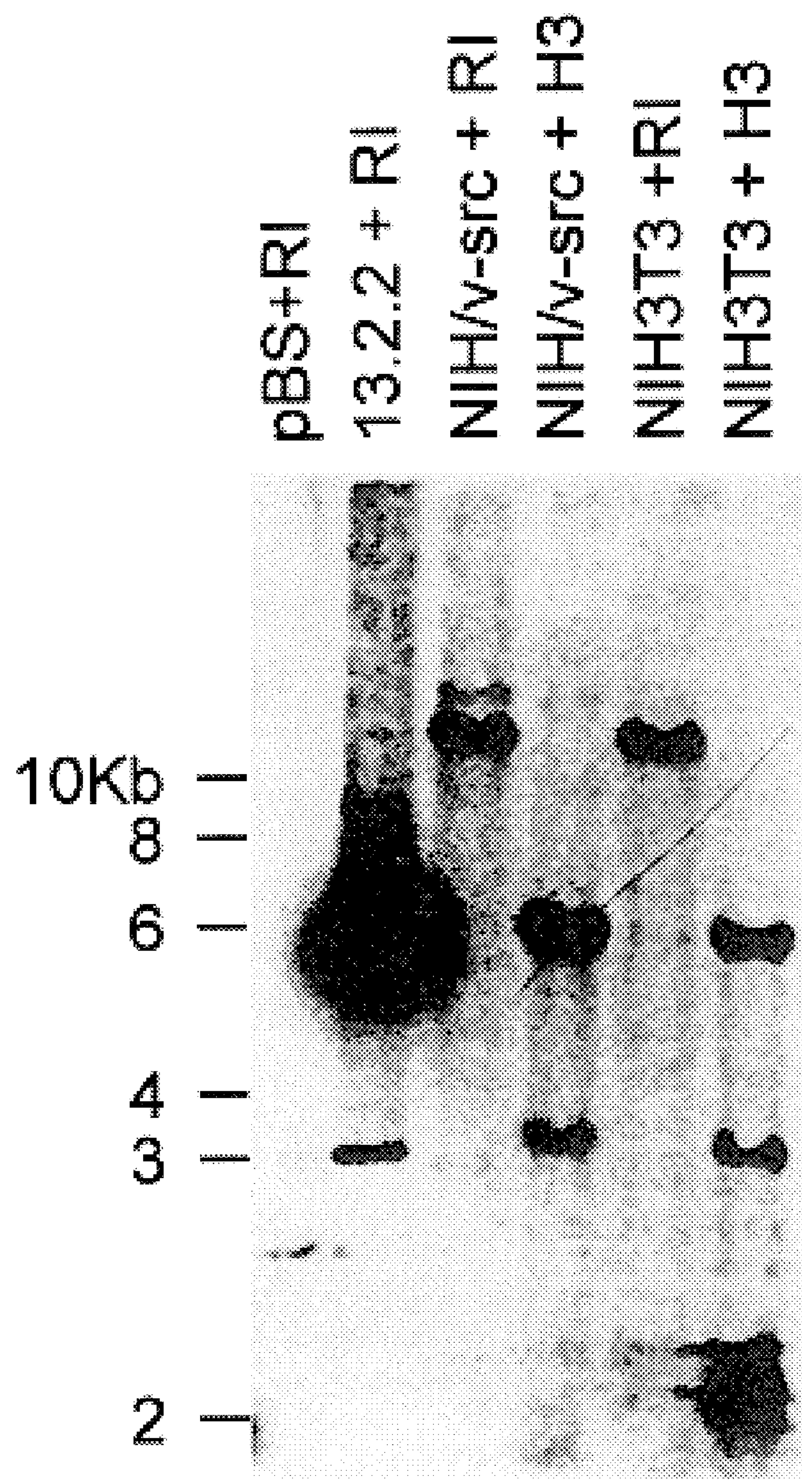
Figure 2B:
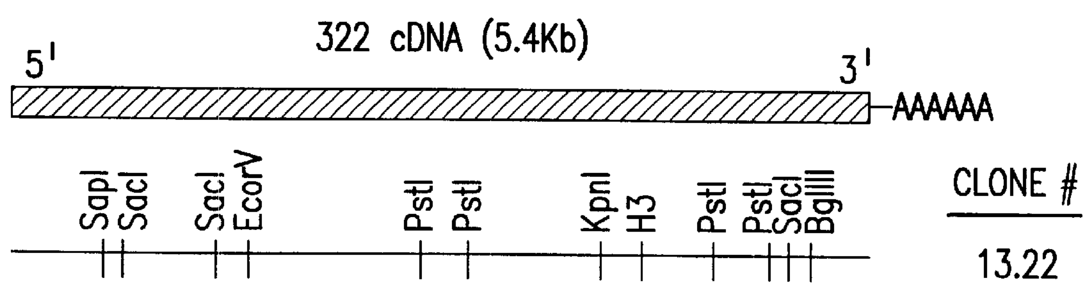

FIG. 2. Southern blot analysis showing that the decreased level of SSeCKS RNA in NIH/v-src cells is not due to gross deletion or translocation of the SSeCKS allele (A), and restriction map of SSeCKS (B).

FIG. 3. Nucleic acid SEQ ID NO: 1 (top line, lower case letters) and deduced amino acid SEQ ID NO: 2 (lower line, capital letters) sequence of rat SSeCKS cDNA encoding an active truncated form of SSeCKS.

FIG. 4. Northern blot analysis showing that the transcription of SSeCKS is suppressed relatively soon after the activation of a ts-src allele (A) or the addition of fetal calf serum (FCS) to starved rodent fibroblasts (B).

Figure 5:
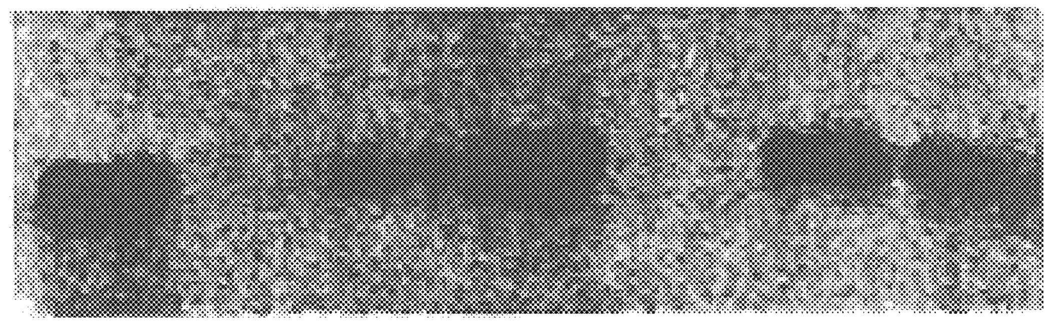

FIG. 5. Northern blot analyses showing levels of SSeCKS transcripts in oncogene-transformed Rat-6 fibroblasts.

Figure 6:
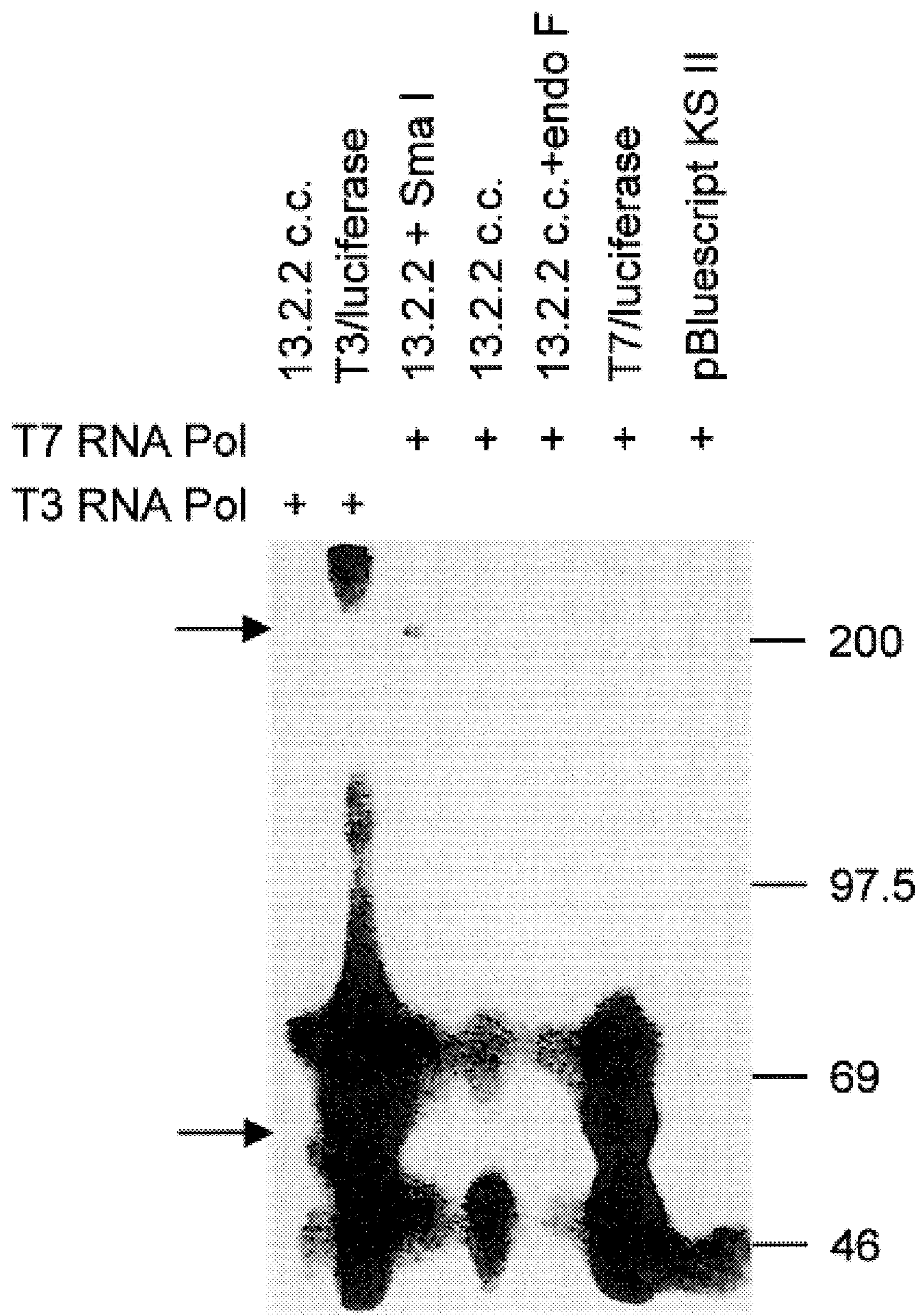

FIG. 6. Results of in vitro transcription-translation of SSeCKS cDNA.

Figure 7A:
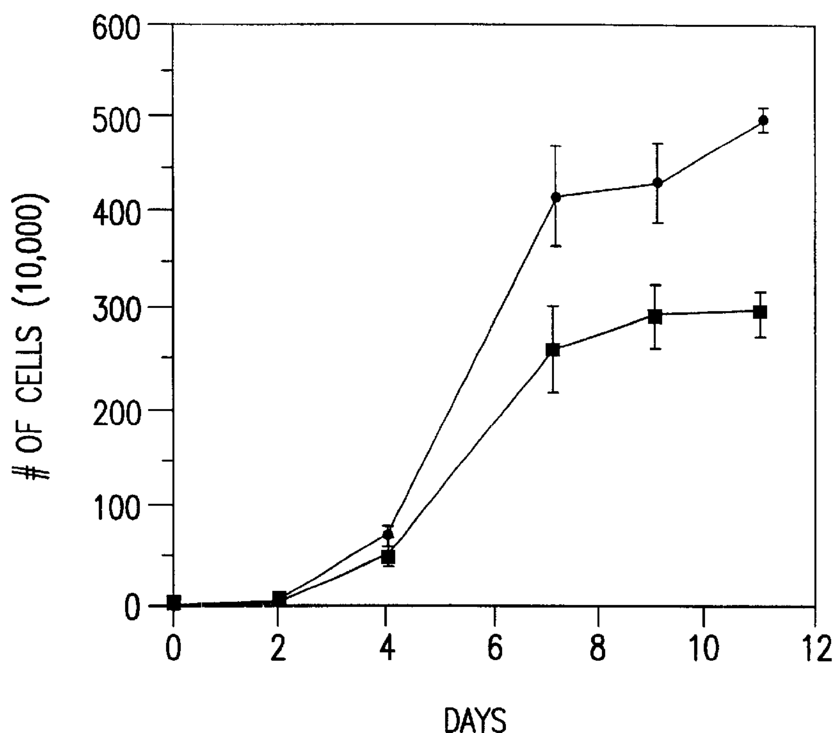
Figure 7B:
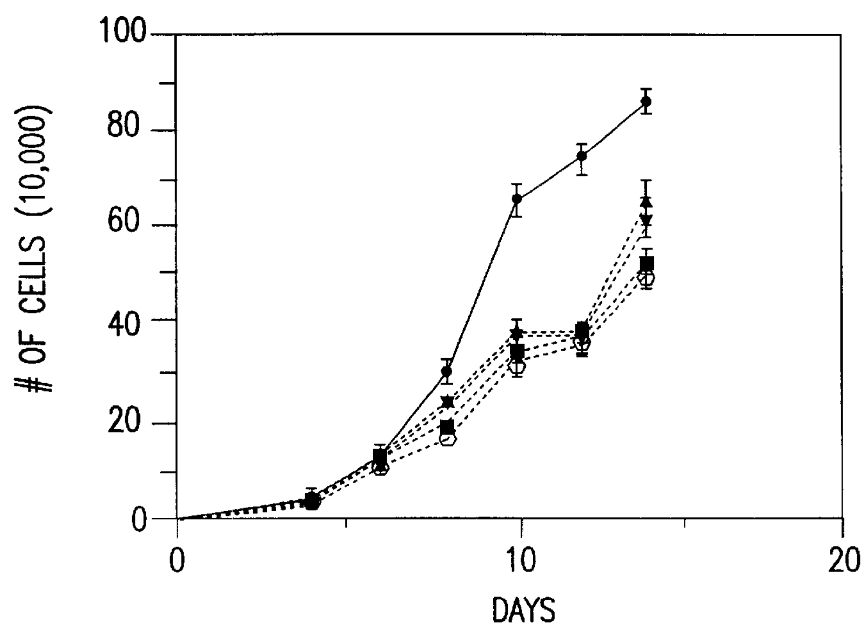

FIG. 7. Proliferation of cells overexpressing SSeCKS (A and B).

Figure 8:
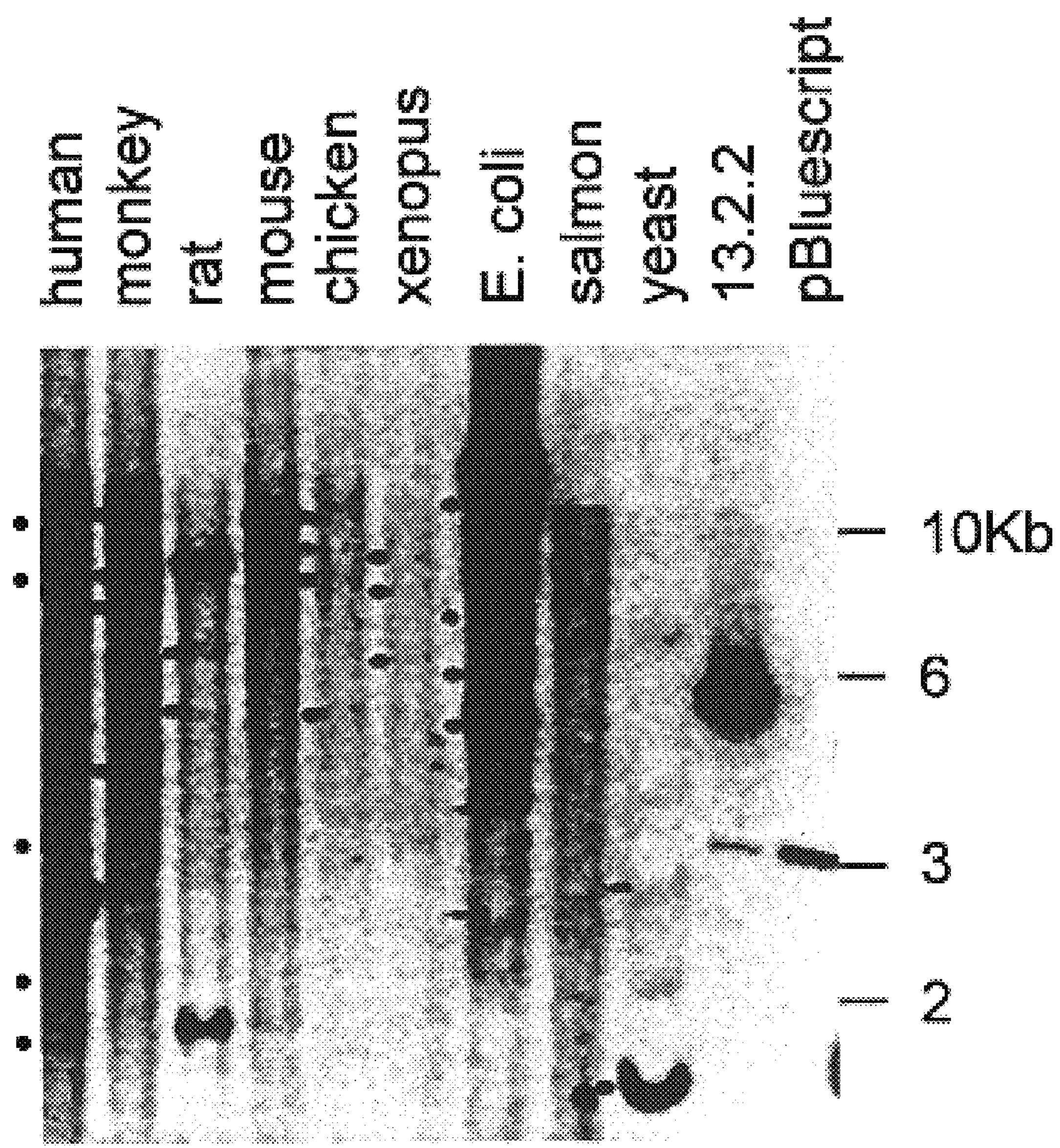

FIG. 8. "Zoo" Southern blot of SSeCKS probe to genomic DNA from various species.

Figure 9:
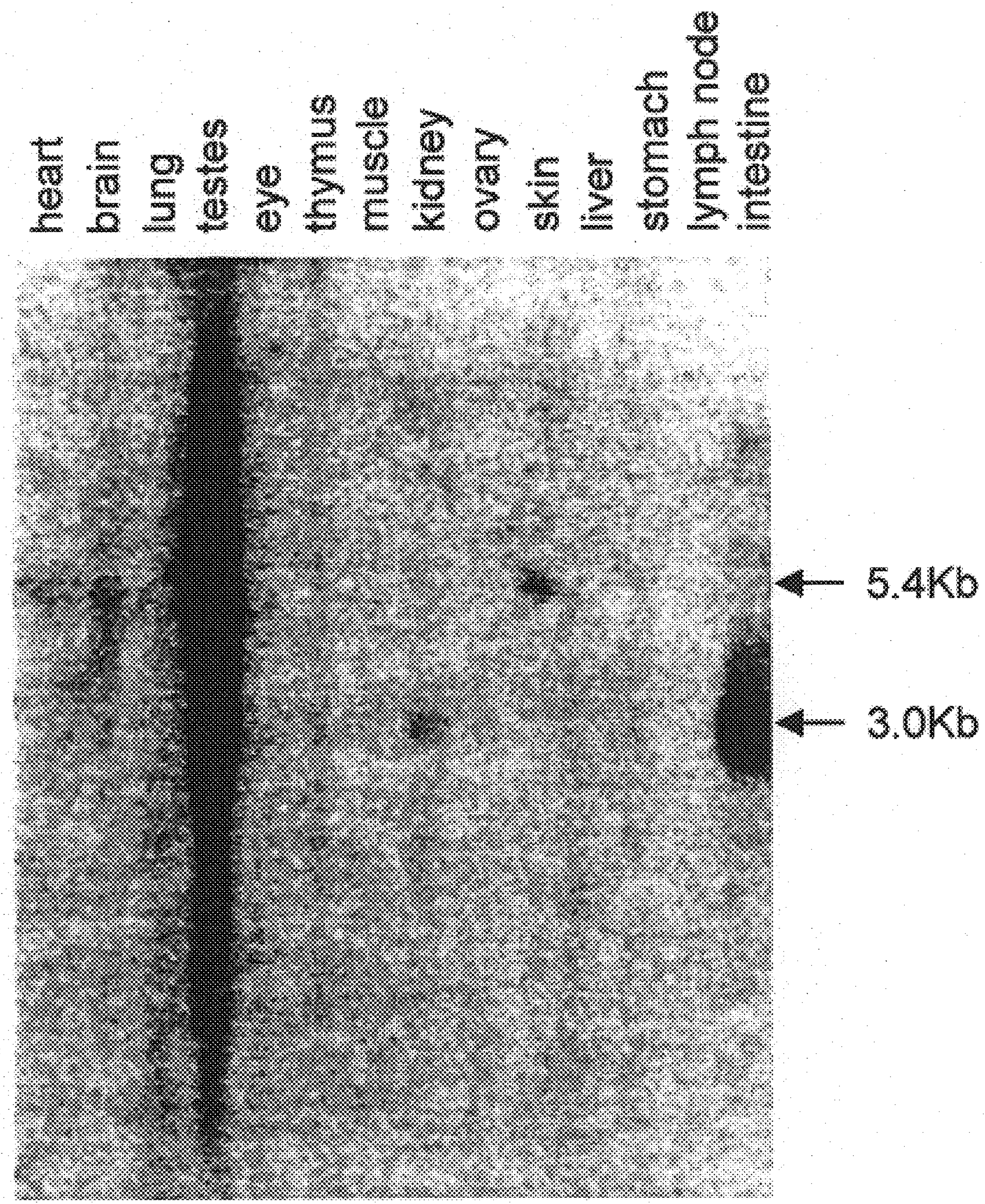

FIG. 9. Northern blot analysis showing tissue-specific expression of SSeCKS in mice.

Figure 10:
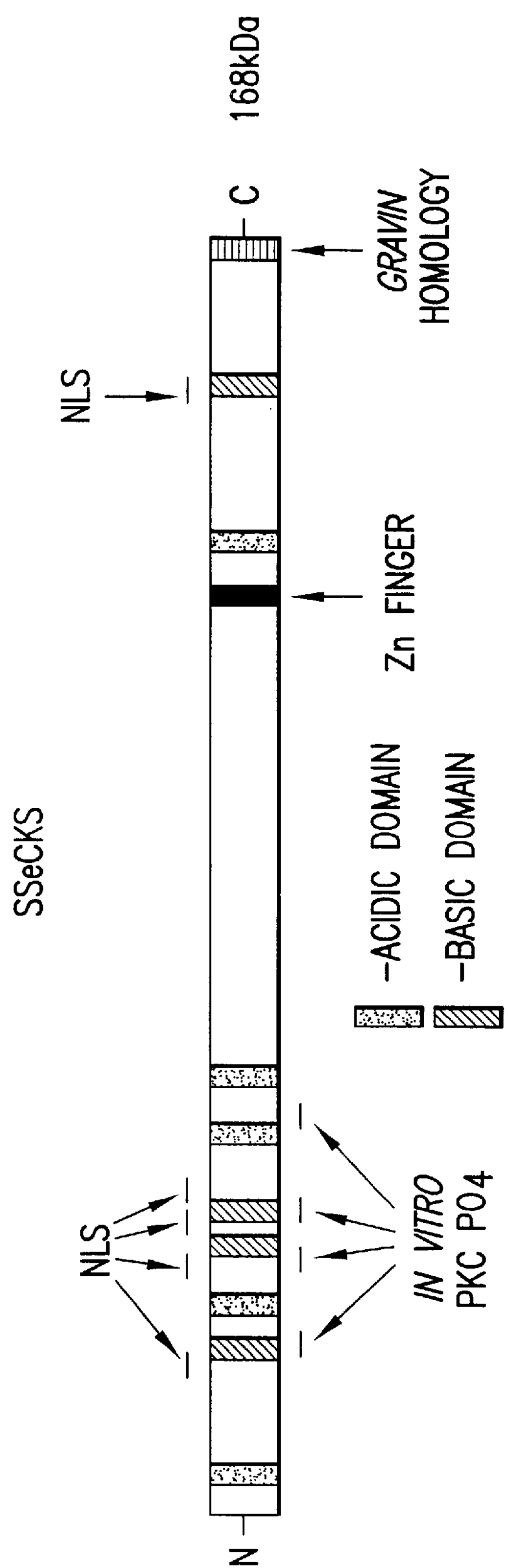

FIG. 10. Schematic diagram of SSeCKS protein.

FIG. 11A–I. Nucleic acid SEQ IN NO: 3 sequence of rat cDNA encoding full-length SSeCKS and deduced amino acid sequence.

Figure 12:
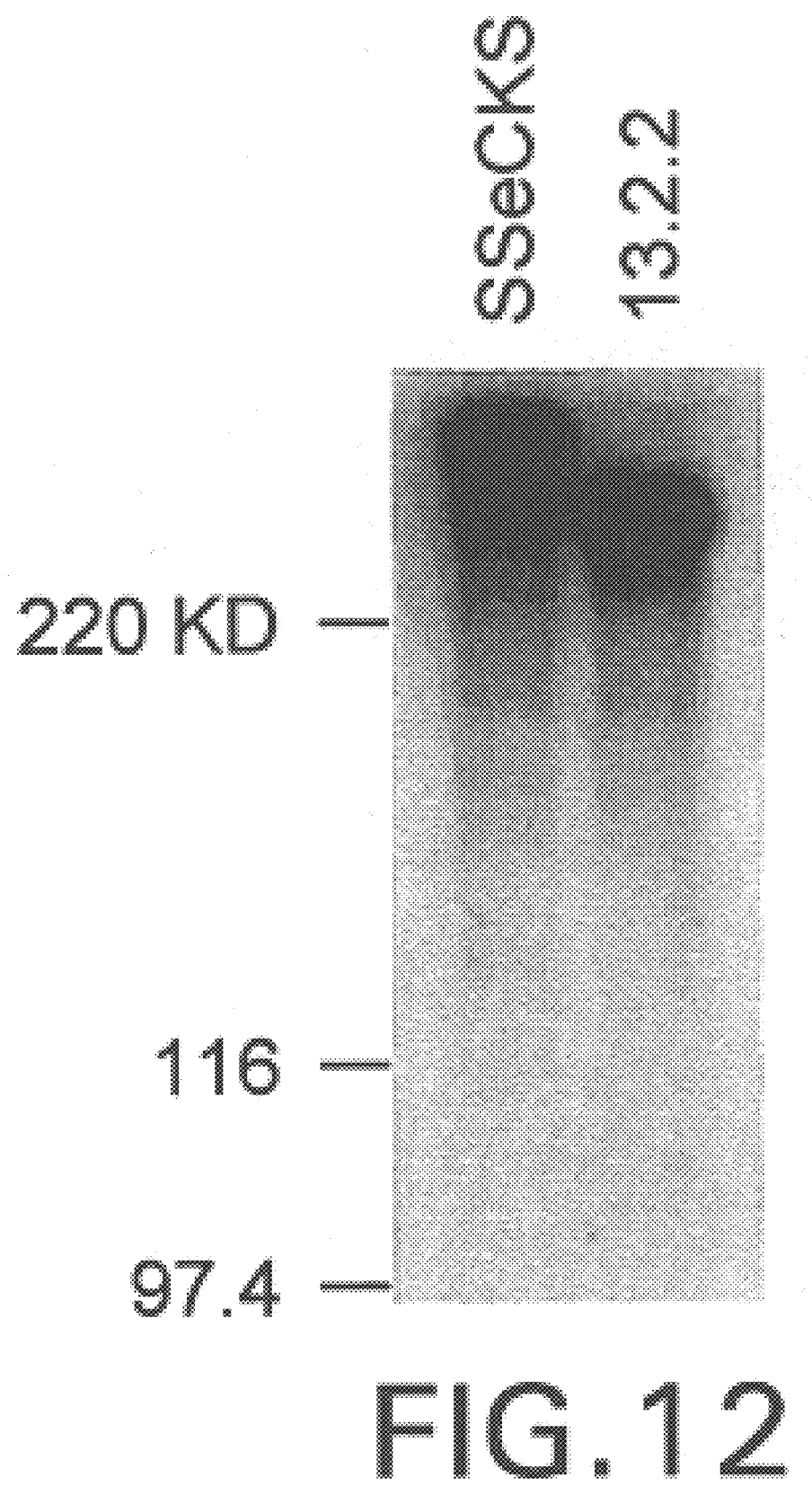

FIG. 12. In vitro transcription and translation of SSeCKS. One μg of plasmid DNA encoding the full-length SSeCKS cDNA or a N-terminally truncated SSeCKS cDNA (clone 13.2.2) were incubated in a coupled T7 transcription/translation reaction (TNT; Promega) containing [$^{35}$S]-methionine as described in section 7.1. One tenth of the labeled products were analyzed by SDS-PAGE followed by fluorography. Protein size markers are shown at left. Note that a shortened version of SSeCKS, synthesized from an internal ATG start site in clone 13.2.2, is not produced in the context of the upstream ATG start site in the full-length SSeCKS cDNA in in vitro reactions.

Figure 13A:
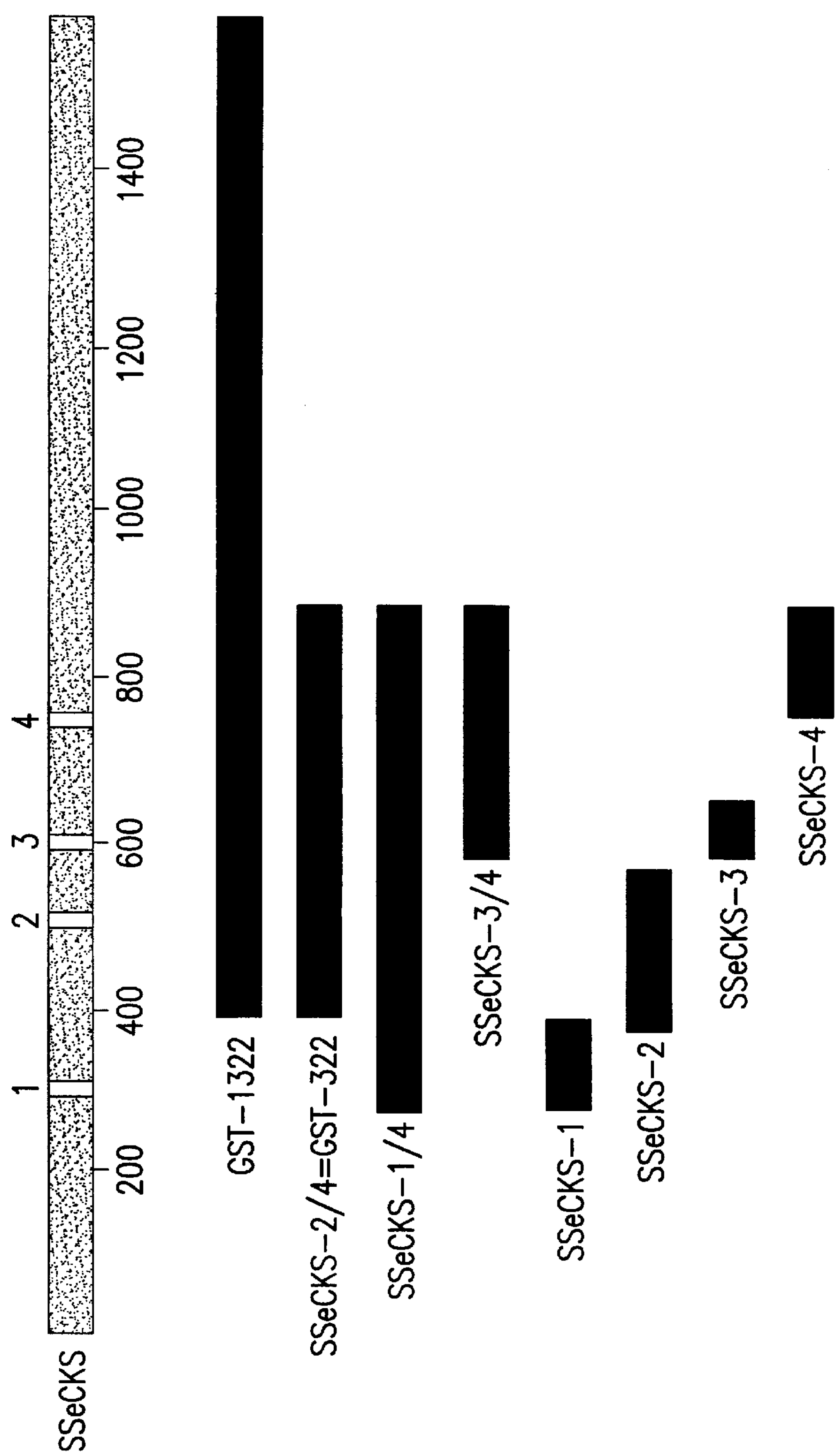
Figure 13B:
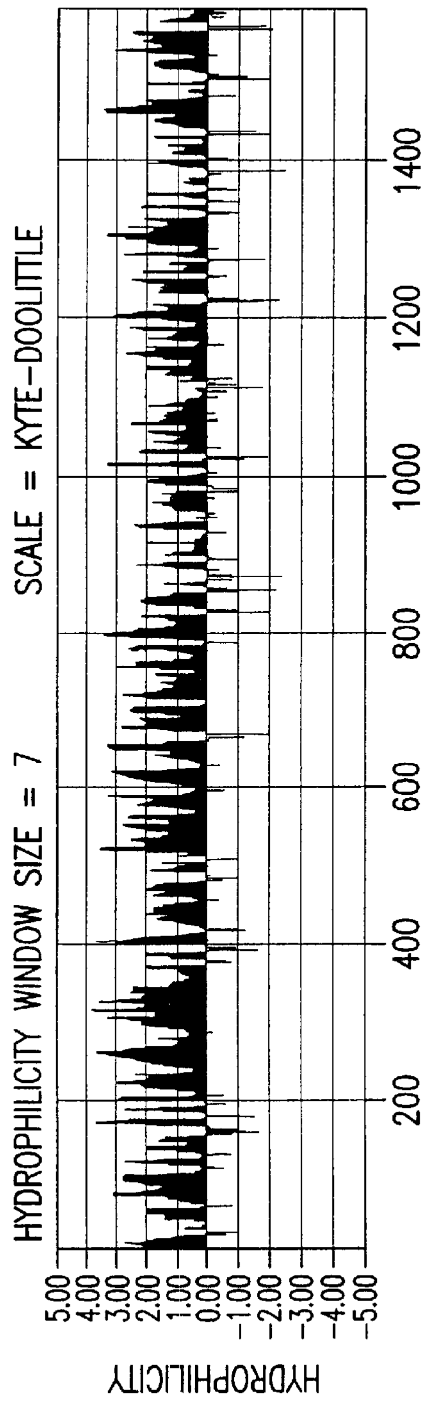
Figure 13C:
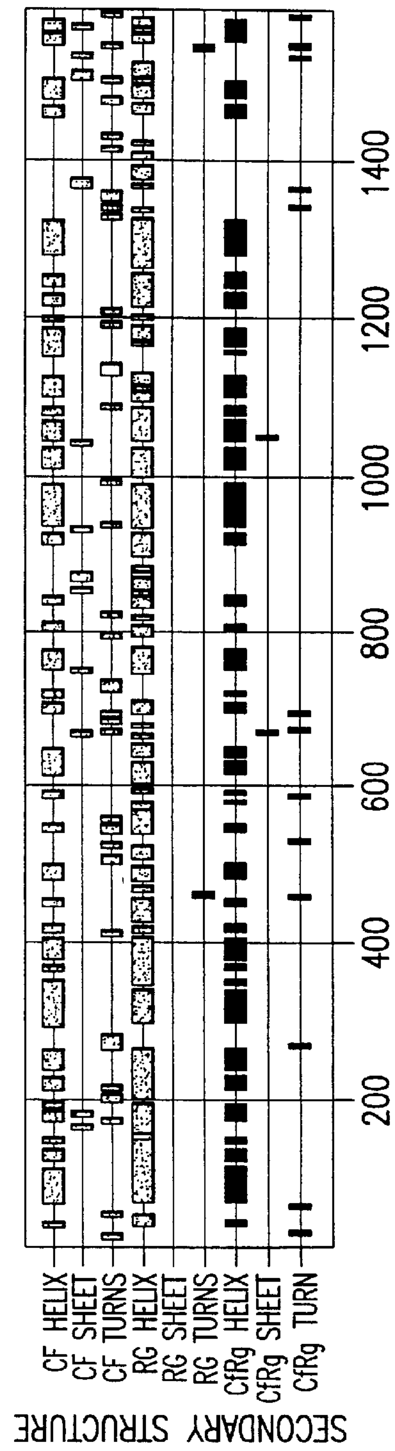

FIGS. 13A–C. Glutathione S-transferase fusion constructs of SSeCKS domains. Secondary structural analysis of SSeCKS predicted a rod-like molecule with a high degree of hydrophilicity and amphipathic helices, and a concentration of Chou-Fasman turns (Chou and Fasman, 1978, Advances in Enzymology 47:45–147) from residues 400–900 (13B and 13C). The turns in this region were not recognized by the Robson-Garnier algorithm (Garnier et al., 1978, J. Mol. Biol. 120:97–120), as shown in 13C. Four concentrations of predicted PKC phosphorylation sites ($^{B}/_{T}X^{K}/_{R}$ or $^{K}/_{R}XX^{S}/_{T}$) were also identified (13A, white boxes; numbered 1–4). The black bars (13A) indicate the sizes and names of GST-SSeCKS fusion constructs containing individual or combinations of the predicted PKC sites.

Figure 14A:
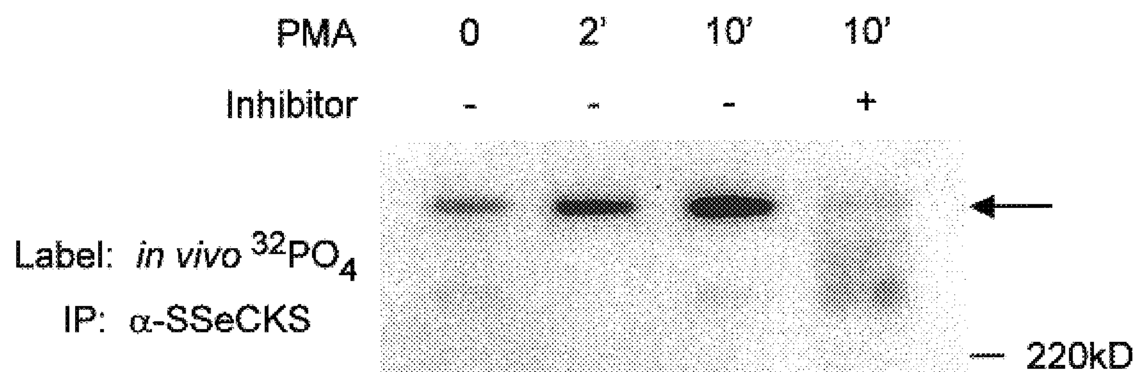
Figure 14B:
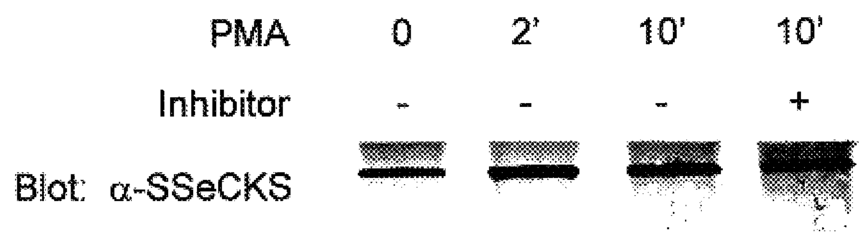
Figure 22:
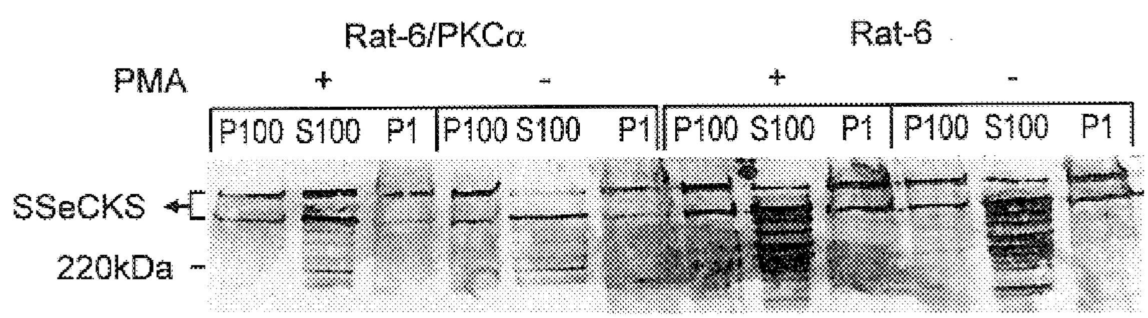

FIGS. 14A–B. In vivo phosphorylation of SSeCKS by PKC. Confluent Rat-6 cells grown overnight in DEM lacking calf serum were starved of phosphate for 2 hours and then labeled for 4 hours with [$^{32}$ P]orthophosphate. At the end of the labeling period, some cells were treated with 200 nM PMA (lane b, 2 min; lanes c and d, 15 min) and the PKC-specific inhibitor, bis-indolylmaleimide (lane d, 30 min). SSeCKS protein was immunoprecipitated from equal aliquots (400 μg) of lysates from untreated (lane a) or treated cells (lanes b–d), and western blotted onto a PVDF membrane (14A). 14B represents immunoblotting using rabbit anti-SSeCKS serum (showing equal amounts of SSeCKS protein loaded) whereas the upper panel represents autoradiography of the blotted protein (showing an increase in $^{32}PO_4$-labeling of SSeCKS following PMA treatment). The 280/290 kDa doublet (unresolved in this gel) is indicated by an arrow, and the minor 240 kDa form of SSeCKS can be detected in the upper panel. A better resolution of these SSeCKS species is shown in FIG. 22.

Figure 15A:
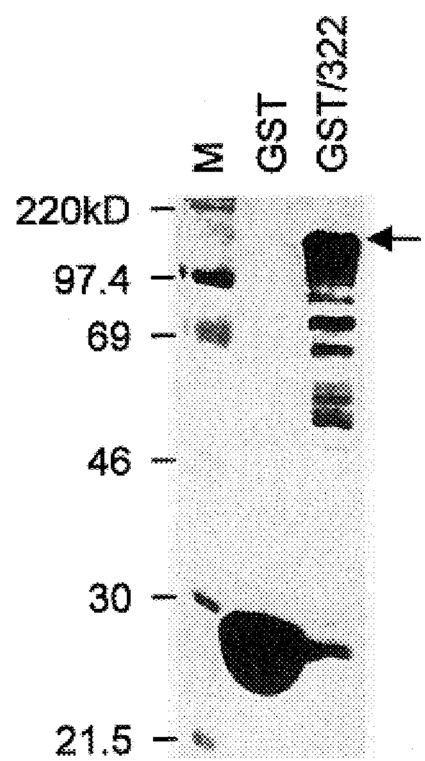
Figure 15B:
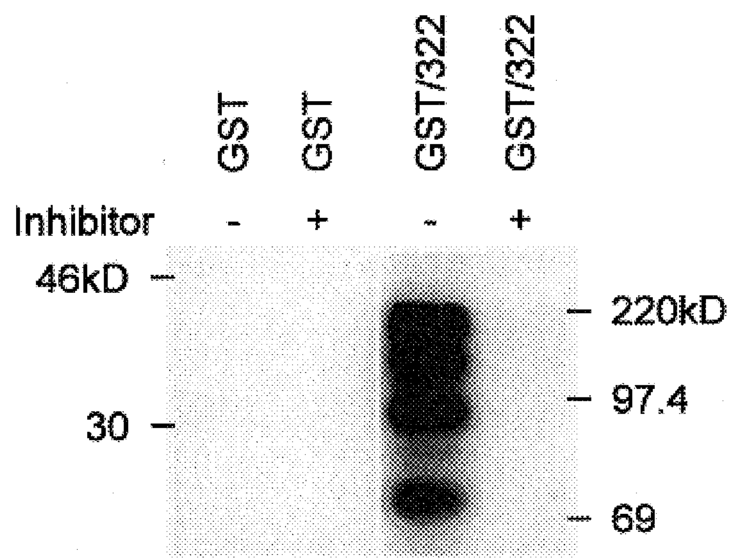

FIGS. 15A–B. In vitro phosphorylation of SSeCKS by PKC. GST and GST/322 fusion protein (see FIG. 13) were expressed and purified from bacteria as described in section 7.1 (15A). Five μg of the GST samples were added to PKC assays containing [32P]-γ-ATP in the presence or absence of the PKC peptide inhibitor (19–36). The products were then bound to glutathione-Sepharose beads, precipitated and washed, and analyzed by SDS-PAGE and autoradiography (15B). Protein size markers are indicated on the appropriate sides. Radioactive labeling was detected in GST-322 (160 kDa) only.

Figure 16A:
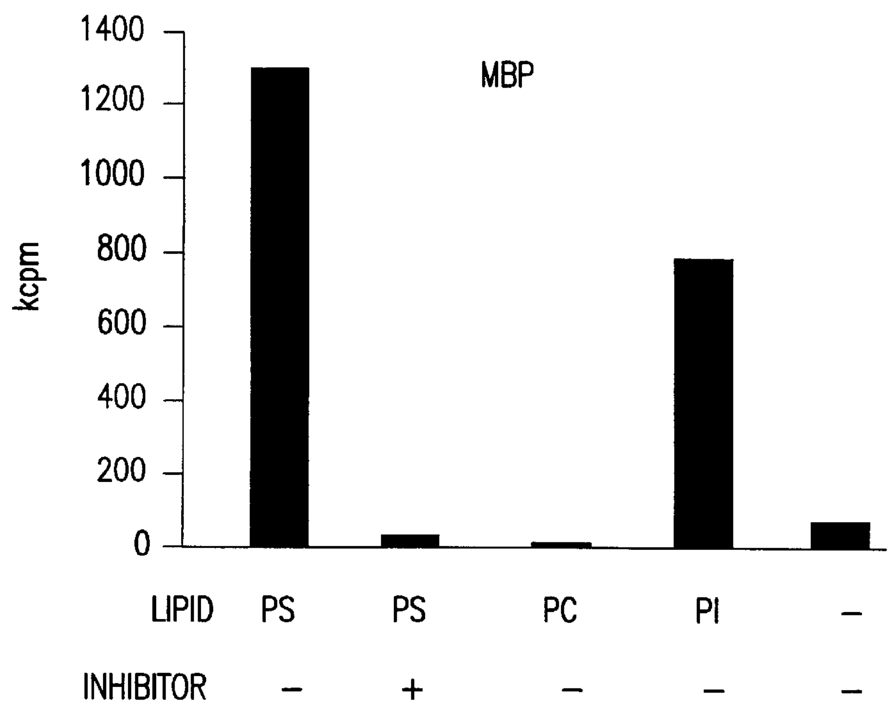
Figure 16B:
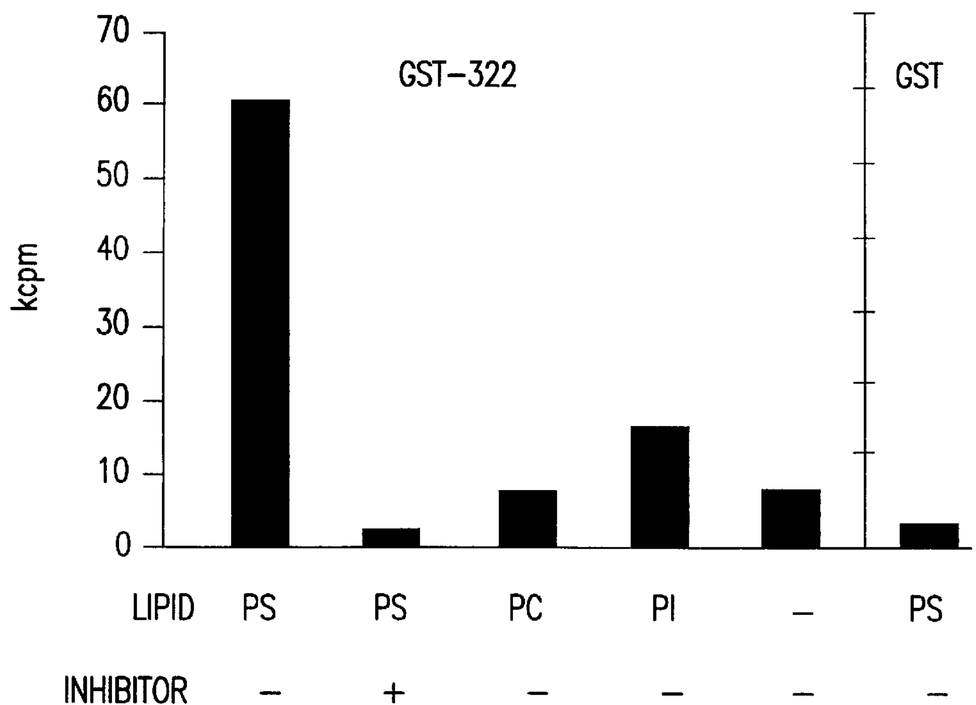

FIGS. 16A–B. Phospholipid preference for the in vitro phosphorylation of SSeCKS by PKC. Myelin basic protein, MBP (16A), GST-322 and GST proteins (16B) were phosphorylated in vitro as in FIG. 15, in the presence or absence of various lipids including phosphatidylserine (PS), phosphatidylcholine (PC) or phosphatidylinositol (PI). In some cases, excess PKC peptide inhibitor (19–36) was added as in FIG. 15. The extent of labeling in the peptide substrates was determined by spotting the reaction products on phosphocellulose discs (Whatman), precipitating peptides with washes of 5% trichloroacetic acid, followed by scintillation counting.

Figure 17A:
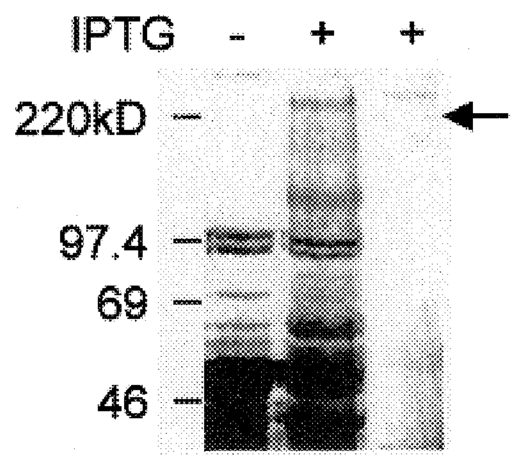
Figure 17B:
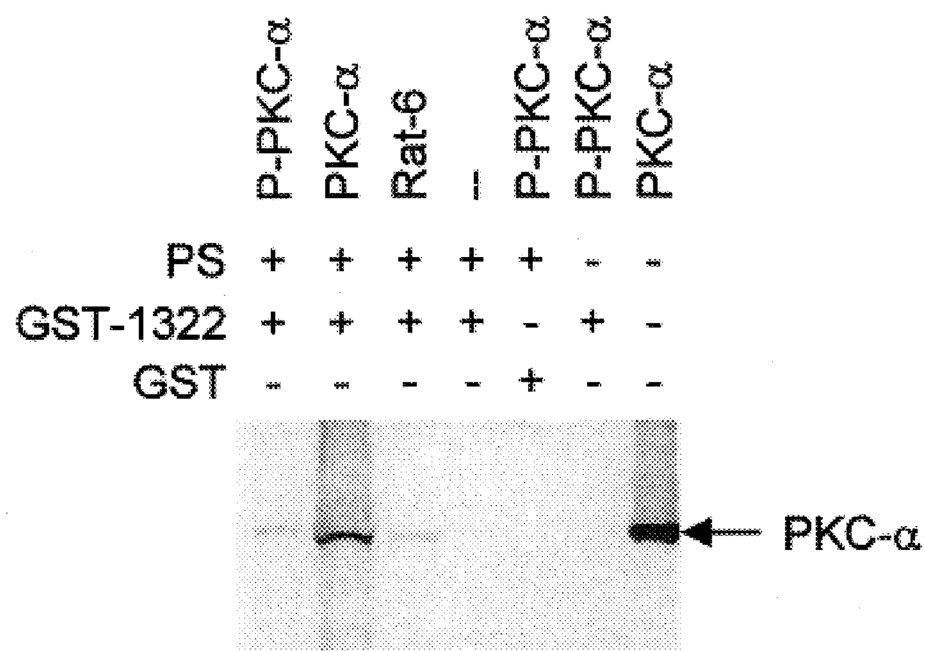
Figure 18A:
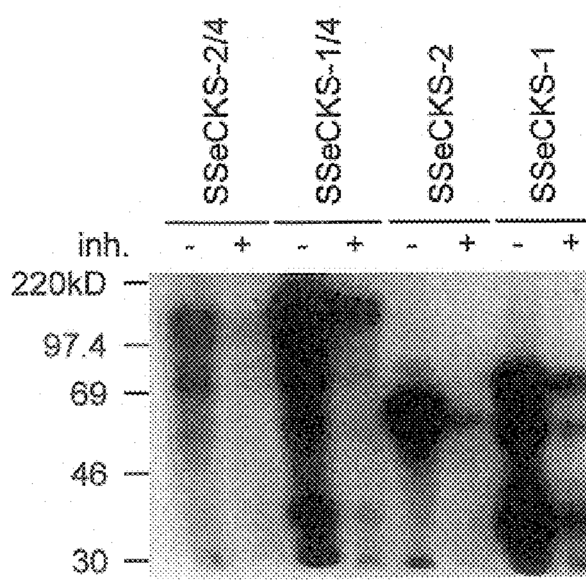
Figure 18B:
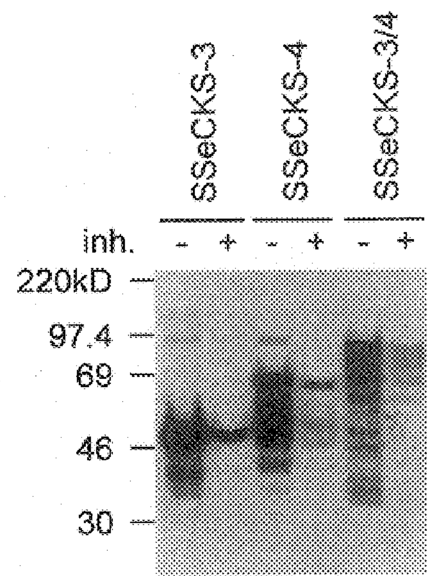
Figure 18C:
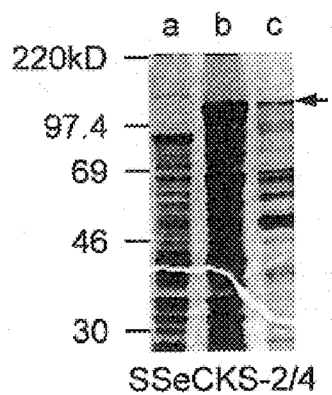
Figure 18D:
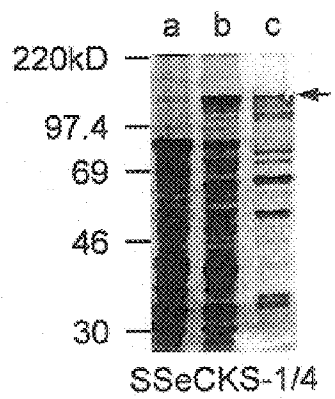
Figure 18E:
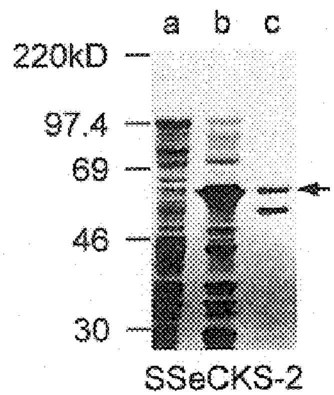
Figure 18F:
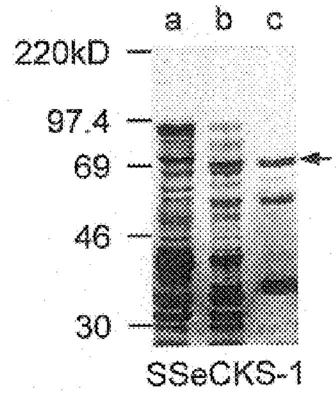
Figure 18G:
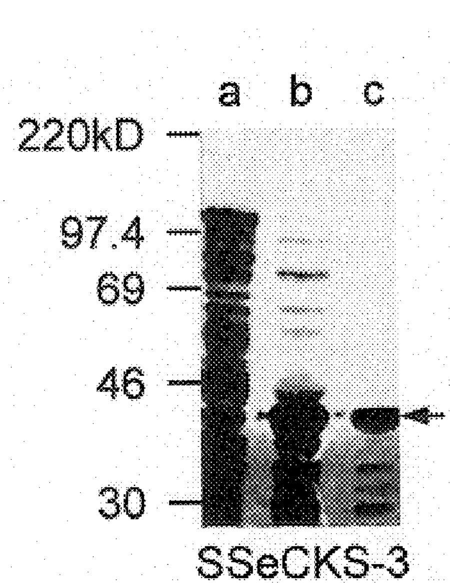
Figure 18H:
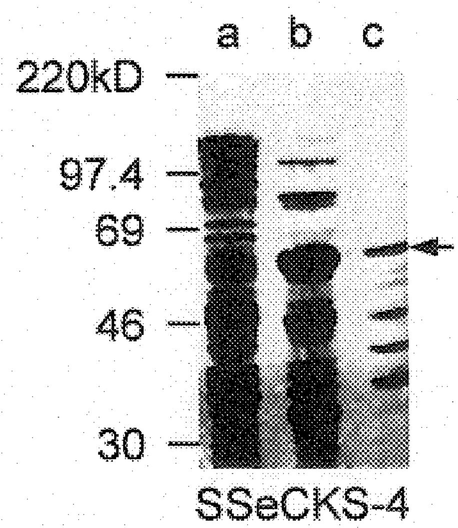
Figure 18I:
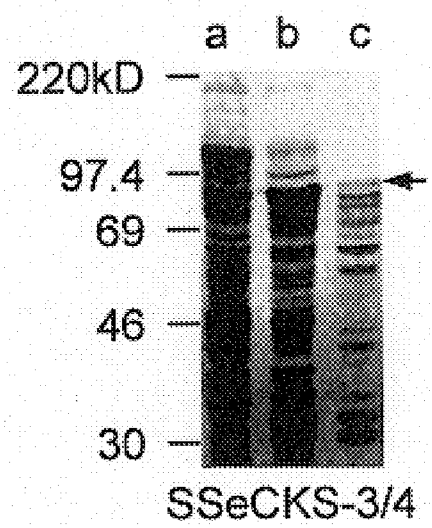

FIGS. 17A–B. Co-precipitation of SSeCKS with PKC. 17A: GST-1322 fusion protein (see FIG. 13) was expressed and purified from bacteria as described in section 7.1. 17B: RIPA lysates (1 mg protein per sample) from Rat-6 or Rat-6/PKC-α overexpressor cells, or purified rabbit brain PKC (20 ng; "P-PKC-α") were incubated for 4 h at 4° C. with fifty μg of GST-1322 (or GST alone) in the presence or absence of 0.37 mg/ml phosphatidylserine (PS). The proteins were then precipitated with glutathione-Sepharose beads, washed and western blotted as described in section 7.1. The filters were probed with MAB specific for PKC type III (UBI). The lane to the right is loaded with 20 ng of purified rabbit brain PKC-α.

FIGS. 18A–I. In vitro phosphorylation of PKC sites 1–4 on SSeCKS. 18A and 18B: Five μg of various GST-SSeCKS fusion proteins containing individual or combinations of the predicted PKC phosphorylation sites (1–4) in SSeCKS, were subjected to an in vitro PKC assay containing [32P]-γ-ATP and analyzed as in FIG. 15. 18C–F and 18G–I: Expression and purification of the GST-SSeCKS fusion proteins. Fifty μg aliquots of bacterial lysate from uninduced (lane a) or induced (lane b) bacteria, or 5 μg of GST-SSeCKS fusion protein eluted from glutathione-Sepharose columns (lane c), were analyzed by SDS-PAGE, and then stained with coomassie blue. Arrows indicate the size of the unfragmented protein product.

Figure 19:
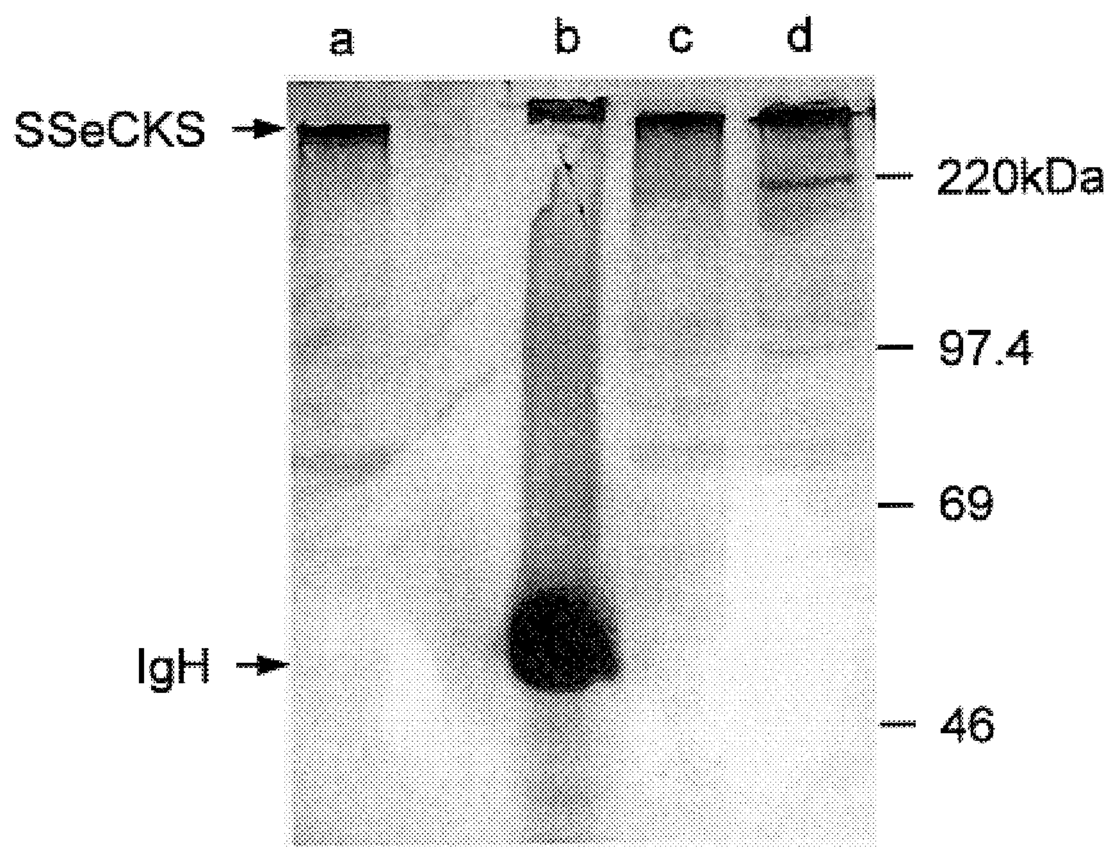

FIG. 19. SSeCKS is resistant to heat denaturation. 150 μg aliquots of Rat-6 cell lysate were boiled for 5 min in the absence of SDS and then debris removed by low speed centrifugation (1 K rpm at 4° C.). Lane c represents supernatant which was applied directly onto an SDS/polyacrylamide (5%) gel, whereas lane b was boiled supernatant first immunoprecipitated with rabbit anti-SSeCKS serum (lane b) as described in section 7.1 (IgH is immunoglobulin heavy chain recognized by the AP-labeled sheep anti-rabbit Ig secondary antibody). Lane a contains the SSeCKS protein remaining in the lysate after the immunoprecipitation in lane b. Note that under these conditions, >95% of the SSeCKS protein is usually immunoprecipitated. Lane d contains 150 μg of unboiled lysate run directly on the gel.

Figure 20:
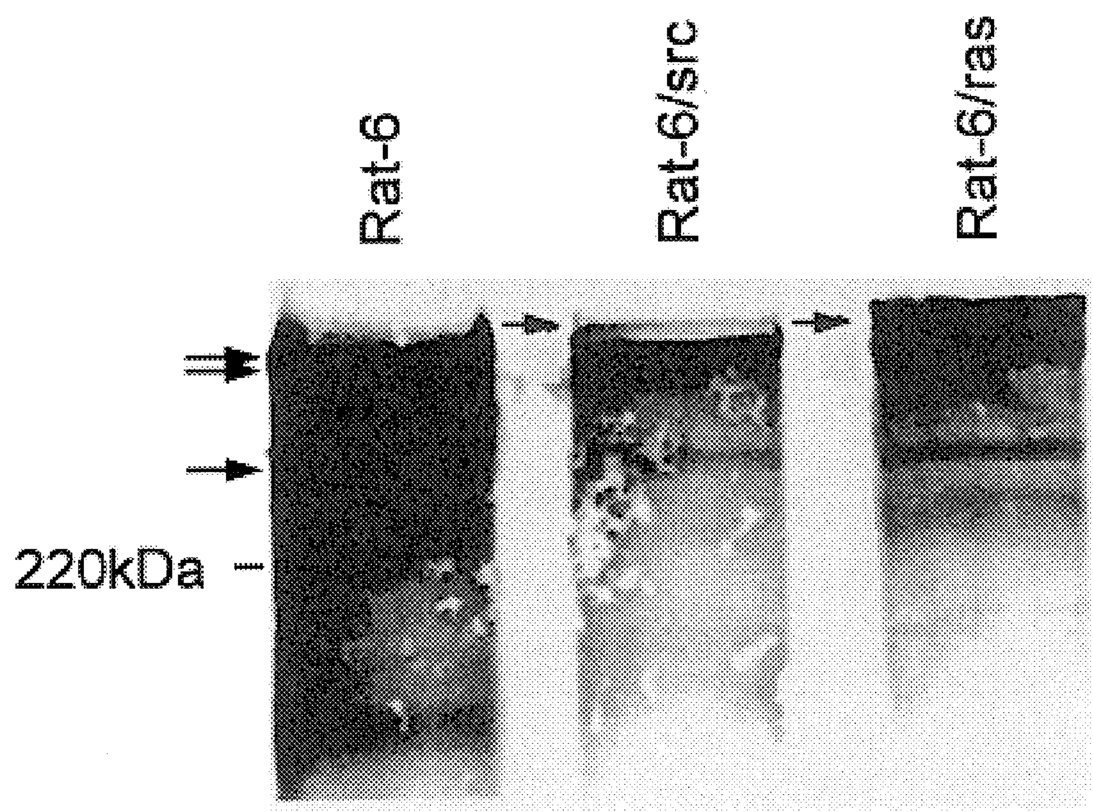

FIG. 20. SSeCKS expression in src- and ras-transformed cells. 250 μg of total protein from Rat-6, Rat-6/src and Rat-6/ras (1) cell lysates was analyzed by immunoblotting for SSeCKS as described in section 7.1. In addition to the 240 kDa (larger arrow) and 280/290 kDaa (small arrow) forms of SSeCKS found in untransformed cells, a 305 kDa form was detected in Rat-6/ras cells and to a lesser extent in Rat-6/src cells. The relative level of SSeCKS in src- and ras-transformed cells compared with Rat-6 cells (as defined by densitometry) is 15- and 8-fold lower, respectively.

FIGS. 21A–J. Immunofluorescence analysis of SSeCKS cellular localization. Subconfluent (G–J) or confluent (A–F) cultures of 3Y1 rat fibroblasts were fixed and analyzed for SSeCKS (A, C, E, H–J) or actin (B, D, F) expression as described in section 7.1. Panel G represents cells incubated with pre-immune rabbit sera. SSeCKS was present throughout the cytoplasm in subconfluent and confluent cells (e.g.-panel J, "cy"; panel A) and in the paranucleus (e.g.-panel J, "pn"). SSeCKS was also enriched in focal contact sites (e.g.-panel H, arrows), in podosomes (e.g.-panel I, "p") and at the cell edge (panel J, "ce"; panel A). Confluent 3Y1 cells showed mostly cytoplasmic staining of SSeCKS (A), possibly associated with cortical actin but not with actin stress fibers (B). After 10 min treatment with 200 nM PMA, SSeCKS moved away from plasma membrane sites towards the paranucleus (C), simultaneous with the ruffling of actin fibers at the membrane (D). The inward movement of SSeCKS and the ruffling of actin became more pronounced after 60 min treatment with PMA (E and F, respectively).

FIG. 22. SSeCKS does not enter a soluble cellular component after short-term PMA treatment. Confluent Rat-6 or Rat-6/PKC-α overexpressor cell cultures were grown overnight in DEM lacking calf serum, and then treated with PMA (1.6 μM) for 30 min or mock-treated for the same duration. The cells were lysed and spun at low speed (1.5 K rpm), yielding a pellet (P1) and supernatant (S1). The S1 component was fractionated by differential centrifugation into plasma membrane (P100) and soluble (S100subcellular components as described in section 7.1. 50 μg aliquots of P1 and P100, and 25 μg aliquots of S100 were then immunoblotted using rabbit anti-SSeCKS as in FIG. 14. The SSeCKS isomers (240, 280, and 290 kDa) are shown in relation to a 220 kDa marker protein (myosin heavy chain).

Figure 23A:
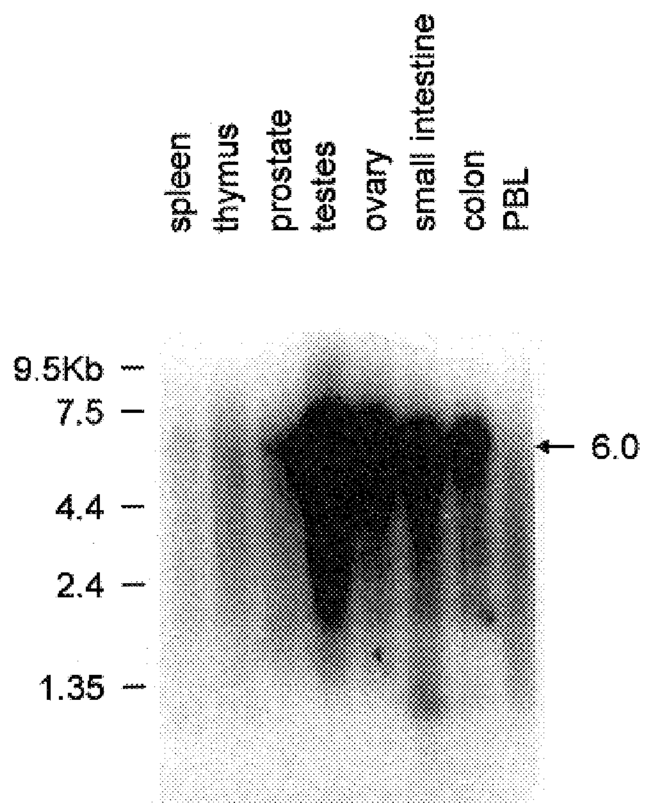

FIG. 23A. Identification of a human SSeCKS gene homologue. 2 μg of poly A+mRNA from various tissues was probed with radiolabeled rat SSeCKS cDNA under conditions of stringent hybridization. The tissue distribution and message size in humans is similar to that in mice (FIG. 9).

Figure 23B:
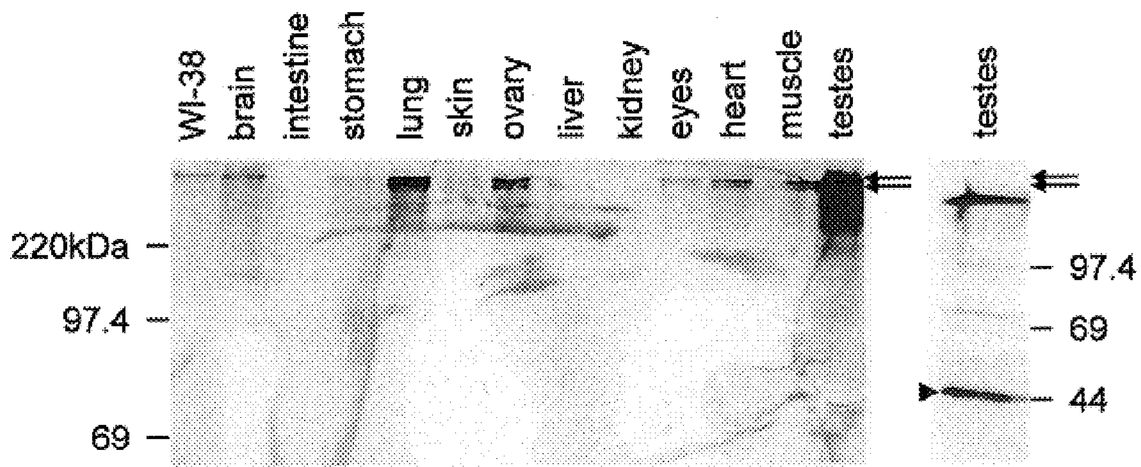

FIG. 23B. Western blot of SSeCKS expression in various mouse tissues and in human fibroblasts (WI-38) using antibody directed against rat SSeCKS protein. Note that anti-SSeCKS sera recognizes a 280/290 kDa doublet in human cells. Taken with the data in FIG. 23A, this indicates that humans encode an SSeCKS homologue.

Figure 24:
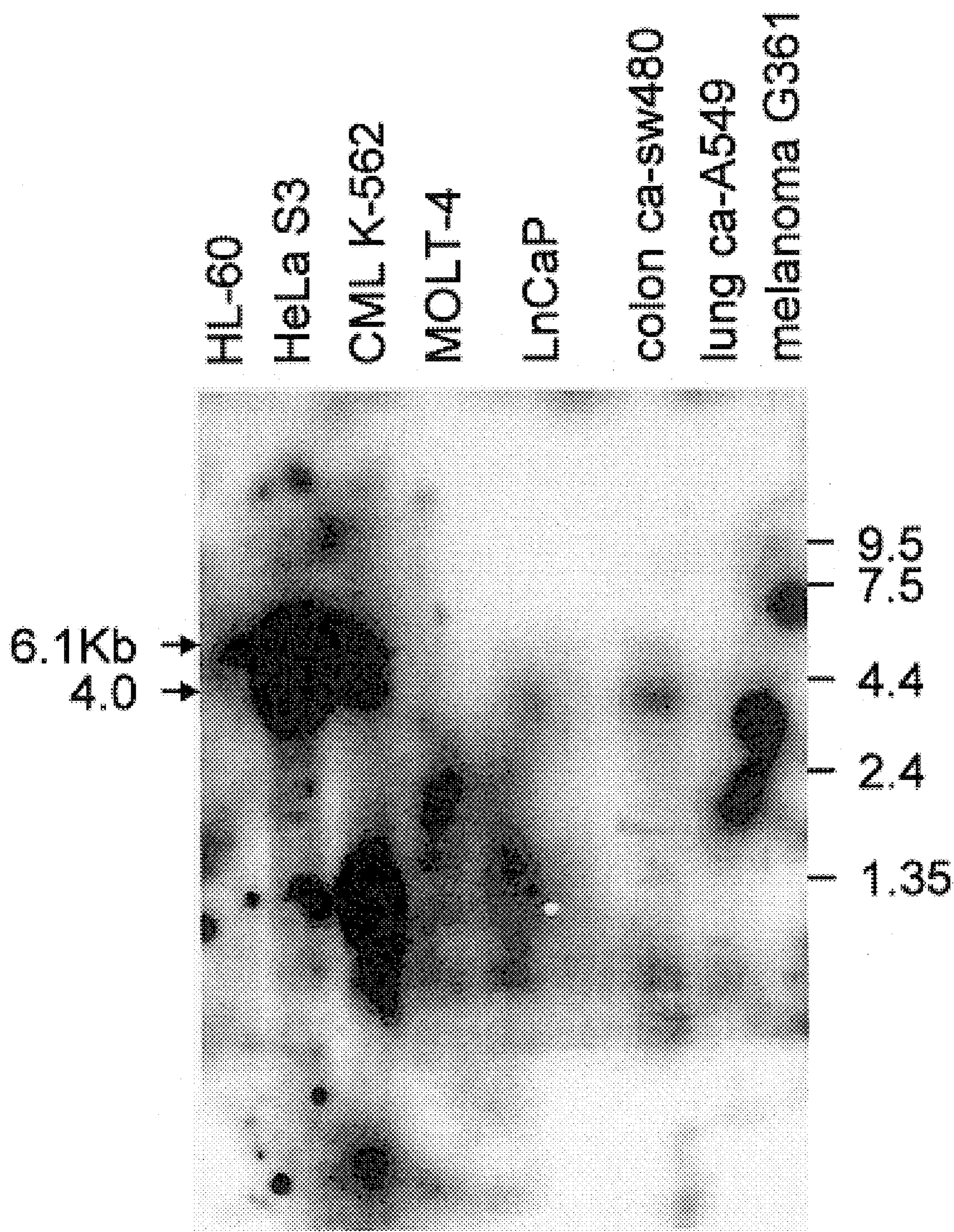

FIG. 24. Northern blot of RNA prepared from various human tumor cell lines, using radiolabeled rat SSeCKS cDNA as a probe.

Figure 25A:
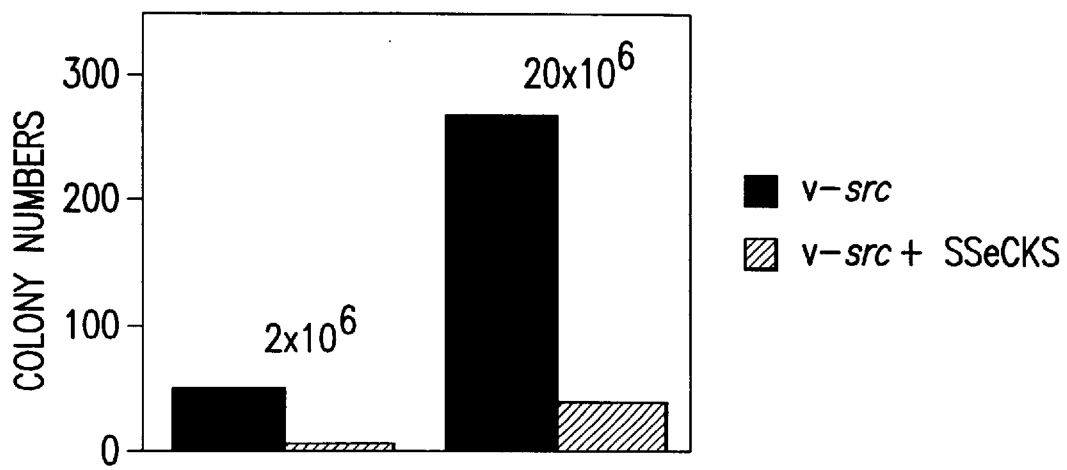

FIG. 25A and B. Full-length SSeCKS decreases v-src-induced colony formation in soft agar.

FIG. 26. Amino acid sequences associated with myristylation and palmitylation (SEQ ID NO: 5 to 10.

Figure 27:
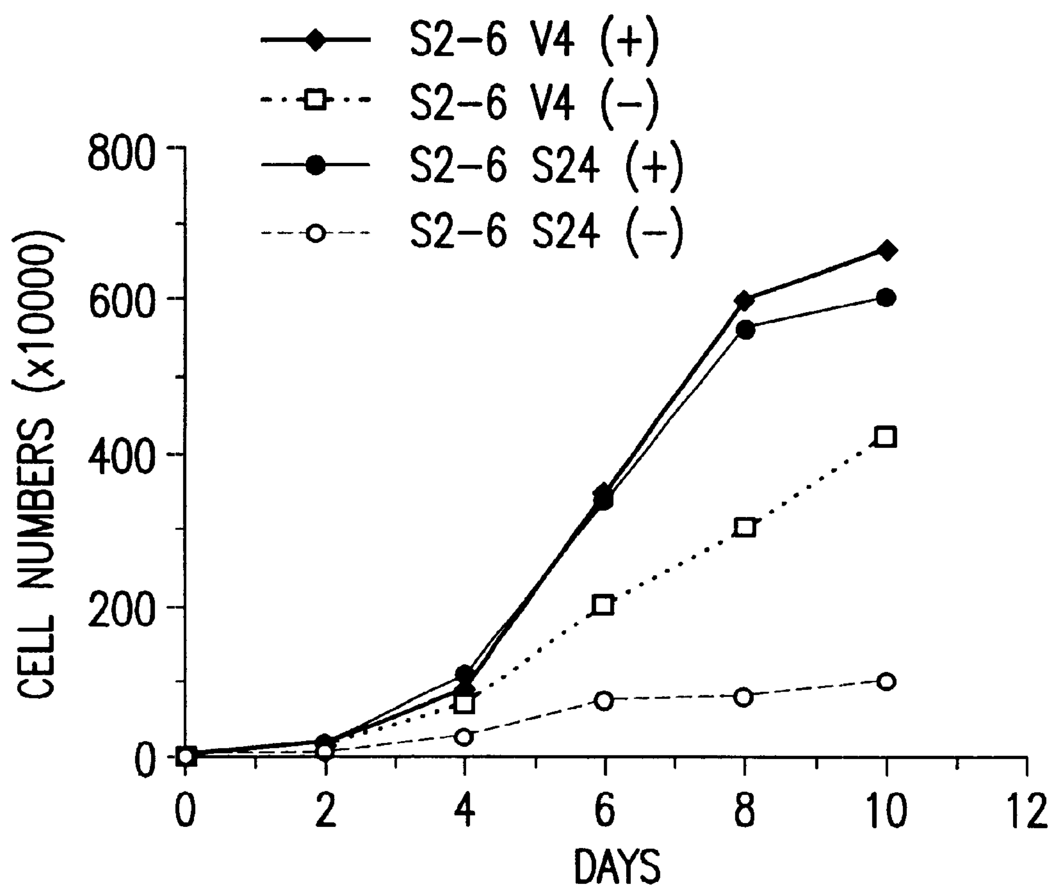

FIG. 27. Inhibition of proliferation of cells in tetracycline-containing (+) and tetracycline-free (−) media by SSeCKS, encoded by a tetracycline-repressed construct and expressed in the absence of tetracycline.

Figure 28:
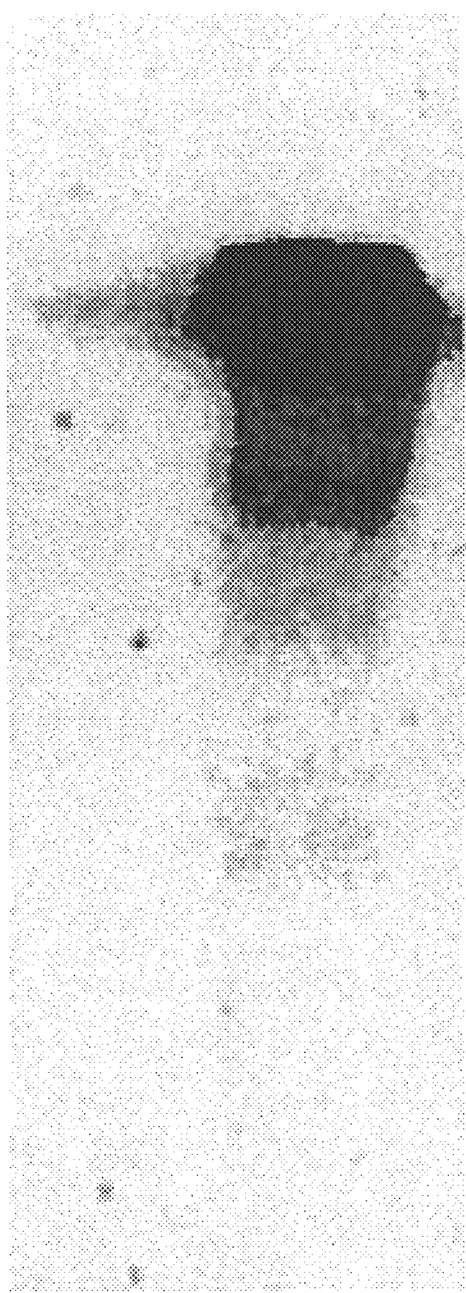

FIG. 28. Polyacrylamide gel electrophoresis (PAGE) showing labeling of SSeCKS, encoded by a tetracycline-repressed construct and expressed in the absence of tetracycline, with tritiated myristate.

Figure 29:
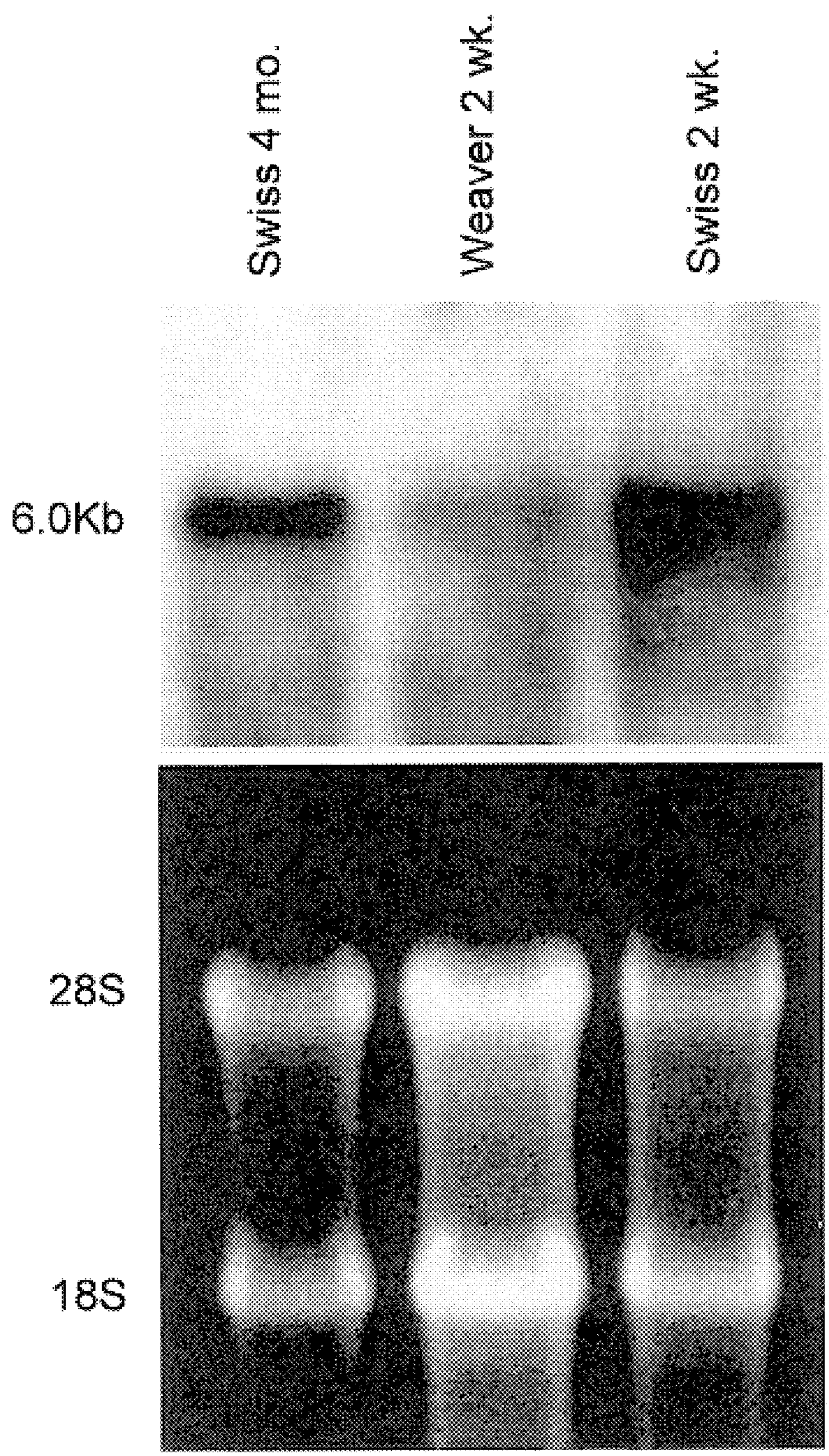

FIG. 29. Northern blot showing expression of SSeCKS RNA in the testes of normal Swiss mice and weaver mutant mice.

FIG. 30A–D. Photomicrographs showing S24 cells transfected with tetracycline-repressed SSeCKS construct in tetracycline-free (30A and 30B) and tetracycline-containing medium (30C and 30D).

FIG. 31A–D. Photomicrographs of tetracycline-repressed SSeCKS transfected S24 cells stained with fluorescent labeled antibodies to SSeCKS (31A and 31C) and F-actin (31B and 31D) in the presence (31A and 31B) and absence (31C and 31D) of tetracycline.

FIG. 32A–H. Overexpression of SSeCKS delays the formation of vinculin-associated adhesion plaques (ap). S24 cells (see FIG. 1) grown in the absence of tetracycline for 1(a,b,g,h), 3(c,d) and 4(e,f) days were stained for SSeCKS (a,c,e and g) and vinculin (b,d,f and h). After 1 day, adhesion plaques were detected only in the cell not over-expressing SSeCKS (left cell, panel a/b). After 3 days, adhesion plaques began to form in the SSeCKS overexpressor cells but were not located at the cells' leading edges (le). After 4 days, adhesion plaques were detected at the leading edge in the SSeCKS overexpressor cells. Panels g and h show the inverse expression pattern of SSeCKS and vinculin in filopodia of overexpressor (S24) and non-overexpressor cells (n).

FIG. 33A–H. Photomicrographs depicting fluorescent staining with anti-actin antibodies (33B, 33D, 33F, and 33H) or anti-SSeCKS antibodies (33A, 33C, 33E, and 33G) in cell-wounding experiments.

5. DETAILED DESCRIPTION OF THE INVENTION

The present invention relates to SSeCKS genes and proteins. For purposes of clarity of description, and not by way of limitation, the detailed description of the invention is divided into the following subsections:

(i) SSeCKS genes;

(ii) SSeCKS proteins;

(iii) additional SSeCKS molecules; and (iv) utilities.

5.1. SSeCKS Genes

In one specific embodiment, the present invention relates to a purified and isolated nucleic acid molecule having the nucleic acid sequence set forth in FIG. 11, SEQ ID NO: 3 which is the full-length rat SSeCKS cDNA. In another embodiment, the present invention relates to a purified and isolated nucleic acid molecule which hybridizes to a nucleic acid molecule having a sequence as set forth in FIG. 11 SEQ ID NO: 3 under stringent hybridization conditions. This embodiment would include nucleic acid molecules from species other than rat, such as the human SSeCKS cDNA. This embodiment would also relate to genomic DNA, RNA and antisense molecules. Stringent hybridization conditions are as described in Maniatis et al., 1982, in *Molecular Cloning: A Laboratory Manual,* Cold Spring Harbor Laboratory, Cold Spring Harbor, N.Y. In one specific, non-limiting embodiment of the invention, stringent hybridization may be performed between DNA molecules in the Southern method, in a solution of 0.75 M sodium phosphate pH 7, 1 mM EDTA, 7% SDS, 1% bovine serum albumin (BSA), and 100 microgram per ml salmon sperm DNA for 12–18 hours at 65 degrees centigrade, followed by washing twice in 50 mM sodium phosphate, 1 mM EDTA, 1% SDS, and 0.5% BSA at 65 degrees C., and twice again in the same solution without BSA at 65 degrees centigrade.

In yet another specific embodiment, the present invention relates to a purified and isolated nucleic acid molecule having the nucleic acid sequence set forth in FIG. 3 (SEQ ID NO:1), which is a truncated rat SSeCKS cDNA. In an additional embodiment, the present invention relates to a purified and isolated nucleic acid molecule which hybridizes to a nucleic acid molecule having a sequence as set forth in FIG. 3 under stringent hybridization conditions, as set forth above. This embodiment would include nucleic acid molecules from species other than rat, such as the human SSeCKS cDNA. This embodiment would also relate to genomic DNA and RNA molecules.

In related embodiments, the present invention provides for a purified and isolated nucleic acid sequence which is at least 90 percent homologous, and preferably at least 95 percent homologous, to either (i) a nucleic acid molecule having a sequence as set forth in FIG. 11 SEQ ID NO: 3 or (ii) a nucleic acid molecule having a sequence as set forth in FIG. 3. Homology may be determined using any standard software for calculating homology between nucleic acid molecules, for example, but not by way of limitation, the FASTA algorithm (Genetics Computer Group, Univ. Res. Park, Madison, Wis.; version 8.0)

The present invention also provides for nucleic acid molecules encoding either (i) a protein having an amino acid sequence as set forth in FIG. 11 SEQ ID NO: 4; or (ii) a protein having an amino acid sequence as set forth in FIG. 3 SEQ ID NO: 2.

5.2. SSeCKS Protiens

In further embodiments, the present invention provides for a purified and isolated protein having an amino acid sequence as set forth in FIG. 3 SEQ ID NO: 2 for truncated SSeCKS or in FIG. 11 SEQ ID NO: 4 for full-length SSeCKS. In related embodiments, the present invention provides for functionally equivalent proteins. For example, one or more of the amino acid residues within the sequence may be substituted with another amino acid residue of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also within the scope of the invention are SSeCKS proteins that have been modified post-translationally, including, but not limited to myristilation, phosphorylation, glycosylation, and proteolytic cleavage, or by incorporation into a larger molecule.

The present invention also provides for a purified and isolated protein encoded by a nucleic acid molecule having the sequence set forth in FIG. 3 SEQ ID NO: 1 or (i) a nucleic acid molecule which hybridizes thereto under stringent conditions or (ii) is at least 90 percent, and preferably at least 95 percent, homologous thereto. The present invention still further provides for a purified and isolated protein encoded by a nucleic acid molecule having the sequence set forth in FIG. 11 SEQ ID NO: 3 or (i) a nucleic acid molecule which hybridizes thereto under stringent conditions or (ii) is at least 90 percent, and preferably at least 95 percent, homologous thereto. The present invention also provides for functional equivalents of these proteins, as defined above.

FIG. 10 depicts a schematic diagram of the SSeCK protein, which contains several sequence motifs consistent with a role of transcriptional regulator, including a putative Zn finger, at least five nuclear localization signals, and several highly acidic domains typical of transactivation factors such as GAL4.

5.3. Additional SSeCKS Molecules

The present invention provides for vectors comprising the above mentioned SSeCKS gene nucleic acid molecules, including plasmid, phage, cosmid, and viral vectors. The foregoing nucleic acid molecules may be combined, in such vectors or otherwise, with nucleic acid sequences which may aid in their expression, including promoter/enhancer sequences and other sequences which aid in transcription, translation, or processing. Vectors of the invention may further comprise other sequences, such as selection markers, as used by skilled artisans.

The present invention further provides for the isolated SSeCKS promoter, as may be identified in a genomic clone which hybridizes to the 5' end of a nucleic acid molecule as depicted in FIG. 11 SEQ ID NO: 3. The precise location of the promoter may be analyzed by correlating the effect of site-directed deletions in nucleic acid 5' to the coding sequence with transcription of SSeCKS or a reporter gene. The SSeCKS promoter may be linked to a reporter gene and then used to study SSeCKS expression or the effects of various agents on SSeCKS expression. Because the promoter appears to be specifically inhibited in src- and ras-transformed cells, it may be used to indirectly study and identify agents that inhibit src-induced oncogenic transformation.

The present invention further provides for antibodies, including monoclonal or polyclonal antibodies, directed toward the proteins of the invention, and prepared by standard techniques known in the art.

To improve the likelihood of producing an anti-SSeCKS immune response, the amino acid sequence of a SSeCKS protein may be analyzed in order to identify portions of the SSeCKS protein molecule which may be associated with greater immunogenicity. For example, the amino acid sequence may be subjected to computer analysis to identify surface epitopes, according to the method of Hopp and Woods, 1981, Proc. Natl. Acad. Sci. U.S.A. 78:3824–3828. Such epitopes may then be isolated and incorporated into a suitable carrier molecule.

For preparation of monoclonal antibodies toward a SSeCKS protein, any technique which provides for the production of antibody molecules by a continuous cell line or by an organism may be used. For example, and not by way of limitation, the hybridoma technique originally developed by Kohler and Milstein (1975, Nature 256:495–497), or the trioma technique (Kozbor et al., 1983, Immunology Today 4:72), or other techniques used for monoclonal antibody production, including methods for producing chimeric, humanized, or primatized antibodies, may be employed.

Alternatively, polyclonal antibodies directed toward a SSeCKS protein may be prepared by methods known in the art. Various adjuvants may be used to increase the immunological response, including but not limited to Freund's (complete and incomplete), mineral gels such as aluminum hydroxide, surface active substances such as lysolecithin, pluronic polyols, polyanions, peptides, oil emulsions, and keyhole limpet hemocyanin.

The present invention further provides for nucleic acids encoding immunoglobulin molecules directed toward a SSeCKS protein, including nucleic acids encoding single chain antibodies as well as conventional antibody molecules.

Antibody molecules may be purified by known techniques, such as immunoabsorption or immunoaffinity chromatography, chromatographic methods such as HPLC, or combinations thereof.

The present invention also provides for antibody fragments directed toward a SSeCKS protein, including, but not limited to, $F(ab')_2$ and Fab fragments.

5.4. Utilities

The molecules of the present invention have a number of utilities. As described in the example section below, suppression of SSeCKS expression occurs in association with transformation by certain oncogenes or by the triggering of a proliferative cycle in starved cells by the addition of serum to the growth medium. These observations indicate that SSeCKS acts as a negative regulator of mitosis. As such, the introduction of SSeCKS gene or protein into a host cell may be used to inhibit mitosis of the host cell. Introduction may be achieved either via a vector, by physical means, or by direct uptake of the SSeCKS gene or protein into the host cell.

Moreover, it has been discovered that ectopic expression of SSeCKS suppressed the ability of v-src to induce morphological transformation and anchorage-independent growth in rodent fibroblasts. Thus, the introduction of SSeCKS gene or protein into a cell may be used to inhibit the expression of a transformed phenotype by the cell.

Since many human diseases are associated with disorders of proliferation and/or with the expression of a malignant (i.e. transformed) phenotype, increasing the levels of SSeCKS DNA, mRNA, and/or protein in a patient suffering from such a disease may be beneficial. For example, the levels of SSeCKS may be increased in a malignant tumor in such a patient in order to decrease its propensity to metastasize.

Furthermore, the level of SSeCKS expression in a cell or collection of cells may be used to evaluate the mitotic state of such cells, where a low level of SSeCKS expression may bear a positive correlation with active mitosis. Furthermore, a low level of SSeCKS expression may bear a positive correlation with a malignant phenotype. Such measurements may be used in the diagnosis or staging of tumorigenicity or malignancy, or in the assessment of the effects of therapeutic interventions in a subject in need of such treatment.

Because SSeCKS appears to be selectively expressed in testes and, to a lesser extent, brain, SSeCKS may be a marker for aberrancies in fertility and/or nervous system development. For example, decreased or absent expression of SSeCKS may be used as a marker for abnormal development of the testes or sperm in disorders of fertility.

In still further embodiments, the association between SSeCKS and cytoskeletal structures may be used to identify or treat disorders of cellular architecture. As an example, it is postulated that Alzheimer's Disease may result from defects in kinase-associated signal transduction pathways regulated by neuron-specific cellular architecture (Pelech, 1995, Neurobiol. Aging 16(3):247–256).

6. Example: Cloning and Characterization of SSeCKS cDNAs were identified whose abundance is low in NIH 3T3 cells and decreased following the expression of the activated oncogene v-src. The transcription of one such gene, SSeCKS (pronounced "ESSEX"), was found to be suppressed at least 15-fold in src, ras, and fos-transformed cells and 3-fold in myc-transformed cells, but was unaffected in raf, mos, or neu-transformed cells. Activation of a ts-v-src temperature sensitive allele in confluent 3Y1 fibroblasts resulted in an initial increase in SSeCKS mRNA levels after 1 to 2 hours followed by a rapid decrease to suppressed levels after 4 to 8 hours. Morphological transformation was not detected until 12 hours later, indicating that the accumulation of SSeCKS transcripts is regulated by v-src and not as a consequence of transformation. Addition of fetal calf serum to starved bubconfluent NIH 3T3 or 3Y1 fibroblasts resulted in a similar biphasic regulation of SSeCKS, indicating that SSeCKS transcription is responsive to mitogenic factors. Sequence analysis of a SSeCKS cDNA rat clone (5.4 kb) identified a large open reading frame encoding a 148.1 kDa product, but in vitro transcription-translation from a T7 promoter resulted in a 207 kDa product. Further, sequence analysis indicated that SSeCKS has only limited homology to known genes, including the human gravin gene, where a small amount of homology exists in the 3' untranslated region. Particular data relating to these conclusions is set forth in greater detail below.

FIG. 1 depicts the results of Northern blot analysis of SSeCKS RNA levels in NIH 3T3 cells versus NIH/v-src transformed cells. A 30 microgram amount of total RNA purified by the RNAzol method from NIH 3T3 cells or NIH/v-src cells was electrophoresed through a 1% agarose-formaldehyde gel, blotted onto Immulon N membrane, hybridized with a $^{32}$P-labelled cDNA insert containing SSeCKS sequence, washed, and autoradiographed for 3 weeks. The amount of RNA loaded was normalized by densitometric analysis of 28S and 18S RNA bands (right panel).

FIG. 2 shows that the decreased level of SSeCKS RNA in NIH/v-src cells is not due to gross deletion or translocation of the SSeCKS allele. As shown in the top panel, a 20 microgram amount of genomic DNA from NIH 3T3 or NIV v-src cells was digested to completion with EcoRI or HindIII, electrophoresed through a 0.7% agarose gel, and then blotted onto Immobilon N membrane. Fifty picogram amounts of EcoRI-cut pBluescript II KS and SSeCKS plasmid DNA were included as negative and positive controls, respectively. The blot was hybridized as described in the legend to FIG. 1, and autoradiographed for 2 days with an intensifying screen. DNA molecular size standards are shown on the left. RI refers to EcoRI, H3 refers to HindIII. The bottom panel shows the restriction map of full length SSeCKS RNA, and clone 13.2.2, isolated from a rat 3T3 library. Much of this restriction pattern is shared by both mouse and rat SSeCKS homologs, although only the rat allele contains an internal EcoRI site approximately 250 bp from the 3' cDNA terminus.

FIG. 3 SEQ ID NO: 1 depicts the nucleic acid (top line, lower case letters) and deduced amino acid (lower line, capital letters) sequence of rat SSeCKS cDNA. The largest open reading frame (from bases 176 to 4213) was identified using the TRANSLATE program from Genetics Computer Group (by J, Devereux, 1993, in Madison, Wis.). Glycine-rich domains in the N-terminus are underlined. Nuclear localization signals fitting th motif K(R/K)X(R/K) are boxed. A sequence consistent with a Zn finger from bases 3211 to 3280 is in boldface type. Two polyadenylation signals (AATAAA) in the 3' untranslated region are underlined.

Figure 4A:
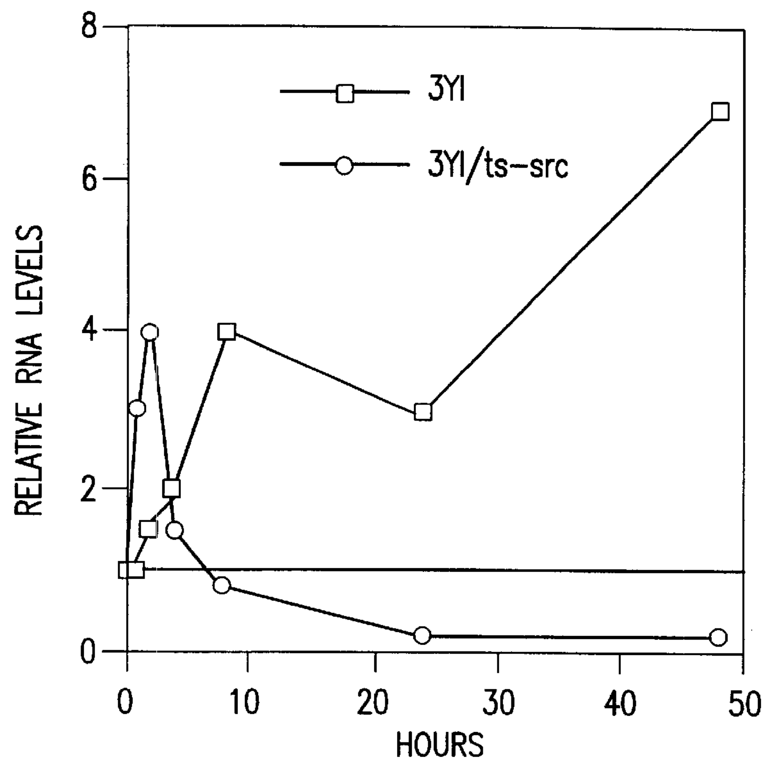
Figure 4B:
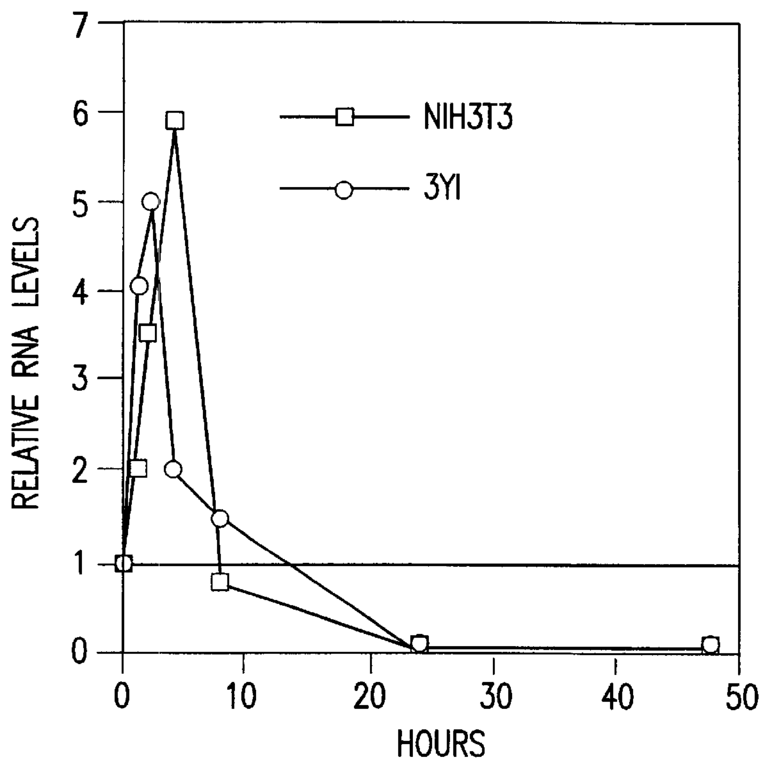

FIG. 4 shows that the transcription of SSeCKS was suppressed relatively soon after the activation of a ts-src allele or the addition of fetal calf serum (FCS) to starved rodent fibroblasts. FIG. 4A depicts the results of experiments wherein 3Y1/ts72src cells or parental rat 3Y1 fibroblasts were grown at the nonpermissive temperature (NPT; 39.5 degrees C.) for 24 hours and then shifted to the permissive temperature (PT) for v-src activity (35 degrees C.). Morphological transformation was not apparent until roughly 24 hours after the temperature downshift. The level of SSeCKS RNA dropped precipitously in the transformed cells but not their untransformed counterparts. FIG. 4B shows the results of experiments in which NIH 3T3 cells and 3Y1 cells were incubated overnight with 0.25% FCS and then with 10% FCS. Total RNA isolated at various times from each cell line was analyzed for SSeCKS transcription by Northern blot analysis using $^{32}$P-labelled SSeCKS probe. Soon after the addition of 10% FCS, the levels of SSeCKS decreased rapidly in both cell lines. The cells used for panel A were seeded at confluency at the start of the experiment whereas the cells used for panel B were subconfluent throughout the experiment.

FIG. 5 shows the results of Northern blot analyses showing levels of SSeCKS transcripts in oncogene-transformed Rat-6 fibroblasts, and demonstrates that the transcription of SSeCKS was suppressed at least 15-fold in cells transformed by src and ras and roughly 3 to 4-fold in myc-transformed cells. Each lane of the gel used to generate the blot contained 30 micrograms of total RNA from Rat-6 cells transformed with the oncogenes indicated. The rat-6 lane contains total RNA from normal control cells. The levels of SSeCKS were also found to be down-regulated 10-fold in fos-transformed cells.

FIG. 6 shows the results of in vitro transcription/translation of SSeCKS cDNA. The SSeCKS cDNA was cloned in a pBluescript II KS vector downstream of the T7 promoter, and analyzed by a coupled in vitro transcription/translation assay (TNT kit, Promega). In contrast to what was predicted, namely, a product with a molecular mass of 148.1 kDa, the 13.2.2 insert repeatedly yielded a 207 kDA product, as shown in the figure.

FIG. 7 shows the results of experiments which tested the effect of SSeCKS expression on the proliferation rates of untransformed Ω e packaging cells (NIH 3T3 background; panel A) or transformed cells (NIH/v-src; panel B) in the presence of serum growth factors. The SSeCKS cDNA (clone 13.2.2) was inserted into vector pBABEhygro, and transfected stably into the Ω e packaging cells (panel A, solid circles). Vector alone was also transfected into these cells (open circles). Proliferation of the cells containing SSeCKS cDNA or vector alone was measured and compared (FIG. 7A). The cells were grown in media supplemented with 10% CS. FIG. 7A shows that after 4 weeks of passage, the growth rate of cells containing SSeCKS cDNA was 40% lower than that of cells containing vector alone.

Filtered supernatants from these packaging cell lines were used to infect NIH 3T3, Rat-6 and NIH/v-src-cells. Although the numbers of hygromycin resistant Rat-6 colonies arising from infection with the vector were similar to those arising from infection with SSeCKS, the initial growth rates of the colonies differed significantly. After 2 weeks, Rat-6/vector colonies were 3 to 5 mm in diameter whereas the Rat-6/SSeCKS colonies contained only 20–50 cells, indicating that SSeCKS is a negative regulator of mitogenesis.

FIG. 8 depicts the results of a Southern "Zoo" blot which measured hybridization of SSeCKS probe to DNA from a variety of species, namely genomic DNA from human (derived from HeLA cells), monkey (from CV-1 cells), rat (from Rat-6 cells), mouse (from NIH 3T3 cells), chicken (from chick embryo fibroblasts), Xenopus (from oocytes), *E. coli* (strain DH10), salmon sperm, and yeast cells. FIG. 8 confirms that rat and mouse 322 sequences are highly homologous. Furthermore, SSeCKS showed partial cross-hybridization to EcoRI bands from human, monkey, chicken, Xenopus, yeast, and *E. coli* DNA.

FIG. 9 depicts the results of Northern blot analysis of SSeCKS expression in various mouse tissues. Approximately 6 kb transcripts were found to be abundantly expressed in testes, with 5–10 fold lower levels in skin, brain, and lung. A 3 kb transcript was also detected in intestines, with lower levels in kidney and stomach.

7. Example: SSeCKS is a SRC- and RAS-Suppressed Protien Kinase C Substrate Associated with Cytoskeketal Architecture

7.1. Materials and Methods

Plasmids: A full-length SSeCKS cDNA was constructed by splicing a 1.2 kB XhoI/BstEII fragment from a 5'RACE clone, p53ext2 (FIG. 11), into a BSTEII/XhoI fragment of clone 13.2.2 SSeCKS cDNA (Lin et al., 1995, Mol. Cell. Biol. 15:2754–2762). The resulting full-length SSeCKS cDNA, the nucleic acid sequence of which is set forth in FIG. 11, SEQ ID NO: 3 was sequenced using Sequenase 2.0 kits and the data submitted to Genebank in updated form. GST fusion constructs were produced using pGEX-5x-1 (Pharmacia) and His-tag constructs were produced using pET28 (Novaqen). Retro-viral constructs of the full-length SSeCKS cDNA were produced in pBABEhygro and packaged in ne cells as described in (Gelman and Hanafusa, 1993, Oncogene 8:2995–3004). The SSeCKS cDNA was also spliced into pCEV27 (Miki et al., 1991, Proc. Nat'l. Acad. Sci. 88:5167–5171) containing the Moloney leukemia virus (MLV) LTR promoter, and stably transfected into Rat-6 cells (Borner et al., 1992, J. Biol. Chem. 267:12900–12910) followed by selection on 400 μg/ml of genetic (Life Sciences) as described in (Gelman and Hanafusa, 1993, Oncogene 8:2995–3004).

Expression of GST- and His-tag fusion proteins: A fragment of the SSeCKS open reading frame (amino acid residues 389 to 894; FIG. 11 SEQ ID NO: 4 was amplified by PCR from the 13.2.2 cDNA using primers 322–13 (cDNA coordinates 1167 to 1184; FIG. 11 SEQ ID NO: 3) and 322-11 (cDNA coordinates 2725 to 2710; FIG. 11), and cloned in frame into EcoRI/XhoI-cut pGEX-5x-1 or pET28a, resulting in clones GST-322 and His-322, respectively. Another fusion product, GST-1322, was produced by PCR amplifying a 4 kb fragment from 13.2.2 cDNA using primers 322-13 and 322-36 (5637 to 5623; FIG. 11 SEQ ID NO: 3) cutting the fragment with EcoRI and BglII, cloning into pBluescript SK II (Stratagene), excising the EcoRI/SalI fragment and splicing into EcoRI/SalI-cut pGEX-5x-1. The GST fusion clones containing the "SSeCKS 1–4" protein kinase C ("PKC") phosphorylation sites were PCR amplified using the following primers, and then cloned in-frame into pGEX-5x-1: SSeCKS-1 (amino acid residues 275–390; FIG. 11 SEQ ID NO: 3), primers 322-PS5 (cDNA coordinates 825–842; FIG. 11 SEQ ID NO: 3) and M13 reverse primer for p53ext DNA template, and cutting with EcoRI/NotI; SSeCKS-2 (amino acid residues 389–552; FIG. 11 SEQ ID NO: 3), produced by an internal SacI deletion of the GST-322 construct; SSeCKS-3, primers 322-PS6 (cDNA coordinates 1758–1775; FIG. 11 ) SEQ ID NO: 3 and 322-24 (cDNA coordinates 2010–2180; FIG. 11) SEQ ID NO: 3. Additional clones include: SSeCKS-1/4, primers 322-PS5 (above) and 322-11 (above); SSeCKS-2/4. which is the same as GST-322; and SSeCKS 3/4, primers 322-PS6 (above) and 322-11 (above). The resulting clones were sequenced with Sequenase 2.0 kits and clones which lacked Taq polymerase errors were picked. BL21 (DE3)pLysS bacteria (Novagen) transformed with these plasmids were grown in LB media to OD=6 at 37° C., and then grown for an additional hour at 30° C. in LB plus 0.1 mM IPTG to induce protein expression. The pelleted bacteria were resuspended in 3 ml per gram of bacterial pellet in buffer A (50 mM Tris-HCl, pH 8.0, 1 mM EDTA, 100 mM NaCl, 1 mM NaF, 0.5 mM sodium vanadate, 2 μg/ml each of trasylol, leupeptin, antipain, pepstatin A and 1 mM PMSF) and lysed by 3–5 cycles of freeze-thawing. Debris was removed by centrifugation for 10 minutes at 3 K (4° C.). This was followed by the sequential addition of 4 mg deoxycholic acid per gram of bacterial pellet (while stirring, until viscous), $MgSO_4$ to a final concentration of 5 mM, and then 300U benzonase (Boehringer Mannheim). After 30 minutes incubation on ice, the lysate was checked for loss of viscosity using a pasteur pipette. Debris was then pelleted by centrifugation at 16 K for 15 minutes at 4° C. The supernatant was applied to either a glutathione-Sepharose column (Pharmacia) or a $Ni^{2+}$—Sepharose column (Qiagen). The column beds were washed according to the manufacturer's specification, and the bound protein was eluted with 3 washes of either glutathione (15 mM) or imidazole (250 mM) for the GST or His-tag proteins, respectively. The purity of the proteins was determined by electrophoresis on 6% SDS-polyacrylamide stacking mini-gels followed by Coomassie blue staining, and it the case of GST proteins, by Western blotting (Gelman and Hanafusa, 1993, Oncogene 8:2995–3004) onto Immobilon-P (Millipore) and probing with rabbit anti-GST sera. Protein concentrations were determined using BioRad assay reagent (Bradford).

Production of immune sera: After approximately 10 ml of pre-immune sera was obtained, two New Zealand giant rabbits were immunized with 150 μg each of GST-1322 protein emulsified with an equal volume of complete Freund's adjuvant (Life Technologies). The rabbits were boosted 2–3 times more with 50–100 μg/injection of GST-1322 in incomplete Freund's adjuvant. The specificity of the sera was determined by probing slot blots containing GST protein alone, GST-1322, $His_6$-1322, and BL21 lysate alone, followed by incubation with alkaline phosphatase-labeled sheep anti-rabbit Ig (boehringer-Mannheim), washing in Western blot buffer (below), and developing with BCIP/NCP (Promega). Both rabbits gave high titers (>5000) of anti-SSeCKS antibodies. Immunoaffinity-purified anti-SSeCKS antibodies were isolated as follows: Glutathione-Sepharse columns were saturated with either GST or GST-1322, washed and then treated with 25.5 mM dimethyl pimelimidate cross-linker (Pierce). 10 ml of RB anti-SSeCKS sera was passed repeatedly over the GST column (the bound antibodies were eluted with glutathione after each round) until all the anti-GST reactivity (as determined by slot-blot Western analysis) was removed. The resulting sera was passed over the GST-1322 column, and the bound antibodies were eluted with Tris-glycine buffer, pH 2.8, as described in (Sambrook et al., 1989, Molecular Cloning: A Laboratory Manual, 2nd Ed., Cold Spring Harbor Laboratory Press, Cold Spring Harbor, N.Y.). This fraction was shown by slot blot Western analysis to retain GST-1332 and $His_6$-1322 binding at dilutions of 1:1000, and no cross-reactivity to GST protein alone at dilutions of 1:100.

In vitro transcription/translation of SSeCKS: Plasmid DNAs (1 $\mu$g) containing either the full-length SSeCKS cDNA or the 5.4 kb 13.2.2 cDNA cloned into Bluescript SKII were linearized at the 3' ends of the cDNA inserts (SMAI) and incubated at 30° C. for 90 minutes in a 50 $\mu$l coupled transcription/translation reaction (TNT; Promega) containing 50 $\mu$Ci of translation-grade [$^{35}$S] methionine (New England Nuclear), according to the manufacturer's specification. 5 $\mu$l of the resulting protein products were electrophoresed on a 6% SDS-polyacrylamide stacking gel (above). The gels were fixed in methanol/acetic acid (15%/7%, respectively), incubated in Amplify (Amersham) and fluorographed with Kodak XAR film at −70° C.

In vitro PKC phosphorylation assay: PKC assays were variations of assays described in (Kobayashi et al., 189, BBRC 159:548–553). Briefly, 40 $\mu$l reactions contained 10 $\mu$l of 0.3 mg/ml of the target polypeptide, 10 $\mu$l of 1 $\mu$Ci/,251 [$^{32}$P]ATP (new England Nuclear), 10 $\mu$l rabbit brain PKC enzyme (10–25 ng), and 10 $\mu$l of 4× buffer (20 mM Tris-HCl, pH 7.5, 0.1 mM $CaCl_2$, 5 mM $MgCl_2$, 0.03% Triton X-100, and freshly added 0.31 mg/ml L-α-phosphatidyl-L-serine [PS], 0.06 mg/ml 1,2-dileoyl-rac-glycerol, and 0.4 mM ATP) were incubated for 30 minutes at 37° C. Target proteins included various GST-SSeCKS products, PKC substrate peptide[Ser$^{25}$]PKC[19–31], and the PKC substrate peptide ac-Myelin Basic Protein [4–14] (the latter two from Life Technologies). A PKC-specific inhibitor (pseudosubstrate) peptide PKC[19–36] (life Technologies) was used at 0.15 $\mu$M. 10 $\mu$l of phosphorylated product was analyzed using SDS-PAGE as described above.

In vivo phosphorylation analysis: $10^6$ Rat-6 cells were incubated overnight in DEM (Bio-Whittaker) supplemented with 0.5% calf serum (Life Technologies) and then twice for 1 h in DEM without sodium phosphate (Life Technologies). Labeling was for 2 hours in MEM without phosphate supplemented with 0.5% calf serum (Life Technologies) and then twice for 1 h in DEM without sodium phosphate (Life Technologies). Labeling was for 2 hours in MEM without phosphate supplemented with 150 $\mu$Ci of [$^{32}$P] orthophosphate (New England Nuclear). In some case, phorbol 12-myristate 13-acetate (PMA; 200 nM) was added for various durations at the end of this labeling period. The PKC-specific inhibitor, bis-indolylmaleimide (Boehringer Mannheim; 10 $\mu$M), was added at the beginning of the labeling period and again when PMA was added. After washing the cells thrice with ice-cold PBS, the cells were lysed in 0.5 ml RIPA/150 mM NaCl and analyzed by SKS-PAGE as described above.

Western (immuno-) blot analysis: Cells were washed thrice in ice-cold phosphate buffered saline (PBS), lysed in 1 ml/10 cm plate with RIPA buffer containing 150 mM NaCl (Gelman et al., 1993, Oncogene 8:2995–3004), vortexed, incubated on ice for 10 min, and then centrifuged at 13K for 30 min at 40 to remove debris. 50–400 $\mu$g of cell lysate was electrophoresed through 6% SDS-polyacrylamide stacking gels, and then electrophoretically transferred to Immobilon-P. A rapid immunodetection method was followed (M. A. Mansfield, Millipore Corp.; personal communication) in which dried blots were not re-wetted, and then processed as described previously (Gelman, et al., 1993, Oncogene 8:2995–3004) using PBS containing 1% non-fat dry milk (Difco) and 0.05% Tween-20 (Sigma) as the buffer. Alkaline phosphatase-labeled secondary antibodies were either sheep anti-rabbit Ig or sheep anti-mouse Ig (Boehringer Mannheim), and the substrate was room-temperature stabilized BCIP/NCP solution. Protein concentrations were determined using a Micro BCA Protein Assay Kit (Pierce).

Co-precipitation (pull-down) assay: 1 mg of lysate from Rat-6 or Rat-6/PKCα overexpressor cells (gifts of I. B. Weinstein, Columbia University) (Borner et al., 1995, J. Biol. Chem. 270:78–86), or 20 ng of purified rabbit brain PKC (Upstate Biologicals, Inc.) were co-incubated with 135$\mu$l of glutathione-Sepharose pre-bound to 50$\mu$g of GST-1322 for 4 h at 4° C. (rotating) in RIPA buffer containing 150 mM NaCl, 5 mM $MgCl_2$. PS was added in some cases at 0.37 mg/ml. The pellets were washed thrice and then analyzed by SDS-PAGE and immunoblotting as described above using mouse monoclonal (MAb) anti-PKC type III (Upstate Biologicals, Inc.)

Subcellular fractionation of plasma membrane and cytosol components: $10^6$ Rat-6 or Rat-6/PKCα over-expressor cells were washed thrice in ice-cold Tris-Glu buffer (25 mM Tris-HCl, pH 7.4, 150 mM Nacl, 5 mM KCl, 1 mM sodium phosphate, 0.1% glucose). The cells were scraped into Tris-Glu, and pelleted by centrifugation at 1.5K for 5 min. The cells were swollen on ice for 10 min in 20 mM Tris-HCl, pH 7.4., 10 mM KCl, 1 mM EDTA, 1 mM DTT, 1% trasylol and 1 mM PMSF. The cells were dounce homogenized (40 strokes with pestle B), and then NaCl was added to a final concentration of 100 mM. The nuclei and cell debris were pelleted at 1.5K for 10 min. (4° C.) yielding initial pellet (P1) and supernatant (S1) fractions. The S1 fraction was loaded into polycarbonate tubes and centrifuged in a SW41 rotor (Beckman) for 30 min. at 100,000 g, yielding a secondary pellet (P100), containing plasma membranes, and supernatant (S100). Aliquots of these fractions were analyzed by SDS-PAGE and immunoblotting as above.

Immunofluorescence analysis: Rat-6 cells were seeded onto sterile 22 $mm^2$ coverslips at a density of roughly 70% and then incubated overnight or until the cells were confluent for at least 2 days. The coverslips were washed thrice in ice-cold PBS and the cells were fixed in 60% acetone/3.7% formaldehyde for 20 min at −20° C. as described previously (Gelman and Silverstein, 1986, J. Mol. Biol. 191:395–409). After washing in PBS, the cells were incubated for 1 h with immunoaffinity-purified rabbit polyclonal anti-SSeCKS (above; 1:50 dilution) and rhodamine-labeled phalloidin (1:400; Sigma). Secondary antibodies to detect SSeCKS were fluorescein-labeled anti-rabbit Ig(Boehringer Mannheim). The coverslips were mounted in Aqua-Mount (Lerner Laboratories, Pittsburgh, Pa.) containing 20 mM p-phenylenediamine (Kodak) as an anti-bleaching agent.

Regents: All regents were purchased from Sigma unless indicated otherwise.

7.2. Results

SSeCKS is Identical to the ">200 kDa" PKC Substrate

Several novel substrates of PKC have been identified using overlay assays (Hyatt et al., 1994, Cell Growth and Differentiation 5:495–502). The SSeCKS protein appears to be identical to the so-called ">200 kDa" protein identified in that study for the following reasons: (i) recent attempts by the authors of the study to clone the >200 kDa protein yielded partial cDNAs with greater than 99 percent sequence homology to the SSeCKS sequence (in Genbank as the 322 sequence, U23146); and (ii) SSeCKS and the >200 kDa protein share many idiosyncratic characteristics such as resistance to heat denaturation, in vitro phosphorylation by PKC, and phosphatidylserine-dependent binding to PKC (Hyatt et al., 1994, Cell Growth and Differentiation 5:495–502). A 5'-RACE product, p53ext2 was spliced to the 5.4 Kb cDNA described in the foregoing section (FIG. 3) in order to construct a full-length SSeCKS cDNA having a length of 6.0 kb (FIG. 11) SEQ ID NO: 3. FIG. 12 shows that both the upstream and internal ATG sites are independently recognized in T7 transcription/translation system (TNT; Progmega), although the internal site is silence in the context of the upstream sire. Most importantly, the product obtained in vitro from the upstream ATG has a similar mobility in SDS-PAGE to native SSeCKS (280/290 kDA form).

Figure 25B:
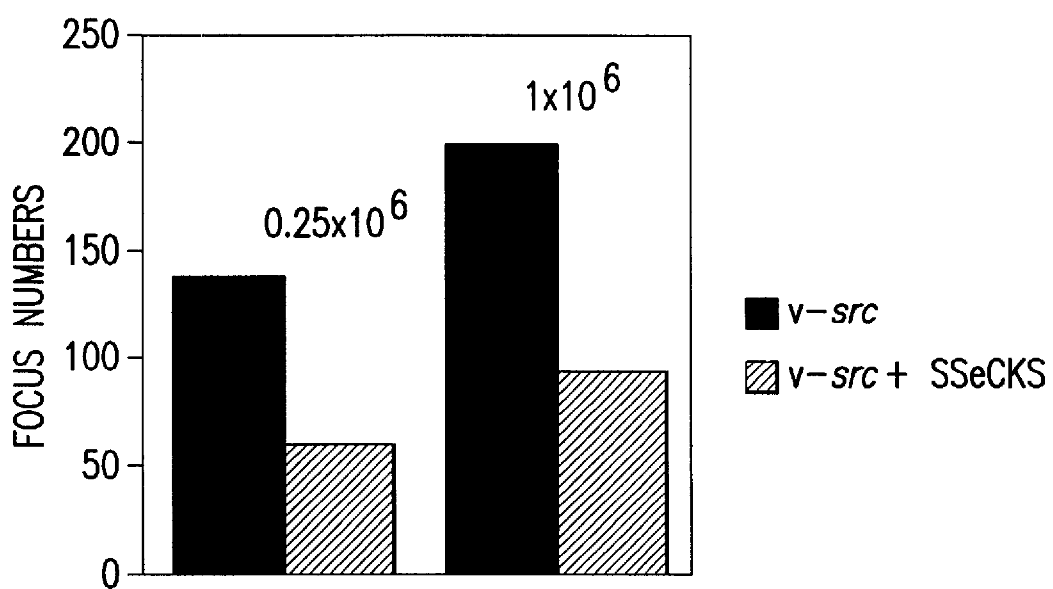

As discussed above, constitutive expression of the SSeCKS truncated protein (encoding amino acids 387–1594; FIG. 11) SEQ ID NO: 3 led to the selection of cells containing deletions of the transduced SSeCKS cDNA. In this section, we evaluated whether over-expression of the full-length SSeCKS cDNA, via a retroviral vector (pBABEhygro) or a vector driven by the MLV-LTR promoter (pCEV27), was toxic in rodent fibroblasts. We found that the presence of the full-length SSeCKS cDNA severely decreased, by more than 95 percent, the frequency of hygromycin-resistant colony formation following either infection with packaged virus or direct DNA transformation of both untransformed and src-transformed cells. The few colonies that did arise showed highly unstable growth characteristics, such as a more than 80 percent decrease in cell viability following trypsinization. These data indicate that high level constitutive expression of full-length SSeCKS or an N-terminal truncated SSeCKS version (see Section 6) is growth inhibitory. FIG. 25 shows that the transient transfection of full-length SSeCKS decreases v-src-induced colony formation in soft agar and focus formation. pMv-src (1 $\mu$g) and SSeCKS-pBabehygro (10 $\mu$g) or pBabehygro (10 $\mu$g) plasmids were co-transfected into NIH3T3 cells. After two days of transfection, $2\times10^6$ and $20\times10^6$ cells were used in a soft agar colony formation assay, the results of which are depicted in FIG. 25A. $0.25\times10^6$ and $1\times10^6$ cells were cultured for the formation of foci (also initiated two days after transfection); the results are shown in FIG. 25B. The suppression of morphological transformation may be due to SSeCK's ability to induce grown arrest or to a selective ability to suppress parameters of transformation in the absence of growth arrest.

Expression of the 322 ORF Products and Production of Specific Antisera

The predicted structure of SSeCKS using the Chou-Fassman algorithm (Chou and Fasman, 1978, Advances in Enzymology 47:45–147) was that of an elongated, rod-shaped protein with a concentration of both CF turns and predicted antigenic sites (Jameson-Wolf index; Wolf et al., 1987, Computer applications in the Biosciences 4:187–191) roughly one third into the coding sequence (FIG. 13). FIG. 15 shows the inducible expression and purification of a GST-322 fusion protein with an apparent mobility on SDS-PAGE of 160 kDa even though the predicted molecular weight is 81 kDa (including GST). This result is consistent with the description in the preceding section of a retarded mobility for the 322 ORF product (the truncated protein), and most likely results from a high concentration of acidic residues as well as an inherent rod-like structure. The smaller polypeptides purified on glutathione columns are considered C-terminal breakdown products inasmuch as Western blotting using anti-GST sera identified the same band pattern as Coomassie blue staining.

In order to characterize the forms of SSeCKS expressed in Rat-6 fibroblasts, rabbit antisera was raised against the purified GST-322 protein. FIGS. 14, 20 and 21 show that three SSeCKS protein species, a 240 kDa and a 280/290 protein doublet, are identified by Western blot analysis using immune rabbit serum (in FIG. 14, the 280/290 doublet is unresolved). Other minor protein species were identified in immunoblots using anti-SSeCKS sera: 120, 95, 60 and 44 KDa. These may represent proteolytically cleaved forms of the larger SSeCKS species (240, 280, 290 KDa) or products of spliced SSeCKS RNAs. The 280/290 kDa doublet form is consistent with the in vitro product generated using the TNT system (FIG. 12) and the bacterially expressed GST-SSeCKS products (FIGS. 15 and 17), further suggesting that posttranslational modifications are only minor contributors to the molecular weights of the mature SSeCKS products in Rat-6 cells. The 240 kDa species may represent either an in vivo utilization of the internal ATG site or a specific proteolytic cleavage product. Interestingly, the 240 kDa species in Rat-6 cells is not readily labeled in vivo with [$^{32}$P] orthophosphate (FIG. 14, top panel), although predicted casein kinase II and PKC sites are found throughout the SSeCKS ORF. In view of data disclosed in the preceding section which showed a single mRNA hybridizing to SSeCKS cDNA probe, the multiple forms of SSeCKS protein observed are most likely due to protein modifications rather than to multiple SSeCKS allelic products.

It was somewhat difficult to metabolically label SSeCKS protein in either subconfluent or confluent cultures using either [$^{35}$S]-methionine/cysteine or [$^{3}$H]-leucine, although $p60^{c\text{-}src}$ was easily labeled in the same lysates. This could not be due to a dearth of Met, Cys or Leu residues in SSeCKS (which occur 20, 15, and 86 times, respectively, in rat SSeCKS). In contrast, SSeCKS could be immunoblotted easily under the same conditions, suggesting that its relative rate of de novo synthesis is low. SSeCKS is not glycosylated in an in vitro mammalian translation system. The addition of tunicamycin to Rat-6 cells did not alter the electrophoretic mobility of SSeCKS as determined by [$^{35}$S]-methionine/cysteine labeling or Western blotting, indicating that SSeCKS is not significantly glycosylated in vivo.

SSeCKS as a PKC Substrate

Activation of PKC by short-term addition of nM concentrations of phorbol esters is known to result in the rapid phosphorylation of PKC substrates such as MARCKS (A. Aderem, 1992, Cell 71:713–716). FIG. 14 (top) indicates that the relative phosphorylation level of the 280/290 kDa species in vivo rapidly increases 5–6 fold in response to PMA, and that this induction is abrogated by the addition of the PKC-specific bis-indolylmaleimide inhibitor, GF-109203X. The PMA-induced phosphorylation effect is apparent in as little as 2 minutes and lasts at least 10 minutes (FIG. 14), but wanes with treatments of longer than 60 minutes although this may reflect down-regulation of PKC (Mahoney et al., 1994, in Protein Kinase C (Kuo, J. F. ed) pp. 16–63, Oxford University Press, New York). This rapid PKC-induced phosphorylation is similar to that of MARCKS (A. Aderem, 1992, Cell 71:713–716; Allen and Aderem, 1995, EMBO J. 14:1109–1121), which is often used as a gauge of PKC activation. Although SSeCKS from quiescent Rat-6 fibroblasts contains no detectable phosphotyrosine, as determined by anti-phosphotyrosine immunoblotting, it cannot be ruled out that tyrosine is being phosphorylated following PMA treatment or activation of ts-v-src. However, SSeCKS is not tyrosine phosphorylated in Rat-6/src cells.

It was then determined that purified rat brain PKC containing $\alpha$, $\beta$, and $\gamma$ isoforms could phosphorylate GST-322 protein in vitro (FIG. 15, panel B). This phosphorylation was inhibited by the addition of excess PKC pseudosubstrate peptide (amino acids 19–36), indicating that PKC and not a contaminating kinase was responsible for phosphorylation. The PKC-specific phosphorylation of GST-322 paralleled that of myelin basic protein (MBP) in its dependence on PS (FIG. 16) and $Ca^{2+}$. PI could supplant PS in this assay, although the relative level of GST-322 phosphorylation was roughly two-fold less than that of MBP using PI (FIG. 16). As previously reported using MBP, PC did not stimulate PKC activity of GST-322 (Mahoney and Huang, 1994, in Protein Kinase C (Kuo, J. F. ed) pp. 16–63, Oxford University Press, New York). Although several C-terminal breakdown products smaller than 70 kDa were present in the preparation of GST-322 (FIG. 15), only the products that were greater than or equal to 70 kDa were phosphorylated in vitro. This suggests that the PKC sites do not map to the extreme C-terminal portion of SSeCKS in the GST-322 construct. Therefore, these data indicate that SSeCKS is both an in vivo and in vitro substrate of PKC.

SSeCKS Binding to PKC

The ability of PKC to phosphorylate GST-322 indicates some level of interaction between these proteins. Results (FIG. 17) indicate that SSeCKS binds both purified PKC and PKC in Rat-6 lysates in a PS-dependent manner. Thus, SSeCKS and PKC most likely interact via a PS bridge, although it cannot be ruled out that there may be a lower affinity protein-protein interaction with domains in SSeCKS not encoded by GST-1322. Pre-phosphorylation of GST-322 by PKC decreases this binding at least 10-fold, suggesting that phosphorylated SSeCKS has decreased binding affinity for PS.

Identification of in vitro PKC Phosphorylation sites on SSeCKS

The consensus motifs for PKC phosphorylation have been identified as ${}^{S}/_{T}X^{K}/_{R}$ or ${}^{K}/_{R}X^{S}/_{T}$, with a greater preference for serine over threonine (Pearson and Kemp, 1991, Meth. Enzymol. 200:63–81). However, our observations of previously characterized in vivo PKC phosphorylation sites indicates that they typically contain a high concentration of basic residues and at least 2 or 3 of the overlapping phosphorylation motifs described above. Analysis of the SSeCKS sequence yielded four such putative phosphorylation sites, shown in Table I. These sites share some linear sequence homology and predicted secondary structural similarity with the PKC phosphorylation site in MARCKS. A minimal MARCKS 23-peptide containing this site (Hartwig et al., 1992, Nature 356:618–622) also binds calmodulin and F-actin (Table 1).

In order to determine whether SSeCKS could be phosphorylated in vitro by PKC, PCR products containing individual predicted PKC phoshorylation sites or several sites (Table 1) in tandem were generated, fused in-frame to GST-expressing vectors (FIG. 13) and checked by sequencing. FIG. 18 indicates that sites 1–4 could be phosphorylated efficiently by purified rabbit brain PKC and that this phosphorylation was blocked by excess pseudosubstrate peptide inhibitor.

TABLE 1

Proposed PKC phosphorylation sites in SSeCKS: Comparison with known calmodulin-binding and PKC phosphorylation sites in the MARCKS protein family and in myosin light chain kinase

| | Sequence | CaM binding | Actin binding | PKC phosph. |
|---|---|---|---|---|
| MARCKS (bovine/chicken) (SEQ ID NO:11) | $^{155}$KRF<u>S</u>SKK<u>S</u>FKLSGF<u>S</u>FKKNKKEA$_{177}$ | + | + | + |
| MARCKS (mouse) (SEQ ID NO:12) | KRFSSKKSFKLSGFSFKKSKKEA | + | + | + |
| MacMARCKS/F52 (SEQ ID NO:13) | KKFSSKKPFKLSGFSFR | + | + | + |
| Myosin light chain kinase[a] (SEQ ID NO:14) | KRRWKKAFIAVSAAARFKKC WAGWRKK (SEQ ID NO:19) | + | – | ? |
| SSeCKS-1 (rat) (SEQ ID NO:15) | $^{279}$ETTSSFKKFFTHGTSFKKSKEDD$_{107}$ | ? | ? | + |
| SSeCKS-2 (rat) (SEQ ID NO:16) | $^{504}$KLFSSSGLKKLSGKKQKGKRGGG$_{526}$ | ? | ? | + |
| SSeCKS-3 (rat) (SEQ ID NO:17) | $^{592}$EGITPWASFKKMVTPKKRVRRPS$_{614}$ | ? | ? | + |
| SSeCKS-4 (rat) (SEQ ID NO:18) | $^{741}$EGVSTWESFKRLVTPRKKSKSKL$_{766}$ | ? | ? | + |
| 3/4-Consensus (SEQ ID NO:20) | EGV W SFKK VTPKKK K<br>I R R R R | | | |

[a]Ref. (44)

SSeCKS is Resistant to Heat Denaturation

Besides having predicted rod-like structures, many PKC substrates share peculiar characteristics such as resistance to heat denaturation (Grohmann et al., 1990, Eur. J. Immunol. 20:629–636; Urbanelli et al., 1989, Virology 173:607–614). FIG. 19 shows that the 280/290 kDa form of SSeCKS remained soluble after 5 minutes of boiling in the absence of SDS. Additionally, boiled SSeCKS retained roughly 50 percent of its immunoreactivity with rabbit immune serum. These data indicate that SSeCKS assumes a rod-like structure in vivo. In contrast, GST fusions of SSeCKS are heat-labile PKC substrates, a characteristic most likely conferred by the GST moiety.

SSeCKS in src and ras Transformed Cells

The SSeCKS encoding gene (i.e. 322) was originally isolated based on its being transcriptionally suppressed in src-transformed NIH3T3 cells (Frankfort and Gelman, 1995, BBRC 206:916–926). It has also been shown that the gene is down-regulated at least 10-fold at the steady-state RNA level in src and ras-transformed Rat-6 fibroblasts but not in cells transformed by activated raf. FIG. 20 shows that the relative level of SSeCKS in src- and ras-transformed Rat-6 fibroblasts is about 10-fold lower than in untransformed cells. An additional 305 kDa protein is found in the Rat-6/ras cells only, which might represent an induced SSeCKS homologue or a modified form of the 280/290 kDa SSeCKS doublet. Thus, the relative abundance of SSeCKS in transformed cells seems to be controlled at the transcriptional level.

Cell Localization of SSeCKS

We determined where SSeCKS is found in subconfluent and confluent Rat-6 cells. Immunofluorescence analysis using immunoaffinity-purified anti-SSeCKS antibody indicates that SSeCKS localizes to the cytoplasm but is enriched at the cell edge, in structures resembling podosomes, and in the perinucleus (FIG. 21). An apparent intranuclear staining of SSeCKS (FIG. 21J) most likely represents deposits of SSeCKS in or on the nuclear cage based on confocal microscopy. The association of SSeCKS with cortical actin-like structures (FIGS. 21A, 21C and 21E) and cellular components such as podosomes (FIG. 21I) further supports a role for SSeCKS in the control of actin-based cytoskeletal architecture.

It has been shown that short-term treatment of quiescent fibroblasts with PMA led to a rapid detachment of MARCKS from plasma membrane sites into a soluble cytoplasmic compartment, followed by its re-association with membrane structures and progressive movement towards the perinucleus (Allen and Aderem, 1995, EMBO J. 14:1109–1121). This effect was coincident with a ruffling of actin fibers at the plasma membrane. We determined the effect of PMA on SSeCKS localization. FIGS. 21 A–F shows that after 10 minutes of PMA treatment, membrane ruffling of actin was apparent in rat fibroblasts, but SSeCKS was still uniformly associated with cortical actin-like structures throughout the cytoplasm. With longer PMA treatment (60 minutes), SSeCKS localized predominantly to the perinucleus. This delayed movement of SSeCKS towards the perinucleus, when compared with MARCKS, suggests that it is a consequence of exocytosis, which is known to be induced by short-term PMA treatment. We then determined whether PMA treatment causes an initial solubilization of SSeCKS. FIG. 22 shows that the relative level of SSeCKS associated with either membrane or soluble subcellular compartments does not change significantly in Rat-6 cells after 30 minutes of PMA treatment. We cannot rule out that PMA induces the solubilization of a minor, membrane-associated component of SSeCKS. These data suggest that most of SSeCKS, unlike MARCKS, remains tethered to cytoskeletal actin structures during movement towards the perinucleus.

7.3. Discussion

The SSeCKS coding sequence contains four domains of overlapping PKC phosphorylation motifs ($^S/_T X^K/_R$ or $^K/_R X^S/_T$) representing potential phosphorylation sites. Each of these sites, designated herein as SSeCKS 1–4, can be phosphorylated in vitro by purified rabbit brain PKC in a PS- and calcium ion dependent manner. The in vitro phosphorylation of SSeCKS could also be supported by PI but not by PC, confirming previous data on the phospholipid cofactor requirements of PKCa (Mahoney and Huang, 1994, in Protein Kinase C (Kuo, J. F. ed) pp. 16–63, Oxford University Press, New York). Moreover, the binding of SSeCKS to PKCa in vitro is PS-dependent, which is consistent with the PS-dependent binding of PKC by the >200 kDa protein (Hyatt et al., 1994, Cell Growth and differentiation 5:495–502).

The first two PKC phosphorylation sites in SSeCKS (SSeCKS1–2 (SEQ ID NOS: 15–16, respectively) Table I) contain significant similarities with a 23-mer MARCKS peptide encoding a minimal PKC phosphorylation site as well as binding ability to calmodulin and F-actin (Hartwig eg al., 1992, Nature 356:618–622). These SSeCKS sites also are enriched for basic residues, as has been reported for other PKC sites (Pearson and Kemp, 1991, Meth. Enzymol. 200:63–81). In contrast to SSeCKS-1 and -2 (SEQ ID NOS: 15–16, respectively) whose sequences are not that similar to each other, SSeCKS-3 and -4 (SEQ ID NOS: 17–18, respectively) share significant sequence and predicted structural homology, although they are less similar to the MARCKS 23-mer PKC site than SSeCKS-1 or -2. This suggests a coordinated or redundant control of the phosphorylation of SSeCKS-3 and -4, (SEQ ID NOS: 15–16, respectively) in vivo.

The SWISSPROT databank was searched for similarities to the putative serine-phosphorylation sites in SSeCKS 1–4 (Table I), with the requirement that potential phosphoserine residues be retained. No significant similarities to SSeCKS-1 SEQ ID NO: 15 were found. The SSeCKS-2 PKC site showed 50 percent identity to a sequence in the retinoic receptor-α (SWISSPROT:Rra1_Mouse) and the SSeCKS-3/4 consensus peptide showed 46.2 percent identity to the A-kinase anchor protein, AKAP-79 (SWISSPROT:Ak79_Human). It is unknown whether these other proteins are phosphorylated by PKC at these sites. However, these similarities to SSeCKS strengthen the notion of a function for SSeCKS at the plasma membrane.

Analysis of the in vitro SSeCKS phosphorylation sites using the HELICALWHEEL program (J. Devereux, 1993, The GCG Sequence Analysis Software Package, Version 8.0, Genetics Computer Group, Inc. Madison Wis.) predicts amphipathic helical structures for SSeCKS-1, -2, and -4, (SEQ ID NOS: 17–18, respectively) but less so for SSeCKS-3 SEQ ID NO: 17. It is difficult to predict whether there is any interplay between these phosphorylations sites as they are separated by between 60–100 residues on a proposed rod-shaped molecule. In the case of MARCKS, McLaughlin and Aderem (McLaughlin and Aderem, 1995, TIBS 20:272–276) postulate that MARCKS probably associates with plasma membranes via its N-terminal myristyl group and its concentration of positively charged amino acid residues in the PKC phosphorylation site. PKC phosphorylates three serines in this site that align along one axis of a short amphipathic-helix. They further postulate that the resulting confluence of electrostatic phosphoserine charges causes MARCKS to detach from plasma membrane sites. Indeed, SSeCKS is enriched at the cell edge and in podosomes (FIG. 21), as has been demonstrated for MARCKS (A. Aderem, 1992, Cell 71:713–716). However, following the activation of PKC, SSeCKS did not detach appreciably from the membrane sites or from subcellular fractions enriched for plasma membranes (FIGS. 21 A–F; FIG. 22). This suggests that the phosphoserine charges in SSeCKS are insufficient to counteract its affinity for membranes. It cannot be ruled out that only a minor component of SSeCKS is membrane-associated in the cell and that following PKC induces this component to move into a soluble cytoplasmic compartment.

The ability of SSeCKS to associate with plasma membrane sites is predicted by an N-terminal myristylation signal, MGAGSSTEQR (SEQ ID NO:7), which is similar to signals encoded by retroviral GAGs and the HIV nef product (Anderson and P Astan, 1975, Adv. Cyclic Nucl. Prot. Phoh. Res. 5:681). This sequence lacks the Cys-3 residue shared by members of the src and Gα family which are also palmitylated, with the exception of Gα t/transducin, the signal of which is quite similar to that of SSeCKS and which is myristylated only. Indeed, SSeCKS was demonstrated to by myristylated by in SSeCKS also localizes to the perinucleus and cytoplasm of Rat-6 cells. No intranuclear staining was detected although SSeCKS encodes at least four nuclear localization signals of the adenovirus Ela motif, $^{K}/_{R}KX^{K}/_{R}$. However, we have detected intranuclear staining the testes, where SSeCKS transcription is highest in the mouse, in a subset of cells in the seminiferous tubules (FIG. 9). SSeCKS may encode both cytoplasmic and nuclear signal and regulatory functions.

Although SSeCKS and MARCKS share little sequence similarity past their PKC phosphorylation sites, they share several biochemical and structural characteristics common to other PKC substrates implicated in the regulation of cytoskeletal architecture such as igloo, GAP-43, and neurogranin. These include (i) a predicted elongated or rod structure; (ii) enrichment for alanine, serine, lysine and glutamic acid residues; (iii) binding to plasma membranes (GAP-43, for example, is palmitoylated); (iv) association with focal contact sites or cellular processes; (v) predicted or proven phospholipid binding activity; and (vi) predicted or proven calmodulin and F-actin binding domains (Mahoney and Huang, 1994, in Protein Kinase C (Kuo, J. F. ed) pp. 16–63, Oxford University Press, New York; Neel and Young, 1994, Development 120:2235–2243; Maekawa et al., 1993, J. Biol. Chem. 268:13703–13709). Additionally, the over-expression of SSeCKS or MARCKS is growth inhibitory. This correlates with the increase in SSeCKS and MARCKS expression as cells enter $G_0$ (Lin et al., 1995, Mol. Cell. Biol. 15:2754–2762; Herget et al., 1993, Proc. nat'l. Acad. Sci. 90:2945–2949). These data suggest that SSeCKS and MARCKS share some overlapping functions and regulatory motifs. However, unlike MARCKS, which is expressed throughout mammalian tissues, and SSeCKS, which is primarily expressed in the brain, genitourinary tract, intestines and kidney, GAP-43, igloo, and neurogranin are brain-specific (Mahoney and Huang, 1994, in "Protein Kinase" C (Kuo, J. F. ed) pp. 16–63, Oxford University Press, New York; Neel and Young, 1994, Development 120:2235–2243; Maekawa et al., 1993, J. Biol. Chem. 268:13703–13709). Additionally, GAP-43, igloo, and neurogranin, but not MARCKS and SSeCKS, encode PKC phosphorylation sites with the so-called "IQ" motif, KIQASFRGH (Cheney and Mooseker, 1992, Curr. Op. Cell Biol. 4:27–35).

SSeCKS localizes to focal contact sites (FIGS. 21H and I) known to be enriched for PKCα, $p125^{FAK}$, and actin-binding proteins. These structures mediate the interaction of cytoplasmic actin fibers with extracellular matrices via integrins (Luna and Hitt, 1992, Science 258:955–963; Zachary and Rozengurt, 1992, Cell 71:891–894). SSeCKS appears to bind to actin in overlay blots, supporting a role for SSeCKS in the regulation of actin-based cytoskeletal architecture.

Recent data indicate that actin fiber formation is controlled by rac and rho-mediated pathways distinct from the raf/MAP kinase-mediated pathways controlling proliferation (Nobes and Hall, 1995, Cell 81:53–62). SSeCKS transcription is suppressed in src and ras but not raf-transformed cells. Thus, the raf-independent control of SSeCKS expression parallels the rac and rho-dependent control of actin-based cytoskeletal architecture.

8. Example: Expression of SSeCKS in Various Human Tissues and Cell Lines

FIG. 23A depicts a Northern blot of RNA prepared from various human tissues, using radiolabeled rat SSeCKS cDNA as a probe. Expression was greatest in human testes, similar to the mouse (see FIG. 9). RNA expression was found to correlate with protein expression; FIG. 23B presents the results of a Western blot analysis of SSeCKS expression in a panel of mouse tissues using antibody directed toward rat SSeCKS protein. Highest levels of SSeCKS protein expression were found in mouse and human testes, with significant amounts of antibody-reactive protein in lung and ovary as well. Immunohistochemical analyses indicate a high level of SSeCKS expression in epithelial cells in the human prostate, breast and testes, although expression in fibroblast-like cells was also apparent.

FIG. 24 depicts the results of a Northern blot analysis of RNA collected from a variety of human tumor cell lines. Radiolabeled rat SSeCKS cDNA was used as a probe. Expression was absent or negligible in HL-60, CML K-562, MOLT-4, LnCaP, colon ca-SW480, and melanoma cell line G361. In contrast, two bands, one approximating in size the 6.0 SSeCKS transcript, were detected in HeLa S3 cells. This indicates that SSeCKS may be transcriptionally suppressed in several human cancers, including but not limited to prostate and colon cancer.

9. Example: SSeCKS is Myristylated

FIG. 26 depicts regions of src, yes, $G_{\alpha i1}$, $G_{\alpha i}$, and GAP-43 (SEQ ID NOS: 5, 6, 8, 9 and 10 respectively) amino acid sequences associated with myristylation and/or palmitylation; the corresponding region found at the N-terminus of rat SSeCKS is compared. Myristylation would facilitate the association of SSeCKS with the plasma membrane.

In order to test whether SSeCKS was myristylated, the full length SSeCKS cDNA was placed under the control of a promoter repressed by the presence of tetracycline, using an expression system based on the tetracycline-resistance (tet) operon of *E. coli* (Gossen and Bujard, 1992, Proc. Natl. Acad. Sci. U.S.A. 89:5547–5551). This system employs a tetracycline-controlled, hybrid trans-activator (tTA) that consists of the tet-repressor ($tet_R$) and the transcriptional trans-activating domain of herpes simplex virus protein 16 (VP16). Tetracycline binds directly to the $tet_R$, inhibiting its DNA binding activity. Removal of tetracycline from the culture medium allows tTA to bind to tet operator sequences placed in front of a minimal mammalian promoter thereby causing rapid induction of cDNAs placed downstream of the tet operator sequences (Gossen and Bujard, 1992, Proc. Natl. Acad. Sci. U.S.A. 89:5547–5551; Schmid, 1995, Trends Cell Biol. 5:266–267).

Using this tet-repressor system, the full-length rat SSeCKS cDNA was inserted into the pUHD15-1. The resulting construct was then transfected into S2-6 cells, Shockett et al., 1995, PNAS, 92:6522–6526, a derivation of NIH3T3. In the presence of tetracycline, SSeCKS was not significantly expressed in the transfectants, but when cells containing the pUHD15-1/SSeCKS construct were placed in tetracycline-free media, SSeCKS expression was induced. FIG. 27 shows that proliferation of transfected cells (clone S2-6/S24) was lower in tetracycline-free medium (−), consistent with the negative effect of SSeCKS on cell proliferation. S2-6/V4 cells, transfected with vector lacking an insert, served as a control.

To evaluate whether SSeCKS is myristylated in vivo, transfected S24 cells containing the SSeCKS/tet-repressor construct were cultured in media containing tritiated myristylate in the presence or absence of tetracycline. The results are shown in FIG. 28, which shows an autoradiograph of SDS-page of a RIPA lysate from tetracycline containing (+) and tetracycline-free (−) cultures. The presence of a myristylated band correlated with the absence of tetracycline and SSeCKS expression, demonstrating that SSeCKS indeed is myristylated in vivo.

10. Example: Deficient SSeCKS in Weaver Mice

Expression of SSeCKS was evaluated in weaver mice, a mutant mouse strain exhibiting aberrant development of the nervous system and testes (Vogelweid et al., 1993, J. Neurogenetics 9:89–104). The mutation is believed to involve a receptor associated with the opiate system. As shown in FIG. 29, depicting a Northern blot analysis of SSeCKS RNA levels in normal Swiss and weaver mutant mice, the level of SSeCKS RNA was decreased or absent in weaver mice. Thus, SSeCKS may be involved with the development of the nervous system and testes.

11. Example: Relationship of SSeCKS and Cell Morphology

FIGS. 30A–D is a series of photomicrographs showing S24 cells transfected with the tetracycline-repressed SSeCKS construct described in section 9, above. FIGS. 30A and B show control cells in media with (A) and without (b) tetracycline (vector alone), exhibiting normal morphology. The morphology of S24 cells in the presence of tetracycline (FIG. 30C) was also normal. In the absence of tetracycline, S24 cells showed increased cell flattening marked by elaboration of the cytoskeletal matrix and increased production of lamellipodia (L) and filopodia (F). The morphological change and growth arrest (FIG. 27) induced by SSeCKS overexpression is suggestive of a terminally differentiated phenotype.

FIGS. 31A–D is a series of photomicrographs of the tetracycline-repressed SSeCKS transfected S24 cells stained with fluorescent labeled antibodies to SSeCKS (FIGS. 31A and 31C) and actin (FIGS. 31B and 31D) in the presence (FIGS. 31A and 31B) and absence (FIGS. 31C and 31D) of tetracycline. SSeCKS overexpression (FIGS. 31C and D) was associated with a loss of actin stress fibers (sf). This is consistent with a role for SSeCKS in the early events of cytoskeleton-associated cell motility of cytokinesis.

FIG. 32A-H shows a similar series of photo-micrographs of S24 transfectants in the absence of tetracycline for 1 (a, b, g, h), 3 (c, d) and 4 (e, f) days, after which the cells were stained for SSeCKS (a, c, e and g) and vinculin (b, d, f, and h). After 1 day, adhesion plaques are detected only in the cell not overexpressing SSeCKS (left cell, panel a/b). After 3 days, adhesion plaques began to form in the SSeCKS overexpressor cells but were not located at the cells' leading edges (le). After 4 days, adhesion plaques were detected at the leading edge in the SSeCKS overexpressor cells. Panels g and h show the inverse expression pattern of SSeCKS and vinculin in filopodia of overexpressor (S24) and non-overexpressor cells (n). Thus, the initial overexpression of SSeCKS delays the formation of vinculin-associated adhesion plaques. Taken together with the result in FIG. 31, this strongly suggests that SSeCKS controls cytoskeletal matrix formation associated with motility or cytokinesis.

Figure 33A:
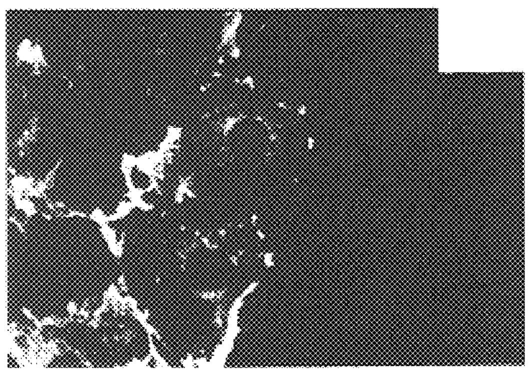
Figure 33B:
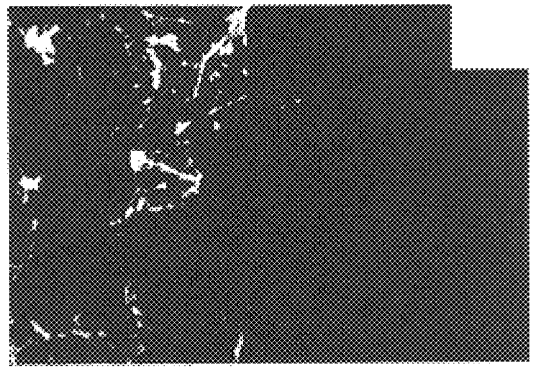
Figure 33C:
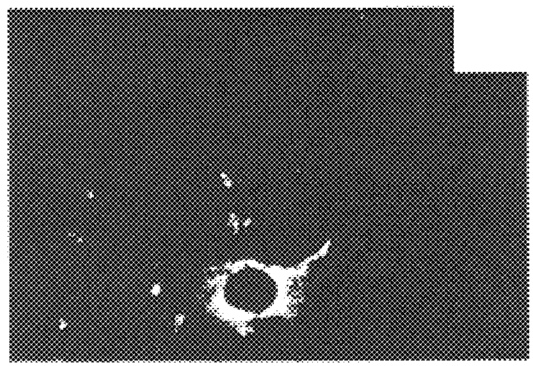
Figure 33D:
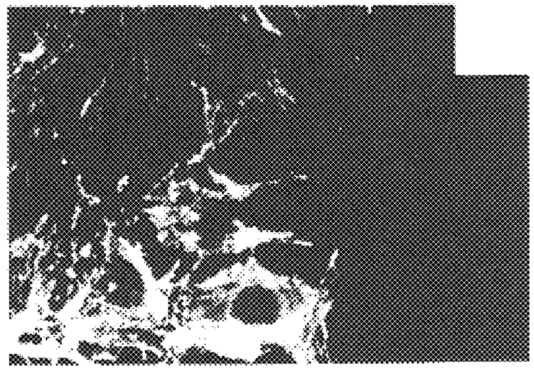

FIGS. 33A–H depict the result of cell-wounding experiments, in which SSeCKS, but not actin, is associated with the growing edge of a cell following injury. Immediately after injury to the monolayer, SSeCKS was present throughout the cell (FIGS. 33A and C) and actin stress fibers were apparent (FIGS. 33B and D). In contrast, the growing edge of peripheral cells 5 hours after injury was enriched with SSeCKS (FIGS. 33E and G) but devoid of actin stress fibers (FIGS. 33F and H).

Various publications are cited herein, which are hereby incorporated by reference in their entireties.

What is claimed is:

1. A purified and isolated nucleic acid molecule comprising the nucleic acid sequence set forth in FIG. 11 (SEQ ID NO:3).

2. A purified and isolated protein comprising the amino acid sequence as set forth in FIG. 11 (SEQ ID NO:4).

3. A purified and isolated protein encoded by the nucleic acid molecule of claim 1.

4. A vector comprising the nucleic acid molecule of claim 1.

5. A host cell, into which the nucleic acid molecule of claim 1 has been introduced.

6. A purified and isolated DNA which hybridizes to the nucleic acid molecule of SEQ ID NO:3 under the following stringent hybridization conditions: 0.75 M sodium phosphate pH 7, 1 mM EDTA, 7% SDS, 1% bovine serum albumin (BSA), 100 micrograms per ml salmon sperm DNA at 12–18 hours at 65 degrees C.; washing twice in 50 mM sodium phosphate, 1 mM EDTA, 1% SDS and 0.5% BSA at 65 degrees C. and twice again in the same solution without BSA at 65 degrees C.; and wherein said nucleic acid molecule codes for a protein:

(i) that is a protein kinase C substrate;

(ii) that is resistant to heat denaturation wherein said resistance can be measured by the ability of the protein to remain soluble after boiling for five minutes in the absence of SDS;

(iii) that is myristylated; and (iv) growth inhibitory.

7. A purified and isolated protein encoded by the nucleic acid molecule of claim 6.

8. A vector comprising the nucleic acid molecule of claim 6.

9. A host cell into which the nucleic acid molecule of claim 6 has been introduced.

* * * * *

UNITED STATES PATENT AND TRADEMARK OFFICE

CERTIFICATE OF CORRECTION

PATENT NO. : 6,582,956 B1
APPLICATION NO. : 08/978277
DATED : June 24, 2003
INVENTOR(S) : Gelman et al.

It is certified that error appears in the above-identified patent and that said Letters Patent is hereby corrected as shown below:

IN THE SPECIFICATION:

Please insert, before Col. 1, line 9 (“INTRODUCTION”), the following paragraph:

-- This invention was made with government support under NIH grant number CA 65787 awarded by the National Institutes of Health. The United States Government has certain rights in the invention. --

Signed and Sealed this

Twenty-second Day of September, 2009

David J. Kappos

*Director of the United States Patent and Trademark Office*